US011236376B2

(12) United States Patent
Heidtman et al.

(10) Patent No.: US 11,236,376 B2
(45) Date of Patent: *Feb. 1, 2022

(54) ALPHA (1,2) FUCOSYLTRANSFERASES SUITABLE FOR USE IN THE PRODUCTION OF FUCOSYLATED OLIGOSACCHARIDES

(71) Applicant: Glycosyn LLC, Woburn, MA (US)

(72) Inventors: Matthew Ian Heidtman, Brighton, MA (US); Massimo Merighi, Somerville, MA (US); John M. McCoy, Reading, MA (US)

(73) Assignee: Glycosyn LLC, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/397,755

(22) Filed: Apr. 29, 2019

(65) Prior Publication Data

US 2020/0087691 A1 Mar. 19, 2020

Related U.S. Application Data

(60) Continuation of application No. 14/708,568, filed on May 11, 2015, now Pat. No. 10,273,516, which is a division of application No. 13/557,655, filed on Jul. 25, 2012, now Pat. No. 9,029,136.

(51) Int. Cl.
*C12P 19/18* (2006.01)
*C12N 15/52* (2006.01)
*C12N 9/10* (2006.01)
*G16B 15/00* (2019.01)
*G16B 35/00* (2019.01)
*G16C 20/60* (2019.01)
*C12N 15/72* (2006.01)

(52) U.S. Cl.
CPC ............ *C12P 19/18* (2013.01); *C12N 9/1051* (2013.01); *C12N 15/52* (2013.01); *C12N 15/72* (2013.01); *C12Y 204/01069* (2013.01); *G16B 15/00* (2019.02); *G16B 35/00* (2019.02); *G16C 20/60* (2019.02)

(58) Field of Classification Search
CPC ......... C12P 19/18; G16B 15/00; G16B 35/00; C12N 15/52; C12N 15/72; C12N 9/1051; C12Y 204/01069; G16C 20/60
USPC .......................................................... 506/8
See application file for complete search history.

(56) References Cited

U.S. PATENT DOCUMENTS

| 6,656,714 | B2 | 12/2003 | Holmes et al. |
| 7,214,517 | B2 | 5/2007 | Kamada et al. |
| 9,029,136 | B2 | 5/2015 | Heidtman et al. |
| 9,587,241 | B2 | 3/2017 | Merighi et al. |
| 10,273,516 | B2 | 4/2019 | Heidtman et al. |
| 2004/0048331 | A1 | 3/2004 | Taylor et al. |
| 2004/0219553 | A1 | 11/2004 | Kamada et al. |
| 2008/0145899 | A1 | 6/2008 | Johnson et al. |
| 2012/0208181 | A1 | 8/2012 | Merighi et al. |
| 2014/0031541 | A1 | 1/2014 | Heidtman et al. |
| 2017/0081353 | A1* | 3/2017 | McCoy ................. C12P 19/00 |
| 2017/0081689 | A1 | 3/2017 | Heidtman et al. |

FOREIGN PATENT DOCUMENTS

| EP | 1 426 441 A1 | 6/2004 |
| EP | 2479263 A1 | 7/2012 |
| JP | 4048173 B2 | 2/2008 |
| WO | 01/77313 A1 | 10/2001 |
| WO | WO 2010070104 A1 | 6/2010 |
| WO | WO 2014018596 A2 | 1/2014 |

OTHER PUBLICATIONS

Scutt et al. Techniques for the removal of marker genes from transgenic plants. Biochimie 84 (2002) 1119-1126. (Year: 2002).*
UNIPROT (Mar. 8, 2011) "Glycosyltransferase Family 11", Accession No. E5UR75, 4 pages.
UNIPROT (Apr. 29, 2008) "Putative Fucosyltransferase WbgN", Accession No. B1B4K2, 3 pages.
UNIPROT (Jun. 16, 2009) "Uncharacterized Protein", Accession No. C3XIB3, 4 pages.
Albermann, et al., "Synthesis of the Milk Oligosaccharide 2'-Fucosyllactose Using Recombinant Bacterial Enzymes", Carbohydrate Research, Sep. 2001, 334(2):97-103.
Altschul, et al., "Basic Local Alignment Search Tool", Journal of Molecular Biology, Oct. 1990, 215(3):403-410.
Altschul, et al., "Gapped BLAST and PSI-BLAST: a New Generation of Protein Database Search Programs", Nucleic Acids Research, Sep. 1, 1997, 25(17):3389-3402.
American Type Culture Collection, "*Escherichia coli*", ATCC 55151 Product Sheet, 2017, 2 pages.
Amonsen, et al., "Human Parainfluenza Viruses hPIV1 and hPIV3 Bind Oligosaccharides with 2-3-Linked Sialic Acids That Are Distinct from Those Bound by H5 Avian Influenza Virus Hemagglutinin", Journal of Virology, Sep. 2007, 81(15):8341-8345.
Appelmelk, et al., "Phase Variation in Helicobacter Pylori Lipopolysaccharide", Infection and Immunity, Jan. 1998, 66(1):70-76.
Bachmann, et al., "Pedigrees of Some Mutant Strains of *Escherichia coli* K-12", Bacteriological Reviews, 1972, 36(4):525-557.
Belfort, et al., "Characterization of the *Escherichia coli* thyA Gene and its Amplified Thymidylate Synthase Product", Proceedings of the National Academy of Sciences, May 1983, 80(7):1858-1861.
Bettler, et al., "The Living Factory: In vivo Production of N-Acetyllactosamine Containing Carbohydrates in *E. coli*", Glycoconjugate Journal, Mar. 1999, 16(3):205-212.

(Continued)

*Primary Examiner* — Yih-Horng Shiao
(74) *Attorney, Agent, or Firm* — Mintz Levin Cohn Ferris Glovsky and Popeo, P.C.; Ingrid A. Beattie

(57) ABSTRACT

The invention provides compositions and methods for engineering *E. coli* or other host production bacterial strains to produce fucosylated oligosaccharides, and the use thereof in the prevention or treatment of infection.

26 Claims, 8 Drawing Sheets

Specification includes a Sequence Listing.

(56) References Cited

OTHER PUBLICATIONS

Bode, et al., "Recent Advances on Structure, Metabolism, and Function of Human Milk Oligosaccharides", The Journal of Nutrition, 2006, 136(8):2127-2130.
Charlwood, et al., "A Detailed Analysis of Neutral and Acidic Carbohydrates in Human Milk", Analytical Biochemistry, 1999, 273(2):261-277.
Chaturvedi, et al., "Fucosylated Human Milk Oligosaccharides Vary Between Individuals and Over the Course of Lactation", Glycobiology, Jun. 2001, 11(5):365-372.
Chaturvedi, et al., "Survival of Human Milk Oligosaccharides in the Intestine of Infants", Advances in Experimental Medicine and Biology, 2001, 501:315-323.
Couceiro, et al., "Influenza Virus Strains Selectively Recognize Sialyloligosaccharides on Human Respiratory Epithelium; The Role of the Host Cell in Selection of Hemagglutinin Receptor Specificity", Virus Research, Aug. 1993, 29(2):155-165.
Court, et al., "Genetic Engineering Using Homologous Recombination", Annual Review of Genetics, 2002, 36:361-388.
Cox, et al., "Structural Analysis of the Lipopolysaccharide from Vibrio Cholerae Serotype O22", Carbohydrate Research, 1997, 304(3-4):191-208.
Coyne, et al., "Human Symbionts Use a Host-Like Pathway for Surface Fucosylation", Science, Mar. 18, 2005, 307(5716):1778-1781.
Crout, et al., "Glycosidases and Glycosyl Transferases in Glycoside and Oligosaccharide Synthesis", Current Opinion in Chemical Biology, Feb. 1998, 2(1):98-111.
Danchin, "Cells need safety valves", BioEssays, 2009, 31(7):769-773.
Database GenBank, "alpha-1,2-fucosyltransferase [Helicobacter cinaedi CCUG 18818]", GenBank Accession No. ZP_07805473.1, Dec. 1, 2010, 1 page.
Database GenBank, "alpha-1,2-fucosyltransferase [Helicobacter mustelae 12198]", GenBank Accession No. YP_003517185.1, Jan. 26, 2012, 1 page.
Database GenBank, "Bacteroides Vulgatus ATCC 8482, Complete Genome", GenBank Accession No. NC_009614, Nov. 16, 2011, 2 pages.
Database GenBank, "fucosyltransferase WbgN [*Escherichia coli* O55:H7 str. CB9615]", GenBank Accession No. YP 003500093, Feb. 14, 2012, 1 page.
Database GenBank, "Fusion cloning vector pTRXFUS, complete sequence", GenBank Accession No. U16857.1, May 24, 1995, 2 pages.
Database GenBank, "Glycosyl Transferase Family Protein [Bacteroides Vulgatus ATCC 8482]", GenBank Accession No. YP_001300461.1, Jan. 26, 2012, 1 page.
Database GenBank, "Hypothetical Protein BACOVA_02214 [Bacteroides ovatus ATCC 8483]", GenBank Accession No. ZP_02065239.1, Nov. 9, 2010, 2 pages.
Database GenBank, "hypothetical protein HP0093 [Helicobacter pylori 26695]", GenBank Accession No. NP 206893.1, Jul. 10, 2012, 2 pages.
Database GenBank, "hypothetical protein HP0094 [Helicobacter pylori 26695]", GenBank Accession No. NP 206894.1, Jul. 10, 2012, 2 pages.
Database GenBank, "Predicted Protein [Helicobacter bilis ATCC 43879]", GenBank Accession No. ZP_04580654.1, Jun. 9, 2010, 1 page.
Database GenBank, "putative alpha-1,2-fucosyltransferase [Bacteroides fragilis NCTC 9343]", GenBank Accession No. CAH09369, Jul. 1, 2011, 2 pages.
Database GenBank, "putative fucosyl transferase [Bacteroides fragilis NCTC 9343]", GenBank Accession No. CAH06753.1, Jul. 1, 2011, 2 pages.
Database GenBank, "Template Plasmid pKD13, Complete Sequence", GenBank Accession No. AY048744.1, Sep. 11, 2001, 2 pages.
Database GenBank, "WbgL [*Escherichia coli*]", GenBank Accession No. ADN43847, Sep. 25, 2010, 1 page.
Database GenBank, "wblA [Vibrio cholerae]", GenBank Accession No. BAA33632, Oct. 16, 1999, 1 page.
Datsenko, et al., "One-Step Inactivation of Chromosomal Genes in *Escherichia coli* K-12 Using PCR Products", PNAS, Jun. 6, 2000, 97(12):6640-6645.
Drouillard, et al., "Large-Scale Synthesis of H-Antigen Oligosaccharides by Expressing Helicobacter pylori α1,2-Fucosyltransferase in Metabolically Engineered *Escherichia coli* Cells", Angewandte Chemie International Edition, Mar. 2006, 45(11):1778-1780.
Dumon, et al., "Assessment of the Two Helicobacter pylori α-1,3-Fucosyltransferase Ortholog Genes for the Large-Scale Synthesis of LewisX Human Milk Oligosaccharides by Metabolically Engineered *Escherichia coli*", Biotechnology Progress, 2004, 20(2):412-419.
Dumon, et al., "In Vivo Fucosylation of Lacto-N-Neotetraose and Lacto-N-Neohexaose by Heterologous Expression of Helicobacter Pylori α-1,3 Fucosyltransferase in Engineered *Escherichia coli*", Glycoconjugate Journal, Jun. 2001, 18(6):465-474.
Dumon, et al., "Production of Lewis x Tetrasaccharides by Metabolically Engineered *E. coli*", ChemBiochem, 2006, 7(2):359-365.
Ebel, et al., "*Escherichia coli* RcsA, a Positive Activator of Colanic Acid Capsular Polysaccharide Synthesis, Functions To Activate Its Own Expression", Journal of Bacteriology, Jan. 1999, 181(2):577-584.
Endo, et al., "Large-scale Production of CMP-NeuAc and Sialylated Oligosaccharides Through Bacterial Coupling", Applied Microbiology and Biotechnology, Mar. 2000, 53(3):257-261.
Endo, et al., "Large-Scale Production of N-Acetyllactosamine Through Bacterial Coupling", Carbohydrate Research, Mar. 1999, 316(1-4):179-183.
Endo, et al., "Large-Scale Production of Oligosaccharides Using Engineered Bacteria", Current Opinion in Structural Biology, Oct. 1, 2000, 10(5):536-541.
Endo, et al., "Large-scale Production of the Carbohydrate Portion of the sialyl-Tn Epitope, α-Neup5Ac-(2→6)-D-GalpNAc, Through Bacterial Coupling", Carbohydrate Research, Feb. 28, 2001, 330(4):439-443.
Enequist, et al., "Energy is Required for Maturation of Exported Proteins in *Escherichia coli*", European Journal of Biochemistry, May 1981, 116(2):227-233.
Flowers, "Chemical Synthesis of Oligosaccharides", Methods in Enzymology, 1978, 50:93-121.
Gottesman, et al., "Regulation of Capsular Polysaccharide Synthesis In *Escherichia coli* K12", Molecular Microbiology, Jul. 1991, 5(7):1599-1606.
Hamosh, "Bioactive Factors In Human Milk", Pediatric Clinics of North America, 2001, 48(1):69-86.
Johnson, "Synthesis of Oligosaccharides by Bacterial Enzymes", Glycoconjugate Journal, 1999, 16(2):141-146.
Koeller, et al., "Synthesis of Complex Carbohydrates and Glycoconjugates: Enzyme-Based and Programmable One-Pot Strategies", Chemical Reviews, Dec. 13, 2000, 100(12):4465-4494.
Koizumi, et al., "Large-Scale Production of UDP-Galactose and Globotriose by Coupling Metabolically Engineered Bacteria", Nature Biotechnology, Sep. 1998, 16(9):847-850.
Kuhlenschmidt, et al., "Sialic Acid Dependence and Independence of Group A Rotaviruses", Advances in Experimental Medicine and Biology, 1999, 473:309-317.
Kunz, et al., "Oligosaccharides in Human Milk: Structural, Functional, and Metabolic Aspects", Annual Review of Nutrition, 2000, 20:699-722.
Lavallie, et al., "A Thioredoxin Gene Fusion Expression System That Circumvents Inclusion Body Formation in the *E. coli* Cytoplasm", Nature Biotechnology, 1993, 11:187-193.
Lavallie, et al., "Thioredoxin as a Fusion Partner for Production of Soluble Recombinant Proteins in *Escherichia coli*", Methods in Enzymology, 2000, 326:322-340.
Li, et al., "Characterization of a Novel α1,2-Fucosyltransferase of *Escherichia coli* O128:B12 and Functional Investigation of its Common Motif", Biochemistry, Jan. 8, 2008, 47(1):378-387.
Mahdavi, et al., "Helicobacter pylori SabA Adhesin in Persistent Infection and Chronic Inflammation", Science, Jul. 26, 2002, 297(5581):573-578.

(56) References Cited

OTHER PUBLICATIONS

Marcobal, et al., "Consumption of Human Milk Oligosaccharides by Gut-Related Microbes", Journal of Agricultural and Food Chemistry, May 2010, 58(9):5334-5340.

Martín-Sosa, et al., "Sialyloligosaccharides in Human and Bovine Milk and in Infant Formulas: Variations with the Progression of Lactation", Journal of Dairy Science, Jan. 2003, 86(1):52-59.

Mergaert, et al., "Transfer of Erwinia Ananas (synonym, Erwinia uredovora) and Erwinia Stewartii to the Genus *Pantoea* emend, as Pantoea ananas (Serrano 1928) comb. nov. and Pantoea stewartii (Smith 1898) comb, nov., Respectively, and Description of *Pantoea stewartii* subsp. i", International Journal of Systematic Bacteriology, Jan. 1993, 43(1):162-173.

Mieschendahl, et al., "A Novel Prophage Independent TRP Regulated Lambda PL Expression System", Nature Biotechnology, 1986, 4(9):802-808.

Morrow, et al., "Human Milk Oligosaccharides are Associated with Protection Against Diarrhea in Breast-Fed Infants", The Journal of Pediatrics, Sep. 2004, 145(3):297-303.

Newburg, et al., "Human Milk Glycans Protect Infants Against Enteric Pathogens", Annual Review of Nutrition, Aug. 2005, 25:37-58.

Newburg, et al., "Innate Protection Conferred by Fucosylated Oligosaccharides of Human Milk Against Diarrhea in Breastfed Infants", Glycobiology, Mar. 1, 2004, 14(3):253-263.

Newburg, et al., "Protection of the Neonate by the Innate Immune System of Developing Gut and of Human Milk", Pediatric Research, 2007, 61:2-8.

Newburg, et al., "Role of Human-Milk Lactadherin in Protection Against Symptomatic Rotavirus Infection", The Lancet, 1998, 351(9110):1160-1164.

Newburg, "Bioactive Components of Human Milk: Evolution, Efficiency, and Protection", Advances in Experimental Medicine and Biology, 501(1):3-10. (2001).

Newburg, "Human Milk Glycoconjugates that Inhibit Pathogens", Current Medicinal Chemistry, 6(2):117-127. (1999).

Ninoneuvo, et al., "A Strategy for Annotating the Human Milk Glycome", Journal of Agricultural and Food Chemistry, 2006, 54(20):7471-7480.

Palcic, "Biocatalytic Synthesis of Oligosaccharides", Current Opinion in Biotechnology, 1999, 10(6):616-624.

Parker, "Identification of the purC Gene Product of *Escherichia coli*", Journal of Bacteriology, 1984, 157(3):712-717.

Parkkinen, et al., "Isolation of Sialyl Oligosaccharides and Sialyl Oligosaccharide Phosphates from Bovine Colostrum and Human Urine", Methods in Enzymology, 1987, 138:289-300.

Ruffing, et al., "Metabolic Engineering of Microbes for Oligosaccharide and Polysaccharide Synthesis", Microbial Cell Factories, Jul. 21, 2006, 5(25):1-9.

Ruiz-Palacios, et al., "Campylobacter jejuni Binds Intestinal H(O) Antigen (Fuc$\alpha$1, 2Gal$\beta$1, 4GlcNAc), and Fucosyloligosaccharides of Human Milk Inhibit its Binding and Infection", Journal of Biological Chemistry, 2003, 278(16):14112-14120.

Rydell, et al., "Human Noroviruses Recognize Sialyl Lewis x Neoglycoprotein", Glycobiology, 2009, 19(3):309-320.

Sanger, et al., "Nucleotide Sequence of Bacteriophage $\lambda$ DNA", Journal of Molecular Biology, Dec. 25, 1982, 162(4)729-773.

Schallmey, et al., "Developments in the Use of *Bacillus* Species for Industrial Production", Canadian Journal of Microbiology, Jan. 2004, 50(1):1-17.

Scharfman, et al., "Sialyl-Lex and Sulfo-Sialyl-Lex Determinants are Receptors for P. aeruginosa", Glycoconjugate Journal, Oct. 2000, 17(10):735-740.

Seeberger, "Automated Carbohydrate Synthesis to Drive Chemical Glycomics", Chemical Communications, 2003, 10:1115-1121.

Shen, et al., "Resolution of Structural Isomers of Sialylated Oligosaccharides by Capillary Electrophoresis", Journal of Chromatography A, Jul. 6, 2001, 921(2):315-321.

Siegele, et al., "Mutations in the flhD Gene of *Escherichia coli* K-12 do not Cause the Reported Effect on Cell Division", FEMS Microbiology Letters, Aug. 2010, 309(1):94-99.

Snap Gene, "pQE-80L", Plasmid Files, Map and Sequence File, Accessed on Apr. 14, 2014; http://www.snapgene.com/resources/plasmid_files/qiagen_vectors/pQE-80L/.

Stein, et al., "Cloning Genes for Proline Biosynthesis from Neisseria Gonorrhoeae: Identification by Interspecific Complementation of *Escherichia coli* Mutants", Journal of Bacteriology, May 1984, 158(2):696-700.

Stevenson, et al., "Organization of the *Escherichia coli* K-12 Gene Cluster Responsible for Production of the Extracellular Polysaccharide Colanic Acid", Journal of Bacteriology, Aug. 1996, 178(16):4885-4893.

UniProt Consortium, "Glycosyltransferase family 11", UniProt Accession No. A6L575, Version 1, Jul. 24, 2007, 1 page.

UniProt Consortium, "WbgL", UniProt Accession No. E2DNL9, Version 6, Feb. 22, 2012, 1 page.

Wang, et al., "Development of a Serogroup-Specific Multiplex PCR Assay to Detect a Set of *Escherichia coli* Serogroups Based on the Identification of Their O-Antigen Gene Clusters", Molecular and Cellular Probes, Oct. 2010, 24(5):286-290.

Ward, et al., "Human Milk Metagenome: a Functional Capacity Analysis", BMC Microbiology, May 25, 2013, 13(116):1-12.

Westers, et al., "Bacillus Subtilis as Cell Factory for Pharmaceutical Proteins: a Biotechnological Approach to Optimize the Host Organism", Biochimica et Biophysica Acta (BBA)—Molecular Cell Research, Nov. 11, 2004, 1694(1):299-310.

Wymer, et al., "Enzyme-Catalyzed Synthesis of Carbohydrates", Current Opinion in Chemical Biology, Feb. 1, 2000, 4(1):110-119.

Xu, et al., "Evolution of Symbiotic Bacteria in the Distal Human Intestine", PLoS Biol., 2007, 5(7):1-13(156) for GenBank Accession No. ABR40839.1.

Yamasaki, et al., "The Genes Responsible for O-Antigen Synthesis of Vibrio Cholerae O139 are Closely Related to Those of Vibrio CholeraeO22", Gene, Sep. 17, 1999, 237(2):321-332.

Zimbro, et al., "Difco™ & BBL™ Manual", Manual of Microbiological Culture Media, Second Edition, 2009, 3 pages.

\* cited by examiner

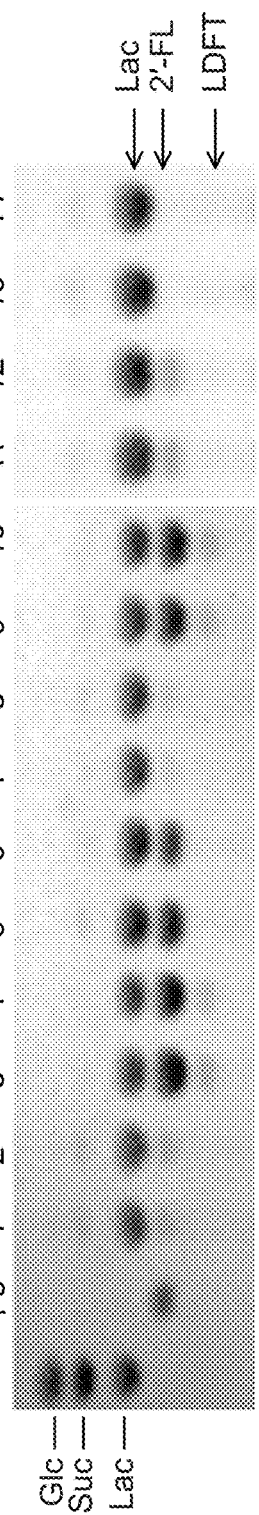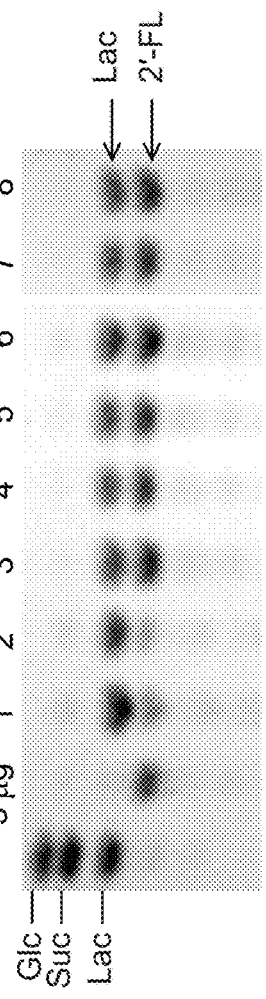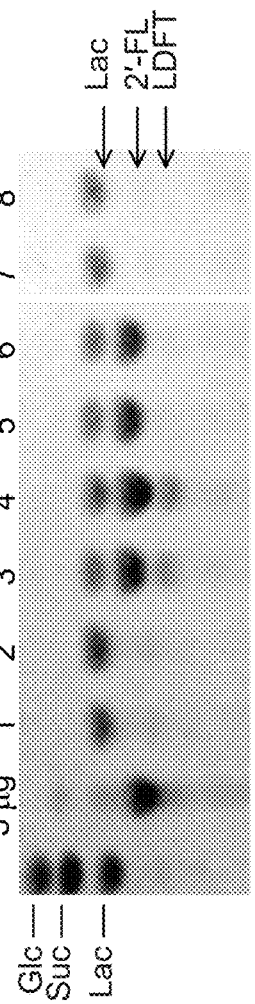
FIG. 3A
FIG. 3B
FIG. 3C

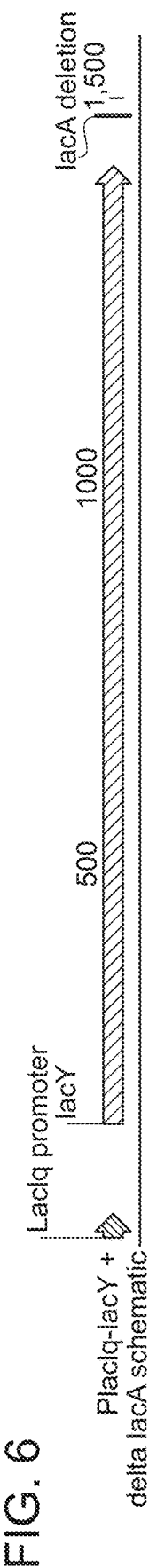
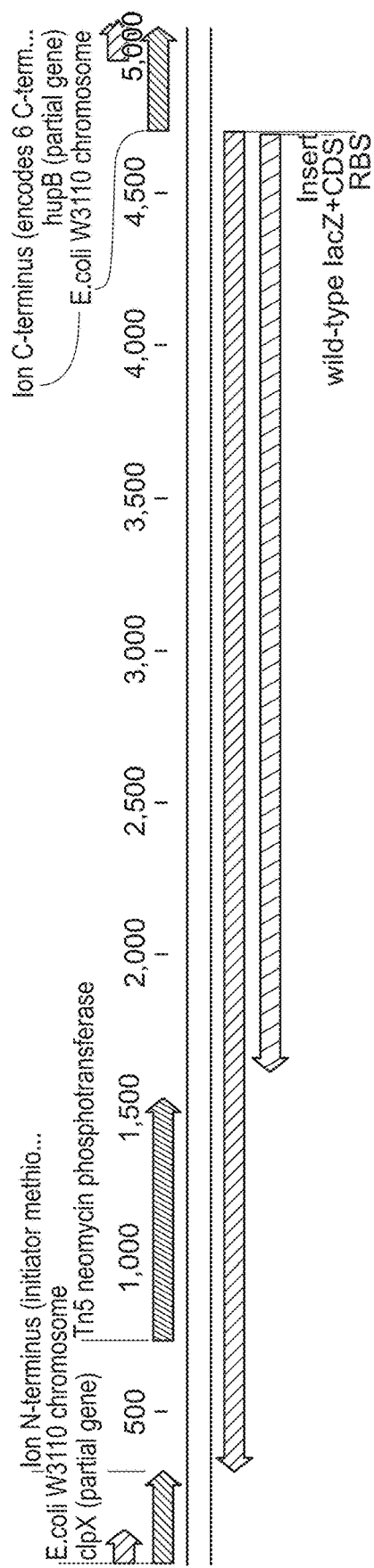

ALPHA (1,2) FUCOSYLTRANSFERASES SUITABLE FOR USE IN THE PRODUCTION OF FUCOSYLATED OLIGOSACCHARIDES

RELATED APPLICATIONS

This application is a continuation of U.S. application Ser. No. 14/708,568, filed May 11, 2015, now U.S. Pat. No. 10,273,516, issued Apr. 30, 2019, which is a divisional application of U.S. application Ser. No. 13/557,655, filed Jul. 25, 2012, now U.S. Pat. No. 9,029,136, issued May 12, 2015, the entire contents of which are incorporated herein by reference.

INCORPORATION-BY-REFERENCE OF SEQUENCE LISTING

The contents of the text file named "37847-510F01US_ST25.txt", which was created on Aug. 20, 2012 and is 71.1 KB in size, are hereby incorporated by reference in their entirety.

FIELD OF THE INVENTION

The invention provides compositions and methods for producing purified oligosaccharides, in particular certain fucosylated oligosaccharides that are typically found in human milk.

BACKGROUND OF THE INVENTION

Human milk contains a diverse and abundant set of neutral and acidic oligosaccharides. More than 130 different complex oligosaccharides have been identified in human milk, and their structural diversity and abundance is unique to humans. Although these molecules may not be utilized directly by infants for nutrition, they nevertheless serve critical roles in the establishment of a healthy gut microbiome, in the prevention of disease, and in immune function. Prior to the invention described herein, the ability to produce human milk oligosaccharides (HMOS) inexpensively was problematic. For example, their production through chemical synthesis was limited by stereo-specificity issues, precursor availability, product impurities, and high overall cost. As such, there is a pressing need for new strategies to inexpensively manufacture large quantities of HMOS.

SUMMARY OF THE INVENTION

The invention features an efficient and economical method for producing fucosylated oligosaccharides. Such production of a fucosylated oligosaccharide is accomplished using an isolated nucleic acid comprising a sequence encoding a lactose-utilizing α (1,2) fucosyltransferase gene product (e.g., polypeptide or protein), which is operably linked to one or more heterologous control sequences that direct the production of the recombinant fucosyltransferase gene product in a bacterium such as Escherichia coli (E. coli). In one example, the bacterium is an enteric bacterium. The amino acid sequence of the lactose-accepting α (1,2) fucosyltransferase gene product is preferably at least 10% and less than 40% identical to FutC (SEQ ID NO:2).

Also within the invention is a nucleic acid construct comprising an isolated nucleic acid encoding a lactose-accepting α (1,2) fucosyltransferase enzyme, said nucleic acid being operably linked to one or more heterologous control sequences that direct the production of the enzyme in a host bacteria production strain, wherein the amino acid sequence of the gene product (enzyme) encoded by the nucleic acid comprises about 70% identity to SEQ ID NO:2. For example, the construct comprises SEQ ID NO: 7, which encodes a FutL protein. By "heterologous" is meant that the control sequence and protein-encoding sequence originate from different bacterial strains. A suitable production host bacterial strain is one that is not the same bacterial strain as the source bacterial strain from which the fucosyltransferase-encoding nucleic acid sequence was identified.

A method for producing a fucosylated oligosaccharide, e.g., an HMOS, in a bacterium is carried out by providing a bacterium such as a production host strain, Escherichia coli (E. coli), that is characterized by a reduced level of β-galactosidase activity, a defective colanic acid synthesis pathway, a mutation in an ATP-dependent intracellular protease, a mutation in a lacA gene and an exogenous α (1,2) fucosyltransferase gene. Preferably, a mutation in a thyA gene in the host bacterium allows for the maintenance of plasmids that carry thyA as a selectable marker gene. Exemplary alternative selectable markers include antibiotic resistance genes such as BLA (beta-lactamase), or proBA genes (to complement a proAB host strain proline auxotropy) or purC (to complement a purC host strain adenine auxotrophy). The bacterium comprising these characteristics is cultured in the presence of lactose, and a fucosylated oligosaccharide is retrieved from the bacterium or from a culture supernatant of the bacterium. In some cases, the method further comprises culturing the bacterium in the presence of tryptophan and in the absence of thymidine. In preferred embodiments, the production host strain comprises E. coli K12. Other production host organisms are listed below.

The invention provides a purified fucosylated oligosaccharide produced by the methods described herein. The fucosylated oligosaccharide is purified for use in therapeutic or nutritional products, or the bacterium is used directly in such products. The fucosylated oligosaccharide produced by the engineered bacterium is 2'-fucosyllactose (2'-FL) or lactodifucotetraose (LDFT). The new alpha 1,2-fucosyltransferases are also useful to synthesize HMOS of larger molecular weight bearing alpha 1,2 fucose moieties, e.g., lacto-N-fucopentaose (LNF I) and lacto-N-difucohexaose (LDFH I).

The bacterium used to produce the oligosaccharides is genetically engineered to comprise an increased intracellular guanosine diphosphate (GDP)-fucose pool (compared to wild type), an increased intracellular lactose pool (compared to wild type), and to comprise fucosyltransferase activity. Accordingly, an endogenous lacZ gene and an endogenous lacI gene of the E. coli are deleted or functionally inactivated to reduce the level of β-galactosidase activity. The bacterium may also comprise a mutation in the lacA gene. The isolated E. coli bacterium also comprises a lacIq gene promoter immediately upstream of a lacY gene. In some cases, the isolated E. coli bacterium comprises a defective colanic acid synthesis pathway due to an endogenous wcaJ gene of the E. coli being deleted or functionally inactivated. The bacterium comprises a mutation in an adenosine-5'-triphosphate (ATP)-dependant intracellular protease. For example, the bacterium comprises a null mutation in a lon gene. The bacterium also comprises a mutation in a thyA gene. Preferably, the bacterium accumulates an increased intracellular lactose pool and an increased intracellular GDP-fucose pool. In one aspect, the E. coli bacterium comprises the genotype ΔampC::$P_{trp}{}^B$cI, Δ(lacI-lacZ)::FRT, $P_{lacIq}$lacY$^+$, ΔwcaJ::FRT, thyA::Tn10, Δlon:(npt3, lacZ$^+$), ΔlacA.

The bacterium possesses fucosyl transferase activity. For example, the bacterium comprises an exogenous α (1,2) fucosyltransferase gene. Preferably, the exogenous α (1,2) fucosyltransferase gene comprises at least 10% homology/identity and less than 40% at the amino acid level to *Helicobacter pylori* 26695 alpha-(1,2) fucosyltransferase (futC), e.g., at least 15%, at least 20%, at least 25%, at least 30% identity. In other examples, the sequences are at least 50%, at least 55%, at least 60%, at least 65%, at least 70%, at least 75%, at least 80%, at least 85%, at least 90%, at least 95% homology/identity to *Helicobacter pylori* 26695 alpha-(1,2) fucosyltransferase (futC). In one example, FutL is 70% identical to FutC at the amino acid level.

The term "% identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For example, % identity is relative to the entire length of the coding regions of the sequences being compared.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Percent identity is determined using search algorithms such as BLAST and PSI-BLAST (Altschul et al., 1990, J Mol Biol 215:3, 403-410; Altschul et al., 1997, Nucleic Acids Res 25:17, 3389-402). For the PSI-BLAST search, the following exemplary parameters are employed: (1) Expect threshold was 10; (2) Gap cost was Existence: 11 and Extension:1; (3) The Matrix employed was BLOSUM62; (4) The filter for low complexity regions was "on". The bacterium expresses a fucosyltransferase gene product encoded by a sequence that is not identical to futC.

Exemplary α (1,2) fucosyltransferase genes include *Escherichia coli* O126 wbgL, *Helicobacter mustelae* 12198 (ATCC 43772) alpha-1,2-fucosyltransferase (futL), and *Bacteroides vulgatus* ATCC 8482 glycosyl transferase family protein (futN). An exogenous α (1,2) fucosyltransferase gene is selected from the group consisting of *Escherichia coli* O126 wbgL, *Helicobacter mustelae* 12198 (ATCC 43772) alpha-1,2-fucosyltransferase (futL), *Bacteroides vulgatus* ATCC 8482 glycosyl transferase family protein (futN), *Bacteroides fragilis* (NCTC) 9343 fucosyl transferase (bft3/wcfB), *Escherichia coli* O55:H7 (str. CB9615) fucosyltransferase (wbgN), *Helicobacter bilis* ATCC 437879 futD, *Vibrio cholera* O22 wblA, *Bacteroides fragilis* (NCTC) 9343 alpha-1,2-fucosyltransferase (bft1), *Bacteroides ovatus* ATCC 8483 futO, and *Helicobacter cinaedi* CCUG 18818 alpha-1,2-fucosyltransferase (futE).

The invention also features a vector, e.g., a vector containing a nucleic acid. The vector can further include one or more regulatory elements, e.g., a heterologous promoter. The regulatory elements can be operably linked to a gene encoding a protein, a gene construct encoding a fusion protein gene, or a series of genes linked in an operon in order to express the fusion protein. In yet another aspect, the invention comprises an isolated recombinant cell, e.g., a bacterial cell containing an aforementioned nucleic acid molecule or vector. The nucleic acid is optionally integrated into the genome.

Also provided is a nucleic acid construct comprising at least one of a promoter of bacteriophage λ, an *E. coli* rcsA gene, a bla gene, and a native thyA gene. As an example of such a construct, the plasmid map of pG171 in FIG. 5.

The sequence of pG171 is set forth below with annotations from GenBank regarding specific features (SEQ ID NO: 1):

```
LOCUS       pEC2-futC-MYC-rcsA-thyA_(pG171) 6244 bp DNA
            circular SYN 24-MAY-1995
DEFINITION  Fusion cloning vector pTRXFUS, complete sequence.
ACCESSION   U16857
VERSION     U16857.1 GI: 575447
KEYWORDS    thioredoxin gene fusion vector.
SOURCE      Cloning vector pTRXFUS (unknown)
ORGANISM    Cloning vector pTRXFUS
            other sequences; artificial sequences; vectors.
REFERENCE   1 (bases 1 to 3585)
AUTHORS     LaVallie, E. R., DiBlasio, E. A., Kovacic, S., Grant, K. L.,
            Schendel, P. F. and McCoy, J. M.
TITLE       A thioredoxin gene fusion expression system that circumvents
            inclusion body formation in the E. coli cytoplasm
JOURNAL     Biotechnology (N.Y.) 11 (2), 187-193 (1993)
PUBMED      7763371
REFERENCE   2 (bases 1 to 3585)
AUTHORS     LaVallie, E. R.
TITLE       Direct Submission
JOURNAL     Submitted (3-NOV-1994) Edward R. LaVallie, Genetics Institute,
            87
            CambridgePark Drive, Cambridge, MA 02140, USA
FEATURES    Location/Qualifiers
Primer      163 . . . 183
            /label=lacZR6
CDS         243 . . . 481
            /gene="lgt"
            /note="ECK2824:JW2796:b2828"
            /codon_start=1
            /transl_table=11
            /product="phosphatidylglycerol-
            prolipoproteindiacylglyceryl
            transferase"
```

| | |
|---|---|
| | /protein_id="BAE76897.1"<br>/db_xref="GI:85675644"<br>/translation="MTSSYLHFPEFDPVIFSIGPVALHWYGLMYLVGFIFAMWLATRRA<br>NRPGSGWTKNEVENLLYAGFLGVFLGGRIGYVLFYNFPQFMADPLYLFRVWDSFHG<br>GLIGVIVVMIIFARRTKRSFFQVSDFIAPLIPFGLGAGRLGNFINGELWGRVDPNFPFA<br>MLFPGSRTEDILLLQTNPQWQSIFDTYGVLPRHPSQLYELLLEGVVLFIILNLYIRKPR<br>PMGAVSGLFLIGYGAFRIIVEFFRQPDAQFTGAWVQYISMGQILSIPMIVAGVIMMVA<br>YRRSPQQHVS" |
| Source | complement(243 . . . 1365)<br>/organism="*Escherichia coli* W3110"<br>/mol_type="genomic DNA"<br>/strain="K-12"<br>/sub_strain="W3110"<br>/db_xref="taxon:316407"<br>/note="synonym: *Escherichia coli* str. K12 substr. W3110" |
| Source | complement(242^243)<br>/organism="*Escherichia coli* W3110"<br>/mol_type="genomic DNA"<br>/strain="K-12"<br>/sub_strain="W3110"<br>/db_xref="taxon:316407"<br>/note="synonym: *Escherichia coli* str. K12 substr. W3110" |
| Primer | 243 . . . 266<br>/note=cagtcagtcaggcgccTCCTCAACCTGTATATTCGTAAAC<br>/label=THYA-F |
| Promoter | 359 . . . 364<br>/label="thyA -35" |
| Promoter | 380 . . . 385<br>/label="thyA WEAK -10" |
| Binding_site | 479 . . . 484<br>/label="thyA RBS" |
| Gene | 488 . . . 1282<br>/gene="thyA" |
| CDS | 488 . . . 1282<br>/gene="thyA"<br>/note="ECK2823:JW2795:b2827"<br>/codon_start=1<br>/transl_table=11<br>/product="thymidylate synthetase"<br>/protein_id="BAE76896.1"<br>/db_xref="GI:85675643"<br>/translation="MKQYLELMQKVLDEGTQKNDRTGTGTLSIFGHQMRFNLQDGFPLV<br>TTKRCHLRSIIHELLWFLQGDTNIAYLHENNVTIWDEWADENGDLGPVYGKQWRTP<br>DGRHIDQITTVLNQLKNDPDSRRIIVSAWNVGELDKMALAPCHAFFQFYVADGKLSL<br>YQRSCDVFLGLPFNIASYALLVHMMAQQCDLEVGDFVWTGGDTHLYSNHMDQLSR<br>EPRPLPKLIIKRKPESIFDYRFEDFEIEGYDPHPGIKAPVAI" |
| Hairpin_loop | 1304 . . . 1310<br>/label=Terminator |
| Hairpin_loop | 1317 . . . 1323<br>/label=Terminator |
| Primer | complement(1345 . . . 1365)<br>/note=cagtcagtcaggcgccTTCGGGAAGGCGTCTCGAAGA<br>/label=THYA-R |
| Primer | complement(1468 . . . 1489)<br>/label=lacZF5 |
| Primer | 1508 . . . 1524<br>/label=aspAseq |
| Gene | 1536 . . . 1588<br>/gene="dsrB" |
| Primer | 1536 . . . 1558<br>/note=cagtcagtcaaagcttTCTTTAATGAAGCAGGGCATCAG<br>/label=rcsA-R |
| Hairpin_loop | complement(1600 . . . 1610)<br>/label=Hairpin |
| Hairpin_loop | complement(1615 . . . 1625)<br>/label=Hairpin |
| CDS | complement(1632 . . . 2255)<br>/gene="rcsA"<br>/note="ECK1949:JW1935:b1951"<br>/codon_start=1<br>/transl_table=11<br>/product="DNA-binding transcriptional co-regulator withRcsB"<br>/protein_id="BAA15776.1"<br>/db_xref="GI:1736617"<br>/translation="MSTIIMDLCSYTRLGLTGYLLSRGVKKREINDIETVDDLAIACDS<br>QRPSVVFINEDCFIHDASNSQRIKLIINQHPNTLFIVFMAIANVHFDEYLLVRKNLLIS |

-continued

| | |
|---|---|
| | SKSIKPESLDDILGDILKKETTITSFLNMPTLSLSRTESSMLRMWMAGQGTIQISDQMN |
| | IKAKTVSSHKGNIKRKIKTHNKQVIYHVVRLTDNVTNGIFVNMR" |
| Promoter | complement(2393 . . . 2398) |
| | /label=-10 |
| Promoter | complement(2419 . . . 2424) |
| | /label=-35 |
| Primer | complement(2473 . . . 2495) |
| | /note=cagtcagtcaaagcttCTACGAACATCTTCCAGGATACT |
| | /label=rcsA-F2 |
| Terminator | complement(2502 . . . 2571) |
| | /note="aspA transcription terminator" |
| Primer | complement(2553 . . . 2574) |
| | /note=cagtcagtcaCTCGAGGCTGCAGTAATCGTACAGGGTAG |
| | /label=PLvect2 |
| Primer_binding_ | 2575 . . . 2644 |
| | /PCR_primers=cagtcagtcactcgagtTTAattcaaatcttcttcagaaatcaatt |
| | tttgttcAGCGTTATACTTTTGGGATTTTACCTC |
| | /label="Primer 0011-futCMYC-4" |
| CDS | complement(2574^2575) |
| | /note="Identical to previously sequenced to |
| | BacteroidesfragilisSWALL:Q9F7604.3e- |
| | 123,coli(EMBL:AF461121) |
| | id" |
| | /transl_table=11 |
| | /product="putative LPS biosynthesis |
| | relatedalpha-1,2-fucosyltransferase" |
| | /gene=wcfW |
| | /locus_tag=BF1902 |
| | /protein_id=CAH07600.1 |
| | /translation=MIVSSLRGGLGNQMFIYAMVKAMALRNNVPAFNLTTDFANDEVYK |
| | RKLLLSYFALDLPENKKLTFDFSYGNYYRRLSRNLGCHILHPSYRYICEERPPHFESRL |
| | ISSKITNAPFLEGYWQSEKYFLDYKQEIKEDFVIQKKLEYTSYLELEEIKLLDKNAIMIG |
| | VRRYQESDVAPGGVLEDDYYKCAMDIMASKVTSPVFFCFSQDLEWVEKHLAGKYPVRLISKKEDDSGTIDDMFLM |
| | MHFRNYIISNSSFYWWGAWLSKYDDKLVIAPGNFINKDSVPESWFKLNVR |
| POLYLINKER | complement(2575 . . . 2580) |
| Protein | complement(2578 . . . 2581) |
| | /label="K.lactis alpha-factor leader" |
| Gene | complement(2582 . . . 3055) |
| | /locus_tag="HP0093" |
| | /db_xref="GeneID:900162" |
| CDS | complement(2582 . . . 3517) |
| | /label="futC strain 26695 (fixed)" |
| Source | 2582 . . . 3517 |
| | /organism="Helicobacter pylori 26695" |
| | /mol_type="genomic DNA" |
| | /strain="26695" |
| | /db_xref="taxon:85962" |
| MYC-tag | complement(2585 . . . 2617) |
| Primer | 2968 . . . 2990 |
| | /note=GATAGTCAATACCAAGCTGACAG |
| | /label=3-6-R |
| Primer | 2968 . . . 2990 |
| | /label="42 (3-6-R)" |
| Gene | complement(3052 . . . 3517) |
| | /locus_tag="HP0094" |
| | /db_xref="GeneID:899021" |
| Primer | complement(3495 . . . 3517) |
| | /note=GAAttcaagaaggagatataCATATGGCTTTTAAGGTGGTGCAAAT |
| | /label=pLfutC-F |
| Source | 3517^3518 |
| | /organism="Escherichia coli W3110" |
| | /mol_type="genomic DNA" |
| | /strain="K-12" |
| | /sub_strain="W3110" |
| | /db_xref="taxon:316407" |
| | /note="synonym:Escherichia coli str. K12 substr. |
| | W3110" |
| RBS | complement(3521 . . . 3535) |
| | /label="T7 gene 10 RBS" |
| Source | complement(3541 . . . 3715) |
| | /note="originates from LAMCG" |
| | /label="lambda DNA" |
| Primer | 3541 . . . 3567 |
| | /note=cagtcagtcagaattcTAACAATTGATTGAATGTATGCAAATA |
| | /label=pLnut-R |
| Region | complement(3544) |
| | /label="TR1 termination site" |

| | |
|---|---|
| note | 3544<br>/note="original sequenced pEC2-BfT2-MYC plasmid is a mixture of C and A here. This plasmid is A" |
| Misc._feature | complement(3547 . . . 3553)<br>/label="TR1 rho-dep consensus box" |
| Region | complement(3566 . . . 3571)<br>/label="TR1 termination site" |
| Misc._feature | complement(3580 . . . 3599)<br>/note="rho utilization site B (rutB)" |
| Misc._binding | complement(3600 . . . 3616)<br>/note="N-utilization rightward; putative"<br>/bound_moiety="Nutr" |
| Region | complement(3601 . . . 3632)<br>/label=nutR |
| Misc._feature | complement(3615 . . . 3632)<br>/note="rho utilization site A (rutA)" |
| Variation | complement(3636 . . . 3715)<br>/note="imm434 region" |
| CDS | complement(3640 . . . 3715)<br>/codon_start=1<br>/transl_table=11<br>/product="cro (antirepressor; also tof;66)"<br>/protein_id="AAA96582.1"<br>/db_xref="GI:215148"<br>/translation="MEQRITLKDYAMRFGQTKTAKDLGVYQSAINKAIHAGRKIFLTIN ADGSVYAEEVKPFPSNKKTTA" |
| Region | complement(3729 . . . 3730)<br>/label="1/2 HaeIII site that Rosenberg used" |
| CDS | complement(3731 . . . 3907)<br>/codon_start=1<br>/transl_table=11<br>/product="N (early gene regulator;133)"<br>/protein_id="AAA96578.1"<br>/db_xref="GI:508997"<br>/translation="MCQSRGVFVQDYNCHTPPKLTDRRIQMDAQTRRRERRAEKQAQWK AANPLLVGVSAKPVNRPILSLNRKPKSRVESALNPIDLTVLAEYHKQIESNLQRIERKNQRTWYSKPGERGITCS GRQKIKGKSIPLI" |
| Source | complement(3731 . . . 4023)<br>/note="originates from LAMCG rev"<br>/label="lambda DNA" |
| Region | complement(3731 . . . 3733)<br>/label="1/2 HpaI site that Rosenberg used" |
| Variation | 3731 . . . 4184<br>/note="imm21 region" |
| Misc._binding | complement(3987 . . . 4003)<br>/note="N-utilization leftward.; putative"<br>/bound_moiety="Nutl" |
| Region | complement(3988 . . . 4018)<br>/label=nutL |
| Source | complement(4024 . . . 4184)<br>/note="originates from LAMCG rev"<br>/label="lambda DNA" |
| Primer | 4024 . . . 4044<br>/note=cagtcagtcagaaTTCATGGTGGTCAGTGCGTCC<br>/label=PLvect3 |
| Region | complement(4024 . . . 4369)<br>/note="originates from EC1 pL region"<br>/label="EC1 pL region" |
| mRNA | complement(4051)<br>/note="mRNA-pl (alt.; via t12a terminator)"<br>/label="pL1 mRNA start" |
| Variation | 4052 . . . 4184<br>/note="imm434 region" |
| Promoter | complement(4058 . . . 4063)<br>/label="pL1 -10" |
| operator | complement(4060 . . . 4076)<br>/note="operator-11 (first base on comp strand)"<br>/label=OL1 |
| Primer | complement(4075 . . . 4092)<br>/label=pLseq |
| Promoter | complement(4081 . . . 4086)<br>/label="pL1 -35" |
| operator | complement(4084 . . . 4100)<br>/note="operator-12 (first base on comp strand)"<br>/label=OL2 |
| mRNA | complement(4093)<br>/label="pL2 mRNA start" |
| Promoter | complement(4100 . . . 4105)<br>/label="pL2 -10" |

```
operator         complement(4104 . . . 4120)
                 /note="operator-13 (first base on comp strand)"
                 /label=OL3
Promoter         complement(4122 . . . 4127)
                 /label="pL2 -35"
Source           complement(4185 . . . 6244)
                 /label="pUC18 DNA"
Primer           complement(4350 . . . 4369)
                 /note=cagtcagtcaACATGTTCTTTCCTGCGTTA
                 /label=pLnut-F
Primer           complement(4414 . . . 4430)
                 /label=pLnutseq-F
Replication_ori  complement(4425 . . . 5013)
                 /label="Replication origin"
RNA_transcript   complement(4425 . . . 4977)
                 /label=RNAII
Promoter         4832 . . . 4836
                 /label="RNAI -35"
Promoter         4853 . . . 4858
                 /label="RNAI -10"
RNA_transcript   4867 . . . 4974
                 /label=RNAI
Promoter         complement(4988 . . . 4992)
                 /label="RNAII -10"
Promoter         complement(5008 . . . 5013)
                 /label="RNAII -35"
CDS              complement(5184 . . . 6044)
                 /label=beta-lactamase
Restriction_sit  5916 . . . 5927
                 /label="EcoK site"
Signal_peptide   complement(5976 . . . 6044)
                 /label=beta-lactamase
Promoter         complement(6088 . . . 6093)
                 /label="beta-lactamase -10"
Promoter         complement(6109 . . . 6114)
                 /label="beta-lactamase -35"
```

ORIGIN

```
   1  TCGCGCGTTT CGGTGATGAC GGTGAAAACC TCTGACACAT GCAGCTCCCG GAGACGGTCA
  61  CAGCTTGTCT GTAAGCGGAT GCCGGGAGCA GACAAGCCCG TCAGGGCGCG TCAGCGGGTG
 121  TTGGCGGGTG TCGGGGCTGG CTTAACTATG CGGCATCAGA GCAGATTGTA CTGAGAGTGC
 181  ACCATATATG CGGTGTGAAA TACCGCACAG ATGCGTAAGG AGAAAATACC GCATCAGGCG
 241  CCTCCTCAAC CTGTATATTC GTAAACCACG CCCAATGGGA GCTGTCTCAG GTTTGTTCCT
 301  GATTGGTTAC GGCGCGTTTC GCATCATTGT TGAGTTTTTC CGCCAGCCCG ACGCGCAGTT
 361  TACCGGTGCC TGGGTGCAGT ACATCAGCAT GGGGCAAATT CTTTCCATCC CGATGATTGT
 421  CGCGGGTGTG ATCATGATGG TCTGGGCATA TCGTCGCAGC CCACAGCAAC ACGTTTCCTG
 481  AGGAACCATG AAACAGTATT TAGAACTGAT GCAAAAAGTG CTCGACGAAG GCACACAGAA
 541  AAACGACCGT ACCGGAACCG GAACGCTTTC CATTTTTGGT CATCAGATGC GTTTTAACCT
 601  GCAAGATGGA TTCCCGCTGG TGACAACTAA ACGTTGCCAC CTGCGTTCCA TCATCCATGA
 661  ACTGCTGTGG TTTCTGCAGG GCGACACTAA CATTGCTTAT CTACACGAAA ACAATGTCAC
 721  CATCTGGGAC GAATGGGCCG ATGAAAACGG CGACCTCGGG CCAGTGTATG GTAAACAGTG
 781  GCGCGCCTGG CCAACGCCAG ATGGTCGTCA TATTGACCAG ATCACTACGG TACTGAACCA
 841  GCTGAAAAAC GACCCGGATT CGCCGCGCAT TATTGTTTCA GCGTGGAACG TAGGCGAACT
 901  GGATAAAATG GCGCTGGCAC CGTGCCATGC ATTCTTCCAG TTCTATGTGG CAGACGGCAA
 961  ACTCTCTTGC CAGCTTTATC AGCGCTCCTG TGACGTCTTC CTCGGCCTGC CGTTCAACAT
1021  TGCCAGCTAC GCGTTATTGG TGCATATGAT GGCGCAGCAG TGCGATCTGG AAGTGGGTGA
1081  TTTTGTCTGG ACCGGTGGCG ACACGCATCT GTACAGCAAC CATATGGATC AAACTCATCT
1141  GCAATTAAGC CGCGAACCGC GTCCGCTGCC GAAGTTGATT ATCAAACGTA AACCCGAATC
```

-continued

```
1201  CATCTTCGAC TACCGTTTCG AAGACTTTGA GATTGAAGGC TACGATCCGC ATCCGGGCAT
1261  TAAAGCGCCG GTGGCTATCT AATTACGAAA CATCCTGCCA GAGCCGACGC CAGTGTGCGT
1321  CGGTTTTTTT ACCCTCCGTT AAATTCTTCG AGACGCCTTC CCGAAGGCGC CATTCGCCAT
1381  TCAGGCTGCG CAACTGTTGG GAAGGGCGAT CGGTGCGGGC CTCTTCGCTA TTACGCCAGC
1441  TGGCGAAAGG GGGATGTGCT GCAAGGCGAT TAAGTTGGGT AACGCCAGGG TTTTCCCAGT
1501  CACGACGTTG TAAAACGACG GCCAGTGCCA AGCTTTCTTT AATGAAGCAG GGCATCAGGA
1561  CGGTATCTTT GTGGAGAAAG CAGAGTAATC TTATTCAGCC TGACTGGTGG GAAACCACCA
1621  GTCAGAATGT GTTAGCGCAT GTTGACAAAA ATACCATTAG TCACATTATC CGTCAGTCGG
1681  ACGACATGGT AGATAACCTG TTTATTATGC GTTTTGATCT TACGTTTAAT ATTACCTTTA
1741  TGCGATGAAA CGGTCTTGGC TTTGATATTC ATTTGGTCAG AGATTTGAAT GGTTCCCTGA
1801  CCTGCCATCC ACATTCGCAA CATACTCGAT TCGGTTCGGC TCAATGATAA CGTCGGCATA
1861  TTTAAAAACG AGGTTATCGT TGTCTCTTTT TTCAGAATAT CGCCAAGGAT ATCGTCGAGA
1921  GATTCCGGTT TAATCGATTT AGAACTGATC AATAAATTTT TTCTGACCAA TAGATATTCA
1981  TCAAAATGAA CATTGGCAAT TGCCATAAAA ACGATAAATA ACGTATTGGG ATGTTGATTA
2041  ATGATGAGCT TGATACGCTG ACTGTTAGAA GCATCGTGGA TGAAACAGTC CTCATTAATA
2101  AACACCACTG AAGGGCGCTG TGAATCACAA GCTATGGCAA GGTCATCAAC GGTTTCAATG
2161  TCGTTGATTT CTCTTTTTTT AACCCCTCTA CTCAACAGAT ACCCGGTTAA ACCTAGTCGG
2221  GTGTAACTAC ATAAATCCAT AATAATCGTT GACATGGCAT ACCCTCACTC AATGCGTAAC
2281  GATAATTCCC CTTACCTGAA TATTTCATCA TGACTAAACG GAACAACATG GGTCACCTAA
2341  TGCGCCACTC TCGCGATTTT TCAGGCGGAC TTACTATCCC GTAAAGTGTT GTATAATTTG
2401  CCTGGAATTG TCTTAAAGTA AAGTAAATGT TGCGATATGT GAGTGAGCTT AAAACAAATA
2461  TTTCGCTGCA GGAGTATCCT GGAAGATGTT CGTAGaagct tACTGCTCAC AAGAAAAAAG
2521  GCACGTCATC TGACGTGCCT TTTTTATTTG TACTACCCTG TACGATTACT GCAGCTCGAG
2581  TTTAattcaa atcttcttca gaaatcaatt tttgttcAGC GTTATACTTT TGGGATTTTA
2641  CCTCAAAATG GGATTCTATT TCACCCACT CCTTACAAAG GATATTCTCA TGCCCAAAAA
2701  GCCAGTGTTT GGGGCCAATA ATGATTTTTT CTGGATTTTC TATCAAATAG GCCGCCCACC
2761  AGCTATAAGT GCTATTAGCG ATAATGCCAT GCTGACAAGA TTGCATGAGC AGCATGTCCC
2821  AATACGCCTC TTCTTCTTTA TCCCTAGTGG TCATGTCCAT AAAAGGGTAG CCAAGATCAA
2881  GATTTTGCGT GAATTCTAAG TCTTCGCAAA ACACAAAAAG CTCCATGTTT GGCACGCGCT
2941  TTGCCATATA CTCAAGCGCC TTTTTTTGAT AGTCAATACC AAGCTGACAG CCAATCCCCA
3001  CATAATCCCC TCTTCTTATA TGCACAAACA CGCTGTTTTT AGCGGCTAAA ATCAAAGAAA
3061  GCTTGCACTG ATATTCTTCC TCTTTTTTAT TATTATTCTT ATTATTTTCG GGtGGtGGtG
3121  GTAGAGTGAA GGTTTGCTTG ATTAAAGGGG ATATAGCATC AAAGTATCGT GGATCTTGGA
3181  AATAGCCAAA AAAATAAGTC AAGCGGCTTG GCTTTAGCAA TTTAGGCTCG TATTCAAAAA
3241  CGATTTCTTG ACTCACCCTA TCAAATCCCA TGCATTTGAG CGCGTCTCTT ACTAGCTTGG
3301  GGAGGTGTTG CATTTTAGCT ATAGCGATTT CTTTCGCGCT CGCATAGGGC AAATCAATAG
3361  GGAAAAGTTC TAATTGCATT TTCCTATCGC TCCAATCAAA AGAAGTGATA TCTAACAGCA
3421  CAGGCGTATT AGAGTGTTTT TGCAAACTTT TAGCGAAAGC GTATTGAAAC ATTTGATTCC
3481  CAAGCCCTCC GCAAATTTGC ACCACCTTAA AAGCCATATG tatatctcct tcttgaaTTC
3541  TAAaAATTGA TTGAATGTAT GCAAATAAAT GCATACACCA TAGGTGTGGT TTAATTTGAT
```

```
3601  GCCCTTTTTC AGGGCTGGAA TGTGTAAGAG CGGGGTTATT TATGCTGTTG TTTTTTTGTT
3661  ACTCGGGAAG GGCTTTACCT CTTCCGCATA AACGCTTCCA TCAGCGTTTA TAGTTAAAAA
3721  AATCTTTCGG AACTGGTTTT GCGCTTACCC CAACCAACAG GGGATTTGCT GCTTTCCATT
3781  GAGCCTGTTT CTCTGCGCGA CGTTCGCGGC GGCGTGTTTG TGCATCCATC TGGATTCTCC
3841  TGTCAGTTAG CTTTGGTGGT GTGTGGCAGT TGTAGTCCTG AACGAAAACC CCCCGCGATT
3901  GGCACATTGG CAGCTAATCC GGAATCGCAC TTACGGCCAA TGCTTCGTTT CGTATCACAC
3961  ACCCCAAAGC CTTCTGCTTT GAATGCTGCC CTTCTTCAGG GCTTAATTTT TAAGAGCGTC
4021  ACCTTCATGG TGGTCAGTGC GTCCTGCTGA TGTGCTCAGT ATCACCGCCA GTGGTATTTA
4081  TGTCAACACC GCCAGAGATA ATTTATCACC GCAGATGGTT ATCTGTATGT TTTTTATATG
4141  AATTTATTTT TTGCAGGGGG GCATTGTTTG GTAGGTGAGA GATCAATTCT GCATTAATGA
4201  ATCGGCCAAC GCGCGGGGAG AGGCGGTTTG CGTATTGGGC GCTCTTCCGC TTCCTCGCTC
4261  ACTGACTCGC TGCGCTCGGT CGTTCGGCTG CGGCGAGCGG TATCAGCTCA CTCAAAGGCG
4321  GTAATACGGT TATCCACAGA ATCAGGGGAT AACGCAGGAA AGAACATGTG AGCAAAAGGC
4381  CAGCAAAAGG CCAGGAACCG TAAAAAGGCC GCGTTGCTGG CGTTTTTCCA TAGGCTCCGC
4441  CCCCCTGACG AGCATCACAA AAATCGACGC TCAAGTCAGA GGTGGCGAAA CCCGACAGGA
4501  CTATAAAGAT ACCAGGCGTT TCCCCCTGGA AGCTCCCTCG TGCGCTCTCC TGTTCCGACC
4561  CTGCCGCTTA CCGGATACCT GTCCGCCTTT CTCCCTTCGG GAAGCGTGGC GCTTTCTCAT
4621  AGCTCACGCT GTAGGTATCT CAGTTCGGTG TAGGTCGTTC GCTCCAAGCT GGGCTGTGTG
4681  CACGAACCCC CCGTTCAGCC CGACCGCTGC GCCTTATCCG GTAACTATCG TCTTGAGTCC
4741  AACCCGGTAA GACACGACTT ATCGCCACTG GCAGCAGCCA CTGGTAACAG GATTAGCAGA
4801  GCGAGGTATG TAGGCGGTGC TACAGAGTTC TTGAAGTGGT GGCCTAACTA CGGCTACACT
4861  AGAAGGACAG TATTTGGTAT CTGCGCTCTG CTGAAGCCAG TTACCTTCGG AAAAAGAGTT
4921  GGTAGCTCTT GATCCGGCAA ACAAACCACC GCTGGTAGCG GTGGTTTTTT TGTTTGCAAG
4981  CAGCAGATTA CGCGCAGAAA AAAAGGATCT CAAGAAGATC CTTTGATCTT TTCTACGGGG
5041  TCTGACGCTC AGTGGAACGA AAACTCACGT TAAGGGATTT TGGTCATGAG ATTATCAAAA
5101  AGGATCTTCA CCTAGATCCT TTTAAATTAA AAATGAAGTT TTAAATCAAT CTAAAGTATA
5161  TATGAGTAAA CTTGGTCTGA CAGTTACCAA TGCTTAATCA GTGAGGCACC TATCTCAGCG
5221  ATCTGTCTAT TTCGTTCATC CATAGTTGCC TGACTCCCCG TCGTGTAGAT AACTACGATA
5281  CGGGAGGGCT TACCATCTGG CCCCAGTGCT GCAATGATAC CGCGAGACCC ACGCTCACCG
5341  GCTCCAGATT TATCAGCAAT AAACCAGCCA GCCGGAAGGG CCGAGCGCAG AAGTGGTCCT
5401  GCAACTTTAT CCGCCTCCAT CCAGTCTATT AATTGTTGCC GGGAAGCTAG AGTAAGTAGT
5461  TCGCCAGTTA ATAGTTTGCG CAACGTTGTT GCCATTGCTA CAGGCATCGT GGTGTCACGC
5521  TCGTCGTTTG GTATGGCTTC ATTCAGCTCC GGTTCCCAAC GATCAAGGCG AGTTACATGA
5581  TCCCCCATGT TGTGCAAAAA AGCGGTTAGC TCCTTCGGTC CTCCGATCGT TGTCAGAAGT
5641  AAGTTGGCCG CAGTGTTATC ACTCATGGTT ATGGCAGCAC TGCATAATTC TCTTACTGTC
5701  ATGCCATCCG TAAGATGCTT TTCTGTGACT GGTGAGTACT CAACCAAGTC ATTCTGAGAA
5761  TAGTGTATGC GGCGACCGAG TTGCTCTTGC CCGGCGTCAA TACGGGATAA TACCGCGCCA
5821  CATAGCAGAA CTTTAAAAGT GCTCATCATT GGAAAACGTT CTTCGGGGCG AAAACTCTCA
5881  AGGATCTTAC CGCTGTTGAG ATCCAGTTCG ATGTAACCCA CTCGTGCACC CAACTGATCT
```

-continued

```
5941  TCAGCATCTT TTACTTTCAC CAGCGTTTCT GGGTGAGCAA AAACAGGAAG GCAAAATGCC

6001  GCAAAAAAGG AATAAGGGC GACACGGAAA TGTTGAATAC TCATACTCTT CCTTTTTCAA

6061  TATTATTGAA GCATTTATCA GGGTTATTGT CTCATGAGCG GATACATATT TGAATGTATT

6121  TAGAAAAATA AACAAATAGG GGTTCCGCGC ACATTTCCCC GAAAAGTGCC ACCTGACGTC

6181  TAAGAAACCA TTATTATCAT GACATTAACC TATAAAAATA GGCGTATCAC GAGGCCCTTT

6241  CGTC (SEQ ID NO: 1; plasmid G171)
```

The nucleic acid construct further comprises an α (1,2) fucosyltransferase gene comprising, e.g., at least 10% and less than 40% identity at the amino acid level to Helicobacter pylori 26695 alpha-(1,2) fucosyltransferase (futC). For example, the exogenous α (1,2) fucosyltransferase gene is selected from the group consisting of Helicobacter pylori 26695 alpha-(1,2) fucosyltransferase (futC), Vibrio cholera O22 wblA, Escherichia coli O126 wbgL, Helicobacter bilis ATCC 437879 futD, Helicobacter cinaedi CCUG 18818 alpha-1,2-fucosyltransferase (futE), Helicobacter mustelae 12198 (ATCC 43772) alpha-1,2-fucosyltransferase (futL), Bacteroides vulgatus ATCC 8482 glycosyl transferase family protein (futN), Bacteroides ovatus ATCC 8483 futO, Escherichia coli O55:H7 (str. CB9615) fucosyltransferase (wbgN), Bacteroides fragilis (NCTC) 9343 alpha-1,2-fucosyltransferase (bft1), and Bacteroides fragilis (NCTC) 9343 fucosyl transferase (bft3/wcfB). The depiction of pG171 bears the alpha 1,2 FT gene futC to serve as an example.

Also within the invention is an isolated E. coli bacterium as described above and characterized as comprising a reduced level of β-galactosidase activity, a defective colanic acid synthesis pathway, a mutation in the lacA gene, a mutation in an ATP-dependant intracellular protease, and a mutation in a thyA gene. The invention also provides methods of identifying an α (1,2) fucosyltransferase gene capable of synthesizing 2'-fucosyllactose (2'-FL) in E. coli. The method of identifying non-FutC lactose-utilizing, α(1,2)fucosyltransferase enzyme comprises the following steps:

1) performing a computational search of sequence databases to define a broad group of simple sequence homologs of any known, lactose-utilizing α(1,2)fucosyltransferase;

2) using the list from step (1), deriving a search profile containing common sequence and/or structural motifs shared by the members of the list;

3) searching sequence databases, using a derived search profile based on the common sequence or structural motif from step (2) as query, and identifying a candidate sequences, wherein a sequence homology to a reference lactose-utilizing α(1,2)fucosyltransferase is 40% or less;

4) compiling a list of candidate organisms, said organisms being characterized as expressing α(1,2)fucosyl-glycans in a naturally-occurring state;

5) selecting candidate sequences that are derived from candidate organisms to generate a list of candidate lactose-utilizing enzymes;

6) expressing the candidate lactose-utilizing enzyme in a host organism; and 7) testing for lactose-utilizing α(1,2)fucosyltransferase activity, wherein detection of 2'-FL in said organism indicates that the candidate sequence comprises a non-FutC lactose-utilizing α(1,2)fucosyltransferase. For example, the sequence homology to a reference lactose-utilizing α(1,2) fucosyltransferase is 40% or less.

A purified fucosylated oligosaccharide produced by the methods described above is also within the invention. The purified oligosaccharide (2'-FL) obtained at the end of the process is a white/slightly off-white, crystalline, sweet powder. Unlike oligosaccharide production methods using FutC, the methods utilizing certain non-FutC enzymes (e.g. FutL) do not possess α (1,3) fucosyltransferase activity which leads to side reactions. The lack of α (1,3) fucosyltransferase activity associated with FutL contributes to its efficiency in producing 2'FL and is an advantage compared to FutC. FutL does not possess alpha 1,3 fucosyltransferase activity. For example, an engineered E. coli cell, E. coli culture supernatant, or E. coli cell lysate according to the invention comprises recombinant 2'-FL and does not substantially comprise a 1,3 fucosylated lactose prior to purification of 2'-FL from the cell, culture supernatant, or lysate. Both FutN and WbgL appear to have alpha 1,3 fucosyltransferase activity (similar to FutC). However as a general matter, the fucosylated oligosaccharide produced by the methods contains a negligible amount of 3-FL in a 2'-FL-containing cell, cell lysate or culture, or supernatant, e.g., less than 1% of the level of 2'-FL or 0.5% of the level of 2'-FL.

A purified oligosaccharide, e.g., 2'-FL or LDFT, is one that is at least 90%, 95%, 98%, 99%, or 100% (w/w) of the desired oligosaccharide by weight. Purity is assessed by any known method, e.g., thin layer chromatography or other chromatographic techniques known in the art. The invention includes a method of purifying a fucosylated oligosaccharide produced by the genetically engineered bacterium described above, which method comprises separating the desired fucosylated oligosaccharide (e.g., 2'-FL) from contaminants in a bacterial cell lysate or bacterial cell culture supernatant of the bacterium.

The oligosaccharides are purified and used in a number of products for consumption by humans as well as animals, such as companion animals (dogs, cats) as well as livestock (bovine, equine, ovine, caprine, or porcine animals, as well as poultry). For example, a pharmaceutical composition comprises purified 2'-FL and a pharmaceutically-acceptable excipient that is suitable for oral administration. Large quantities of 2'-FL are produced in bacterial hosts, e.g., an E. coli bacterium comprising an exogenous α (1,2) fucosyltransferase gene.

An E. coli bacterium comprising an enhanced cytoplasmic pool of lactose and GDP-fucose is useful in such production systems. Endogenous E. coli metabolic pathways and genes are manipulated in ways that result in the generation of increased cytoplasmic concentrations of lactose and/or GDP-fucose, as compared to levels found in wild type E. coli. For example, the bacteria contain at least 10%, 20%, 50%, or 2×, 5×, 10× or more of the levels compared to a corresponding wild type bacteria that lacks the genetic modifications described above.

A method of producing a pharmaceutical composition comprising a purified human milk oligosaccharide (HMOS) is carried out by culturing the bacterium described above, purifying the HMOS produced by the bacterium, and combining the HMOS with an excipient or carrier to yield a dietary supplement for oral administration. These compositions are useful in methods of preventing or treating enteric and/or respiratory diseases in infants and adults. Accordingly, the compositions are administered to a subject suffering from or at risk of developing such a disease.

The invention also provides methods for increasing the intracellular concentration of lactose in E. coli, for cells grown in the presence of lactose, by using manipulations of endogenous E. coli genes involved in lactose import, export, and catabolism. In particular, described herein are methods of increasing intracellular lactose levels in E. coli genetically engineered to produce a human milk oligosaccharide by simultaneous deletion of the endogenous β-galactosidase gene (lacZ) and the lactose operon repressor gene (lacI). During construction of this deletion, the lacIq promoter is placed immediately upstream of (contiguous with) the lactose permease gene, lacY, i.e., the sequence of the lacIq promoter is directly upstream and adjacent to the start of the sequence encoding the lacY gene, such that the lacY gene is under transcriptional regulation by the lacIq promoter. The modified strain maintains its ability to transport lactose from the culture medium (via LacY), but is deleted for the wild-type chromosomal copy of the lacZ (encoding β-galactosidase) gene responsible for lactose catabolism. Thus, an intracellular lactose pool is created when the modified strain is cultured in the presence of exogenous lactose. Another method for increasing the intracellular concentration of lactose in E. coli involves deletion of the lacA gene. The lacA mutation prevents the formation of intracellular acetyl-lactose, which not only removes this molecule as a contaminant from subsequent purifications, but also eliminates E. coli's ability to export excess lactose from its cytoplasm (Danchin A. Cells need safety valves. Bioessays 2009, July; 31(7):769-73.), thus greatly facilitating purposeful manipulations of the E. coli intracellular lactose pool.

The invention also provides methods for increasing intracellular levels of GDP-fucose in Escherichia coli by manipulating the organism's endogenous colanic acid biosynthesis pathway. This increase is achieved through a number of genetic modifications of endogenous E. coli genes involved either directly in colanic acid precursor biosynthesis, or in overall control of the colanic acid synthetic regulon. In particular, described herein are methods of increasing intracellular GDP-fucose levels in E. coli genetically engineered to produce a human milk oligosaccharide by deletion of the wcaJ gene, encoding the UDP-glucose lipid carrier transferase. In a wcaJ null background, GDP-fucose accumulates in the E. coli cytoplasm.

In one aspect, the human milk oligosaccharide produced by engineered bacteria comprising an exogenous nucleic acid molecule encoding an α(1,2) fucosyltransferase is 2'-FL (2'-fucosyllactose). Preferably the α (1,2) fucosyltransferase utilized is any α (1,2) fucosyltransferase capable of using lactose as the sugar acceptor substrate for 2'-FL synthesis. Preferably, the exogenous α (1,2) fucosyltransferase gene comprises at least 10% identity at the amino acid level and less than about 40% to Helicobacter pylori 26695 alpha-(1,2) fucosyltransferase (FutC).

The invention also provides compositions comprising E. coli genetically engineered to produce the human milk tetrasaccharide lactodifucotetraose (LDFT). The E. coli in this instance comprise an exogenous nucleic acid molecule encoding an α (1,2) fucosyltransferase that also possesses α (1,3) fucosyltransferase activity.

The invention provides a method of treating, preventing, or reducing the risk of infection in a subject comprising administering to said subject a composition comprising a purified recombinant human milk oligosaccharide, wherein the HMOS binds to a pathogen and wherein the subject is infected with or at risk of infection with the pathogen. In one aspect, the infection is caused by a Norwalk-like virus or Campylobacter jejuni. The subject is preferably a mammal in need of such treatment. The mammal is, e.g., any mammal, e.g., a human, a primate, a mouse, a rat, a dog, a cat, a cow, a horse, or a pig. In a preferred embodiment, the mammal is a human. For example, the compositions are formulated into animal feed (e.g., pellets, kibble, mash) or animal food supplements for companion animals, e.g., dogs or cats, as well as livestock or animals grown for food consumption, e.g., cattle, sheep, pigs, chickens, and goats. Preferably, the purified HMOS is formulated into a powder (e.g., infant formula powder or adult nutritional supplement powder, each of which is mixed with a liquid such as water or juice prior to consumption) or in the form of tablets, capsules or pastes or is incorporated as a component in dairy products such as milk, cream, cheese, yogurt or kefir, or as a component in any beverage, or combined in a preparation containing live microbial cultures intended to serve as probiotics, or in prebiotic preparations to enhance the growth of beneficial microorganisms either in vitro or in vivo.

Polynucleotides, polypeptides, and oligosaccharides of the invention are purified and/or isolated. Purified defines a degree of sterility that is safe for administration to a human subject, e.g., lacking infectious or toxic agents. Specifically, as used herein, an "isolated" or "purified" nucleic acid molecule, polynucleotide, polypeptide, protein or oligosaccharide, is substantially free of other cellular material, or culture medium when produced by recombinant techniques, or chemical precursors or other chemicals when chemically synthesized. For example, purified HMOS compositions are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, thin layer chromatography, or high-performance liquid chromatography (HPLC) analysis. For example, a "purified protein" refers to a protein that has been separated from other proteins, lipids, and nucleic acids with which it is naturally associated. Preferably, the protein constitutes at least 10, 20, 50, 70, 80, 90, 95, 99-100% by dry weight of the purified preparation.

Similarly, by "substantially pure" is meant an oligosaccharide that has been separated from the components that naturally accompany it. Typically, the oligosaccharide is substantially pure when it is at least 60%, 70%, 80%, 90%, 95%, or even 99%, by weight, free from the proteins and naturally-occurring organic molecules with which it is naturally associated.

By "isolated nucleic acid" is meant a nucleic acid that is free of the genes which, in the naturally-occurring genome of the organism from which the DNA of the invention is derived, flank the gene. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones.

A "heterologous promoter" is a promoter which is different from the promoter to which a gene or nucleic acid sequence is operably linked in nature.

The term "overexpress" or "overexpression" refers to a situation in which more factor is expressed by a genetically-altered cell than would be, under the same conditions, by a wild type cell. Similarly, if an unaltered cell does not express a factor that it is genetically altered to produce, the term "express" (as distinguished from "overexpress") is used indicating the wild type cell did not express the factor at all prior to genetic manipulation.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

By the terms "effective amount" and "therapeutically effective amount" of a formulation or formulation component is meant a nontoxic but sufficient amount of the formulation or component to provide the desired effect.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The host organism used to express the non-FutC lactose-accepting fucosyltransferase gene product is typically the enterobacterium *Escherichia coli* K12 (*E. coli*). *E. coli* K-12 is not considered a human or animal pathogen nor is it toxicogenic. *E. coli* K-12 is a standard production strain of bacteria and is noted for its safety due to its poor ability to colonize the colon and establish infections (see, e.g., epa.gov/oppt/biotech/pubs/fra/fra004.htm). However, a variety of bacterial species may be used in the oligosaccharide biosynthesis methods, e.g., *Erwinia herbicola* (*Pantoea agglomerans*), *Citrobacter freundii*, *Pantoea citrea*, *Pectobacterium carotovorum*, or *Xanthomonas campestris*. Bacteria of the genus *Bacillus* may also be used, including *Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacillus cereus,* and *Bacillus circulans*. Similarly, bacteria of the genera *Lactobacillus* and *Lactococcus* may be modified using the methods of this invention, including but not limited to *Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii,* and *Lactococcus lactis. Streptococcus thermophiles* and *Proprionibacterium freudenreichii* are also suitable bacterial species for the invention described herein. Also included as part of this invention are strains, modified as described here, from the genera *Enterococcus* (e.g., *Enterococcus faecium* and *Enterococcus thermophiles*), *Bifidobacterium* (e.g., *Bifidobacterium longum, Bifidobacterium infantis,* and *Bifidobacterium bifidum*), *Sporolactobacillus* spp., *Micromomospora* spp., *Micrococcus* spp., *Rhodococcus* spp., and *Pseudomonas* (e.g., *Pseudomonas fluorescens* and *Pseudomonas aeruginosa*). Bacteria comprising the characteristics described herein are cultured in the presence of lactose, and a fucosylated oligosaccharide is retrieved, either from the bacterium itself or from a culture supernatant of the bacterium. The fucosylated oligosaccharide is purified for use in therapeutic or nutritional products, or the bacteria are used directly in such products.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIGS. 3A-C is a series of photographs showing thin layer chromatography analysis of 2'-FL produced in *E. coli* strains by candidate α (1,2) fucosyltransferases. FIG. 3A shows significant production of 2'-FL by WbgL. FIG. 3B shows significant production of 2'-FL by FutL. FIG. 3C shows significant production of 2'-FL by FutN.

FIG. 6 is a diagram of a $P_{lacIq}$ lacY$^+$ chromosomal construct.

FIG. 7 is a diagram of the chromosomal deletion of wcaJ.

FIG. 8 is a diagram of the kan, lacZ$^+$ insertion into the lon locus.

DETAILED DESCRIPTION OF THE INVENTION

Figure 1:
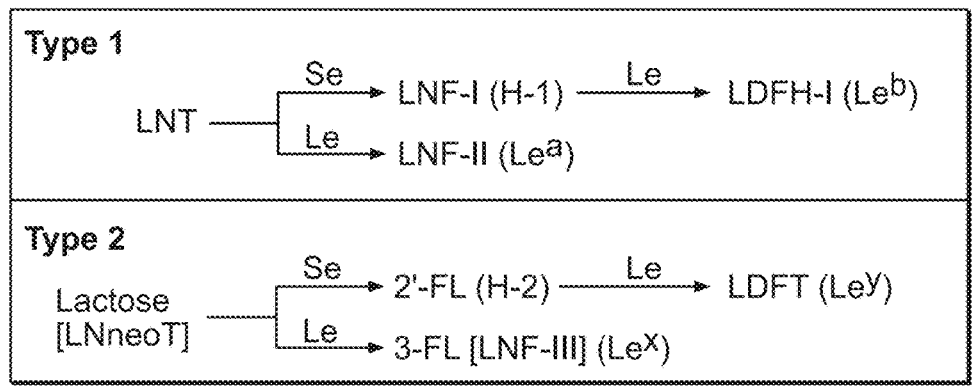
FIG. 1 is a schematic illustration showing the synthetic pathway of the fucosyl oligosaccharides of human milk. Se and Le indicate synthesis by fucosyltransferases of the secretor and Lewis genes, respectively. The abbreviated biochemical name [with alternate biochemical structure in brackets] is given (histo-blood group antigen analog in parentheses).

While some studies suggest that human milk glycans could be used as antimicrobial anti-adhesion agents, the difficulty and expense of producing adequate quantities of these agents of a quality suitable for human consumption has limited their full-scale testing and perceived utility. What has been needed is a suitable method for producing the appropriate glycans in sufficient quantities at reasonable cost. Prior to the invention described herein, there were attempts to use several distinct synthetic approaches for glycan synthesis. Some chemical approaches can synthesize oligosaccharides (Flowers, H. M. Methods Enzymol 50, 93-121 (1978); Seeberger, P. H. Chem Commun (Camb) 1115-1121 (2003)), but reactants for these methods are expensive and potentially toxic (Koeller, K. M. & Wong, C. H. Chem Rev 100, 4465-4494 (2000)). Enzymes expressed from engineered organisms (Albermann, C., Piepersberg, W. & Wehmeier, U. F. Carbohydr Res 334, 97-103 (2001); Bettler, E., Samain, E., Chazalet, V., Bosso, C., et al. Glycoconj J 16, 205-212 (1999); Johnson, K. F. Glycoconj J 16, 141-146 (1999); Palcic, M. M. Curr Opin Biotechnol 10, 616-624 (1999); Wymer, N. & Toone, E. J. Curr Opin Chem Biol 4, 110-119 (2000)) provide a precise and efficient synthesis (Palcic, M. M. Curr Opin Biotechnol 10, 616-624 (1999)); Crout, D. H. & Vic, G. Curr Opin Chem Biol 2, 98-111 (1998)), but the high cost of the reactants, especially the sugar nucleotides, limits their utility for low-cost, large-scale production. Microbes have been genetically engineered to express the glycosyltransferases needed to synthesize oligosaccharides from the bacteria's innate pool of nucleotide sugars (Endo, T., Koizumi, S., Tabata, K., Kakita, S. & Ozaki, A. Carbohydr Res 330, 439-443 (2001); Endo, T., Koizumi, S., Tabata, K. & Ozaki, A. Appl Microbiol Biotechnol 53, 257-261 (2000); Endo, T. & Koizumi, S. Curr Opin Struct Biol 10, 536-541 (2000); Endo, T., Koizumi, S., Tabata, K., Kakita, S. & Ozaki, A. Carbohydr Res 316, 179-183 (1999); Koizumi, S., Endo, T., Tabata, K. & Ozaki, A. Nat Biotechnol 16, 847-850 (1998)). However, prior to the invention described herein, there was a growing need to identify and characterize additional glycosyltransferases that are useful for the synthesis of HMOS in metabolically engineered bacterial hosts.

Not all α(1,2)fucosyltransferases can utilize lactose as an acceptor sugar. A desired enzyme utilizes GDP-fucose as a donor, and lactose is the acceptor for that donor. A method of identifying novel α(1,2)fucosyltransferase enzymes capable of utilizing lactose as an acceptor was carried out using the following steps: 1) performing a computational search of sequence databases to define a broad group of simple sequence homologs of any known, lactose-utilizing α(1,2)fucosyltransferase; 2) using the list of homologs from step 1 to derive a search profile containing common sequence and/or structural motifs shared by the members of the broad group, e.g. by using computer programs such as MEME (Multiple Em for Motif Elicitation available at http://meme.sdsc.edu/meme/cgi-bin/meme.cgi) or PSI-BLAST (Position-Specific Iterated BLAST available at ncbi.nlm.nih.gov/blast with additional information at cnx.org/content/m11040/latest/); 3) searching sequence databases (e.g., using computer programs such as PSI-BLAST, or MAST (Motif Alignment Search Tool available at http://meme.sdsc.edu/meme/cgi-bin/mast.cgi); using this derived search profile as query, and identifying "candidate sequences" whose simple sequence homology to the original lactose-accepting α(1,2)fucosyltransferase is 40% or less; 4) scanning the scientific literature and developing a list of "candidate organisms" known to express α(1,2)fucosyl-glycans; 5) selecting only those "candidate sequences" that are derived from "candidate organisms" to generate a list of "candidate lactose-utilizing enzymes"; and 6) expressing each "candidate lactose-utilizing enzyme" and testing for lactose-utilizing α(1,2)fucosyltransferase activity.

The MEME suite of sequence analysis tools (meme.sdsc.edu/meme/cgi-bin/meme.cgi) can also be used as an alternative to PSI-BLAST. Sequence motifs are discovered using the program "MEME". These motifs can then be used to search sequence databases using the program "MAST". The BLAST and PHI-BLAST search algorithms are other well known alternatives.

To test for lactose-utilizing activity, the production of 2'-FL is evaluated in a host organism that expresses the candidate enzyme and which contains both cytoplasmic GDP-fucose and lactose pools. The production of 2'-FL indicates that the candidate enzyme-encoding sequence functions as a lactose-utilizing α(1,2)fucosyltransferase.

To find enzymes with similarity to FutC, entire amino acid of FutC was used as a query in PSI-BLAST. The results of the lactose-utilizing α(1,2)fucosyltransferase identification method of this invention are surprising, because the % identity of several of the lactose-utilizing α(1,2)fucosyltransferases identified are less than 40% of the reference FutC sequence. Another most surprising aspect of the study is that 8 of the 10 candidates tested were able to utilize lactose as an acceptor, 3 of which did so at levels very close to the "gold-standard" enzyme FutC. This was a higher "hit rate" was anticipated. While 6 out of 10 of the candidate enzymes are found in bacteria that incorporate α(1,2)fucose into their LPS structure, the oligosaccharides to which the fucose is attached are very different than the lactose each candidate enzyme is being asked to utilize in the query. Moreover, it was surprising that both WblA and WbgN could utilize lactose as an acceptor, because both of these enzymes are found in bacteria that do not incorporate fucose into their LPS structure. Rather, they utilize a related sugar called colitose.

Human Milk Glycans

Human milk contains a diverse and abundant set of neutral and acidic oligosaccharides (Kunz, C., Rudloff, S., Baier, W., Klein, N., and Strobel, S. (2000). Annu Rev Nutr 20, 699-722; Bode, L. (2006). J Nutr 136, 2127-130). More than 130 different complex oligosaccharides have been identified in human milk, and their structural diversity and abundance is unique to humans. Although these molecules may not be utilized directly by infants for nutrition, they nevertheless serve critical roles in the establishment of a healthy gut microbiome (Marcobal, A., Barboza, M., Froehlich, J. W., Block, D. E., et al. J Agric Food Chem 58, 5334-5340 (2010)), in the prevention of disease (Newburg, D. S., Ruiz-Palacios, G. M. & Morrow, A. L. Annu Rev Nutr 25, 37-58 (2005)), and in immune function (Newburg, D. S.

& Walker, W. A. Pediatr Res 61, 2-8 (2007)). Despite millions of years of exposure to human milk oligosaccharides (HMOS), pathogens have yet to develop ways to circumvent the ability of HMOS to prevent adhesion to target cells and to inhibit infection. The ability to utilize HMOS as pathogen adherence inhibitors promises to address the current crisis of burgeoning antibiotic resistance. Human milk oligosaccharides produced by biosynthesis represent the lead compounds of a novel class of therapeutics against some of the most intractable scourges of society.

One alternative strategy for efficient, industrial-scale synthesis of HMOS is the metabolic engineering of bacteria. This approach involves the construction of microbial strains overexpressing heterologous glycosyltransferases, membrane transporters for the import of precursor sugars into the bacterial cytosol, and possessing enhanced pools of regenerating nucleotide sugars for use as biosynthetic precursors (Dumon, C., Samain, E., and Priem, B. (2004). Biotechnol Prog 20, 412-19; Ruffing, A., and Chen, R. R. (2006). Microb Cell Fact 5, 25). A key aspect of this approach is the heterologous glycosyltransferase selected for overexpression in the microbial host. The choice of glycosyltransferase can significantly affect the final yield of the desired synthesized oligosaccharide, given that enzymes can vary greatly in terms of kinetics, substrate specificity, affinity for donor and acceptor molecules, stability and solubility. A few glycosyltransferases derived from different bacterial species have been identified and characterized in terms of their ability to catalyze the biosynthesis of HMOS in *E. coli* host strains (Dumon, C., Bosso, C., Utille, J. P., Heyraud, A., and Samain, E. (2006). Chembiochem 7, 359-365; Dumon, C., Samain, E., and Priem, B. (2004). Biotechnol Prog 20, 412-19; Li, M., Liu, X. W., Shao, J., Shen, J., Jia, Q., Yi, W., Song, J. K., Woodward, R., Chow, C. S., and Wang, P. G. (2008). Biochemistry 47, 378-387). The identification of additional glycosyltransferases with faster kinetics, greater affinity for nucleotide sugar donors and/or acceptor molecules, or greater stability within the bacterial host significantly improves the yields of therapeutically useful HMOS. Prior to the invention described herein, chemical syntheses of HMOS were possible, but were limited by stereo-specificity issues, precursor availability, product impurities, and high overall cost (Flowers, H. M. Methods Enzymol 50, 93-121 (1978); Seeberger, P. H. Chem Commun (Camb) 1115-1121 (2003); Koeller, K. M. & Wong, C. H. Chem Rev 100, 4465-4494 (2000)). The invention overcomes the shortcomings of these previous attempts by providing new strategies to inexpensively manufacture large quantities of human milk oligosaccharides (HMOS) for use as dietary supplements. Advantages include efficient expression of the enzyme, improved stability and/or solubility of the gene product (2'-FL) and reduced toxicity to the host organism. For example, α(1,2) fucosyltransferases derived from *E. coli* strains (e.g. WbgL) are more stable and are expressed at higher levels within *E. coli* production hosts strains compared to FutC. In another example, highly active fucosyltransferase (futN) is derived from a commensal microbe (*Bacteroides*) rather than a pathogen. Since many engineered production strains use fucosyltransferase genes obtained from pathogens, safety and/or increased consumer acceptance are added advantages of this sequence/enzyme.

As described in detail below, *E. coli* (or other bacteria) is engineered to produce 2'-FL in commercially viable levels. For example, yields are >5 grams/liter in a bacterial fermentation process.

Role of Human Milk Glycans in Infectious Disease

Human milk glycans, which comprise both unbound oligosaccharides and their glycoconjugates, play a significant role in the protection and development of the infant gastrointestinal (GI) tract. Neutral fucosylated oligosaccharides, including 2'-fucosyllactose (2'-FL), protect infants against several important pathogens. Milk oligosaccharides found in various mammals differ greatly, and the composition in humans is unique (Hamosh M., 2001 Pediatr Clin North Am, 48:69-86; Newburg D. S., 2001 Adv Exp Med Biol, 501:3-10). Moreover, glycan levels in human milk change throughout lactation and also vary widely among individuals (Morrow A. L. et al., 2004 J Pediatr, 145:297-303; Chaturvedi P et al., 2001 Glycobiology, 11:365-372). Approximately 200 distinct human milk oligosaccharides have been identified and combinations of simple epitopes are responsible for this diversity (Newburg D. S., 1999 Curr Med Chem, 6:117-127; Ninonuevo M. et al., 2006 J Agric Food Chem, 54:7471-74801).

Human milk oligosaccharides are composed of 5 monosaccharides: D-glucose (Glc), D-galactose (Gal), N-acetylglucosamine (GlcNAc), L-fucose (Fuc), and sialic acid (N-acetyl neuraminic acid, Neu5Ac, NANA). Human milk oligosaccharides are usually divided into two groups according to their chemical structures: neutral compounds containing Glc, Gal, GlcNAc, and Fuc, linked to a lactose (Galβ1-4Glc) core, and acidic compounds including the same sugars, and often the same core structures, plus NANA (Charlwood J. et al., 1999 Anal Biochem, 273:261-277; Martín-Sosa et al., 2003 J Dairy Sci, 86:52-59; Parkkinen J. and Finne J., 1987 Methods Enzymol, 138:289-300; Shen Z. et al., 2001 J Chromatogr A, 921:315-321).

Approximately 70-80% of oligosaccharides in human milk are fucosylated, and their synthetic pathways are believed to proceed as shown in FIG. 1 (Type I and Type II pathways begin with different precursor molecules). A smaller proportion of the oligosaccharides are sialylated or both fucosylated and sialylated, but their synthetic pathways are not fully defined. Understanding of the acidic (sialylated) oligosaccharides is limited in part by the ability to measure these compounds. Sensitive and reproducible methods for the analysis of both neutral and acidic oligosaccharides have been designed. Human milk oligosaccharides as a class survive transit through the intestine of infants very efficiently, being essentially indigestible (Chaturvedi, P., Warren, C. D., Buescher, C. R., Pickering, L. K. & Newburg, D. S. Adv Exp Med Biol 501, 315-323 (2001)).

Human Milk Glycans Inhibit Binding of Enteropathogens to their Receptors

Human milk glycans have structural homology to cell receptors for enteropathogens and function as receptor decoys. For example, pathogenic strains of *Campylobacter* bind specifically to glycans containing H-2, i.e., 2'-fucosyl-N-acetyllactosamine or 2'-fucosyllactose (2'FL); *Campylobacter* binding and infectivity are inhibited by 2'-FL and other glycans containing this H-2 epitope. Similarly, some diarrheagenic *E. coli* pathogens are strongly inhibited in vivo by human milk oligosaccharides containing 2-linked fucose moieties. Several major strains of human caliciviruses, especially the noroviruses, also bind to 2-linked fucosylated glycans, and this binding is inhibited by human milk 2-linked fucosylated glycans. Consumption of human milk that has high levels of these 2-linked fucosyloligosaccharides was associated with lower risk of norovirus, *Campylobacter*, ST of *E. coli*-associated diarrhea, and moderate-to-severe diarrhea of all causes in a Mexican cohort of breastfeeding children (Newburg D. S. et al., 2004 Glycobiology, 14:253-263; Newburg D. S. et al., 1998 Lancet, 351:1160-1164). Several pathogens utilize sialylated glycans as their host receptors, such as influenza (Couceiro, J. N., Paulson, J. C. & Baum, L. G. Virus Res 29, 155-165 (1993)), parainfluenza (Amonsen, M., Smith, D. F., Cummings, R. D. & Air, G. M. J Virol 81, 8341-8345 (2007), and rotoviruses (Kuhlenschmidt, T. B., Hanafin, W. P., Gelberg, H. B. & Kuhlenschmidt, M. S. Adv Exp Med Biol 473, 309-317 (1999)). The sialyl-Lewis X epitope is used by *Helicobacter pylori* (Mahdavi, J., Sondén, B., Hurtig, M., Olfat, F. O., et al. Science 297, 573-578 (2002)), *Pseudomonas aeruginosa* (Scharfman, A., Delmotte, P., Beau, J., Lamblin, G., et al. Glycoconj J 17, 735-740 (2000)), and some strains of noroviruses (Rydell, G. E., Nilsson, J., Rodriguez-Diaz, J., Ruvoën-Clouet, N., et al. Glycobiology 19, 309-320 (2009)).

Engineering of *E. coli* to Produce Human Milk Oligosaccharide 2'-FL

Described herein is a gene screening approach, which was used to identify new α(1,2) fucosyltransferases (α(1,2) FTs) for the synthesis of fucosyl-linked oligosaccharides in metabolically engineered *E. coli*. Of particular interest are α(1,2) FTs that are capable of the synthesis of the HMOS 2'-fucosyllactose (2'-FL). 2'-FL is the most abundant fucosylated oligosaccharide present in human milk, and this oligosaccharide provides protection to newborn infants against infectious diarrhea caused by bacterial pathogens such as *Campylobacter jejuni* (Ruiz-Palacios, G. M., et al. (2003). J Biol Chem 278, 14112-120; Morrow, A. L. et al. (2004). J Pediatr 145, 297-303; Newburg, D. S. et al. (2004). Glycobiology 14, 253-263).

The synthetic pathway of the fucosyl oligosaccharides of human milk is illustrated in FIG. 1. Structurally, 2'-FL consists of a fucose molecule a 1,2 linked to the galactose portion of lactose (Fucα1-2Galβ1-4Glc). An α(1,2) FT from *H. pylori* strain 26695 termed FutC has been utilized to catalyze the synthesis of 2'-FL in metabolically engineered *E. coli* (Drouillard, S. et al. (2006). Angew Chem Int Ed Engl 45, 1778-780). Therefore, the amino acid sequence of FutC was used as a query in the search algorithm PSI-BLAST (Position Specific Iterated Basic Local Alignment Search Tool) to identify candidate novel α(1,2) FTs for the production of 2'-FL in *E. coli*. Using PSI-BLAST, a list of closely related protein sequences is created based on the query sequence. The algorithm then generates a profile sequence, which summarizes significant motifs present in these sequences. This profile is then used as a new query to identify a larger group of candidate sequences, and the process is iterated to generate an even larger group of candidates.

The FutC amino acid sequence was used as a query for 2 iterations of the PSI-BLAST search algorithm. This search yielded a group of 277 candidates with similarity to FutC, some of which were more closely related (shared amino acid identity greater than 25%) as well as a group that was more distantly related to FutC (shared amino acid identity less than 25%). Of the more closely related group, the predicted α(1,2) FTs from bacterial species that incorporate fucose into the O-antigen of their lipopolysaccharide (LPS) or into the polysaccharide subunits that compose the cell surface capsule were analyzed. α(1,2) FTs from these types of organisms are more likely to utilize fucose as a substrate, given the presence of fucose in their surface carbohydrate structures. α(1,2) FTs from known enteric bacterial species, either commensals or pathogens were also analyzed. Such organisms sometimes display carbohydrate structures on their cell-surface that contain fucose and mimic various 2'-fucosyl containing Lewis antigen structures found in higher organisms (Appelmelk, B. J. et al. (1998). Infect Immun 66, 70-76; Coyne, M. J. et al. (2005). Science 307, 1778-781). Candidate α(1,2) FTs from these types of organisms are more likely to utilize fucose as a substrate and also to catalyze the linkage of fucose to useful acceptor oligosaccharides.

Ten α(1,2) FTs with greater than 25% homology at the amino acid level to FutC identified from the screen were analyzed (Table 1).

TABLE 1

Summary of candidate α (1, 2) fucosyltransferases tested for their ability to promote 2'-FL in engineered *E. coli* strains. The activity of each candidate was compared to FutC and described semi-quantitatively using the "+" symbol in the last column, where FutC is assessed the highest activity with 4 "+" symbols.

| Gene Name | Accession No. (NCBI) | Organism | % Identity w/FutC | Fucose in LPS or capsule? | 2'-FL Synthesis |
|---|---|---|---|---|---|
| futC | NP_206893 NP_206894 | *H. pylori* 26695 | — | Yes | ++++ |
| wblA | BAA33632 | *V. cholerae* O22 | 28% | No | + |
| wbgL | ADN43847 | *E. coli* O126 | 25% | Yes | +++ |
| futD | ZP_04580654 | *H. bilis* ATCC 437879 | 39% | Yes | + |
| futE | ZP_07805473 | *H. cinaedi* CCUG 18818 | 44% | Unknown | − |
| futL | YP_003517185 | *H. mustelae* ATCC 43772 | 70% | Yes | +++ |
| futN | YP_001300461 | *B. vulgatus* ATCC 8482 | 27% | Unknown | ++ |
| futO | ZP_02065239 | *B. ovatus* ATCC 8483 | 27% | Unknown | − |
| wbgN | YP_003500093 | *E. coli* O5S:H7 | 28% | No | + |
| bft1 | CAH09369 | *B. fragilis* 9343 | 34% | Yes | − |
| bft3/wcfB | CAH06753 | *B. fragilis* 9343 | 28% | Yes | + |

The amino acid sequence of *Helicobacter pylori* 26695 alpha-(1,2) fucosyltransferase (FutC) is set forth below (SEQ ID NO: 2; GenBank Accession Number NP_206893 and NP_206894 (GI:15644723 and 15644724), incorporated herein by reference).

```
  1 mafkvvqicg glgnqmfqya fakslqkhln tpvllditsf dwsnrkmqle lfpidlpyas 61 akeiaiakmq hlpklvrdtl kcmgfdrvsq eivfeyepgl lkpsrltyfy gyfqdpryfd 121 aisplikqtf tlpppengnn kkkeeeyhrk lalilaakns vfvhvrrgdy vgigcqlgid 181 yqkkaleyia krvpnmelfv fcedlkftqn ldlgypfmdm ttrdkeeeay wdmllmqsck 241 hgiianstys wwaaylinnp ekiiigpkhw lfghenilck ewvkieshfe vkskkyna
```

The amino acid sequence of *Vibrio cholera* O22 WblA is set forth below (SEQ ID NO: 3; GenBank Accession Number BAA33632 (GI:3721682), incorporated herein by reference).

```
  1 mivmkisggl gnqlfqyavg raiaiqygvp lkldvsaykn yklhngyrld qfninadian 61 edeifhlkgs snrlsrilrr lgwlkkntyy aekqrtiydv svfmqapryl dgywqneqyf 121 sqiravllqe lwpnqplsin aqahqikiqq thavsihvrr gdylnhpeig vldidyykra 181 vdyikekiea pvffvfsndv awckdnfnfi dspvfiedtq teiddlmlmc qcqhnivans 241 sfswwaawln snvdkiviap ktwmaenpkg ykwvpdswre i
```

The amino acid sequence of *Escherichia coli* O126 WbgL is set forth below (SEQ ID NO: 4; GenBank Accession Number ADN43847 (GI:307340785), incorporated herein by reference).

```
  1 msiirlqggl gnqlfqfsfg yalskingtp lyfdishyae nddhggyrln nlqipeeylq 61 yytpkinniy kflvrgsrly peiflflgfc nefhaygydf eyiaqkwksk kyigywqseh 121 ffhkhildlk effipknvse qanllaakil esqsslsihi rrgdyiknkt atlthgvcsl 181 eyykkalnki rdlamirdvf ifsddifwck enietllskk yniyysedls qeedlwlmsl 241 anhhiianss fswwgaylgt sasqiviypt pwyditpknt yipivnhwin vdkhssc
```

The amino acid sequence of *Helicobacter bilis* ATCC 437879 FutD is set forth below (SEQ ID NO: 5; GenBank Accession Number ZP_04580654 (GI: 237750174), incorporated herein by reference).

```
  1 mgdykivelt cglgnqmfqy afakalqkhl qvpvlldktw ydtqdnstqf sldifnvdle 61 yatntqieka karvsklpgl lrkmfglkkh niaysqsfdf hdeyllpndf tyfsgffqna 121 kylkgleqel ksifyydsnn fsnfgkqrle lilqaknsif ihirrgdyck igwelgmdyy 181 kraiqyimdr veepkffifg atdmsfteqf qknlglnenn sanlsektit qdnqhedmfl 241 mcyckhaila nssysfwsay lnndannivi aptpwlldnd niicddwiki ssk
```

The amino acid sequence of *Helicobacter cinaedi* CCUG 18818 alpha-1,2-fucosyltransferase (FutE) is set forth below (SEQ ID NO: 6; GenBank Accession Number ZP_07805473 (GI:313143280), incorporated herein by reference).

```
  1 mlfpfkfiyn rlrykairli rrrasyrpfy efyahivwge egvvndrimk hyressfkpy
 61 afpyginmsf vysndvyall kddfrlkipl rydnamlkkq iqntdksvfl hirrgdylqs
121 eglyvvlgvt yyqkaleilk skitnphifv fsndmcwcke ylmryvdfsg ctidfiegnt
181 egnaveemel mrscqhaiia nstfswwaay lienpdkivi mpkeylndss rflpkqflal
241 knwflvdhiw gsvelan
```

The amino acid sequence of *Helicobacter mustelae* 12198 (ATCC 43772) alpha-1,2-fucosyltransferase (FutL) is set forth below (SEQ ID NO: 7; GenBank Accession Number YP_003517185 (GI:291277413), incorporated herein by reference).

```
  1 mdfkivqvhg glgnqmfqya fakslqthln ipvlldttwf dygnrelglh lfpidlqcas
 61 aqqiaaahmq nlprlvrgal rrmglgrvsk eivfeympel fepsriayfh gyfqdpryfe
121 displikqtf tlphptehae qysrklsqil aaknsvfvhi rrgdymrlgw qldisyqlra
181 iaymakrvqn lelflfcedl efvqnldlgy pfvdmttrdg aahwdmmlmq sckhgiitns
241 tyswwaayli knpekiiigp shwiygneni lckdwvkies qfetks
```

One α(1,2)fucosyltransferase identified through the screen that possessed comparable enzymatic activity relative to FutC was termed FutL. FutL was found to direct the synthesis of 2'-FL at ~75% the level of FutC in the metabolically engineered *E. coli* production strain (Table 1 and FIG. 3). In addition, the data indicated that FutL is significantly less efficient at promoting the synthesis of LDFT, a byproduct that was observed with other α(1,2)FTs. Therefore, FutL offers advantages over the others, e.g., the ability to robustly produce 2'-FL without the concern of concurrently producing other undesirable contaminating oligosaccharides. FutL is derived from *Helicobacter mustelae* and is 70% identical to FutC at the amino acid level.

The amino acid sequence of *Bacteroides vulgatus* ATCC 8482 glycosyl transferase family protein (FutN) is set forth below (SEQ ID NO: 8; GenBank Accession Number YP_001300461 (GI:150005717), incorporated herein by reference).

```
  1 mrlikvtggl gnqmfiyafy lrmkkyypkv ridlsdmmhy kvhygyemhr vfnlphtefc
 61 inqplkkvie flffkkiyer kqapnslraf ekkyfwplly fkgfyqserf fadikdevre
121 sftfdknkan srslnmleil dkdenavslh irrgdylqpk hwattgsvcq lpyyqnaiae
181 msrrvaspsy yifsddiawv kenlplqnav yidwntdeds wqdmmlmshc khhiicnstf
241 swwgawlnpn mdktvivpsr wfqhseapdi yptgwikvpv s
```

The amino acid sequence of *Bacteroides ovatus* ATCC 8483 FutO is set forth below (SEQ ID NO: 9; GenBank Accession Number ZP_02065239 (GI: 160884236), incorporated herein by reference).

```
  1 mkivnilggl gnqmfvyamy lalkeahpee eillcrrsyk gyplhngyel erifgveape
 61 aalsqlarva ypffnykswq lmrhflplrk smasgttqip fdysevtrnd nvyydgywqn
121 eknflsirdk vikaftfpef rdeknkalsd klksvktasc hirrgdylkd piygvcnsdy
181 ytraitelnq svnpdmycif sddigwcken fkfligdkev vfvdwnkgqe sfydmqlmsl
241 chyniianss fswwgawlnn nddkvvvape rwmnktlend picdnwkrik ve
```

The amino acid sequence of *Escherichia coli* O55:H7 (str. CB9615) fucosyltransferase (WbgN) is set forth below (SEQ ID NO: 10; GenBank Accession Number YP_003500093 (GI:291283275), incorporated herein by reference).

```
  1 msivvarlag glgnqmfqya kgyaesvern sslkldlrgy knytlhggfr ldklnidntf
 61 vmskkemcif pnfivraink fpklslcskr feseqyskki ngsmkgsvef igfwqneryf
121 lehkeklrei ftpininlda kelsdvirct nsvsvhirrg dyvsnvealk ihglcteryy
181 idsirylker fnnlvffvfs ddiewckkyk neifsrsddv kfiegntqev dmwlmsnaky
241 hiianssfsw wgawlknydl gitiaptpwf ereelnsfdp cpekwvriek
```

The amino acid sequence of *Bacteroides fragilis* (NCTC) 9343 alpha-1,2-fucosyltransferase (Bft1) is set forth below (SEQ ID NO: 11, GenBank Accession Number CAH09369 (GI:60494568), incorporated herein by reference).

```
  1 mffrccmkiv qiigglgnqm fqfafylalk ekyvnvkldt ssfgaythng feldkvfhve
 61 ylkasireri klsyqgseiw irvlrkllkr kkteyvepyl cfdenaisls cdkyyigywq
121 sykyftniea airgqfhfsk vlsdknefik kqmqnsnsvs lhvrlgdyvn npaysnicts
181 ayynkainii qskvsepkff vfsddtvwck dhlkipnchi idwnnkeesy wdmclmtyck
241 hniianssfs wwgawlntnp eriviapgkw inddrvqvsd iipsdwicv
```

The amino acid sequence of *Bacteroides fragilis* (NCTC) 9343 fucosyl transferase (Bft3/WcfB) is set forth below (SEQ ID NO: 12; GenBank Accession Number CAH06753 (GI:60491992), incorporated herein by reference).

```
  1 mlyvilrgrl gnnlfqiata asltqnfifc tvnkdqerqv llykdsffkn ikvmkgvpdg
 61 ipyykepfhe fsripyeegk dliidgyfqs ekyfkrsvvl dlyritdelr kkiwnicgni
121 lekgetvsih vrrgdylklp halpfcgksy yknaiqyige dkifiicsdd idwckknfig
181 kryyfientt plldlyiqsl cthniisnss fswwgawlne nsnkiviapq mwfgisvklg
241 vsdllpvswv rlpnnytlgr ycfalykvve dyllnilrli wkrkknm
```

Homology Comparison Matrix of Fucosyltransferases Examined in this Study:

|      | FutC | WbsJ | WbgL | WblA | WbgN | Bft1 | Bft3 | FutD | FutE | FutL | FutN | FutO |
|------|------|------|------|------|------|------|------|------|------|------|------|------|
| FutC | —    | 30%  | 28%  | 28%  | 28%  | 34%  | 28%  | 39%  | 44%  | 70%  | 27%  | 27%  |
| WbsJ | 30%  | —    | 33%  | 33%  | 36%  | 36%  | 40%  | 30%  | 35%  | 30%  | 33%  | 36%  |
| WbgL | 28%  | 33%  | —    | 33%  | 37%  | 32%  | 39%  | 31%  | 32%  | 25%  | 32%  | 33%  |
| WblA | 28%  | 33%  | 33%  | —    | 36%  | 37%  | 33%  | 31%  | 38%  | 29%  | 31%  | 35%  |
| WbgN | 28%  | 36%  | 37%  | 36%  | —    | 32%  | 37%  | 30%  | 38%  | 30%  | 32%  | 35%  |
| Bft1 | 34%  | 36%  | 32%  | 37%  | 32%  | —    | 30%  | 32%  | 37%  | 33%  | 35%  | 38%  |
| Bft3 | 28%  | 40%  | 39%  | 33%  | 37%  | 30%  | —    | 30%  | 33%  | 29%  | 34%  | 35%  |
| FutD | 39%  | 30%  | 31%  | 31%  | 30%  | 32%  | 30%  | —    | 34%  | 40%  | 28%  | 31%  |
| FutE | 44%  | 35%  | 32%  | 38%  | 38%  | 37%  | 33%  | 34%  | —    | 33%  | 33%  | 36%  |
| FutL | 70%  | 30%  | 25%  | 29%  | 30%  | 33%  | 29%  | 40%  | 33%  | —    | 30%  | 28%  |
| FutN | 27%  | 33%  | 32%  | 31%  | 32%  | 35%  | 34%  | 28%  | 34%  | 30%  | —    | 37%  |
| FutO | 27%  | 36%  | 33%  | 35%  | 35%  | 38%  | 35%  | 31%  | 36%  | 28%  | 37%  | —    |

All of these proteins are found in bacteria that interact with the gastrointestinal system of higher organisms. In addition, 6 of the 10 selected incorporate fucose into their cell surface glycans. Such genes were predicted to have the strongest activity in terms of fucosyl-oligosaccharide synthesis. In this group of 10 candidates, 2 enzymes found in bacterial strains that do not incorporate fucose into cell surface glycans (WblA and WbgN) were also included. It was predicted that these candidates would have little or no fucosyl-oligosaccharide synthesis activity, and therefore might serve as a useful negative control to validate the screening approach.

Candidate α(1,2) FTs were cloned by standard molecular biological techniques into an expression plasmid. This plasmid utilizes the strong leftwards promoter of bacteriophage λ (termed $P_L$) to direct expression of the candidate genes (Sanger, F. et al. (1982). J Mol Biol 162, 729-773). The promoter is controllable, e.g., a trp-cI construct is stably integrated the into the E. coli host's genome (at the ampC locus), and control is implemented by adding tryptophan to the growth media. Gradual induction of protein expression is accomplished using a temperature sensitive cI repressor. Another similar control strategy (temperature independent expression system) has been described (Mieschendahl et al., 1986, Bio/Technology 4:802-808). The plasmid also carries the E. coli rcsA gene to up-regulate GDP-fucose synthesis, a critical precursor for the synthesis of fucosyl-linked oligosaccharides. In addition, the plasmid carries a β-lactamase (bla) gene for maintaining the plasmid in host strains by ampicillin selection (for convenience in the laboratory) and a native thyA (thymidylate synthase) gene as an alternative means of selection in thyA⁻ hosts. Alternative selectable markers include the proBA genes to complement proline auxotrophy (Stein et al., (1984), J Bacteriol 158:2, 696-700 (1984) or purC to complement adenine auxotrophy (Parker, J., (1984), J Bacteriol 157:3, 712-7). To act as plasmid selectable markers each of these genes are first inactivated in the host cell chromosome, then wild type copies of the genes are provided on the plasmid. Alternatively a drug resistance gene may be used on the plasmid, e.g. beta-lactamase (this gene is already on the expression plasmid described above, thereby permitting selection with ampicillin). Ampicilline selection is well known in the art and described in standard manuals such as Maniatis et al., (1982) Molecular cloning, a laboratory manual. Cold Spring Harbor Laboratory, Cold Spring, N.Y.

Figure 2:
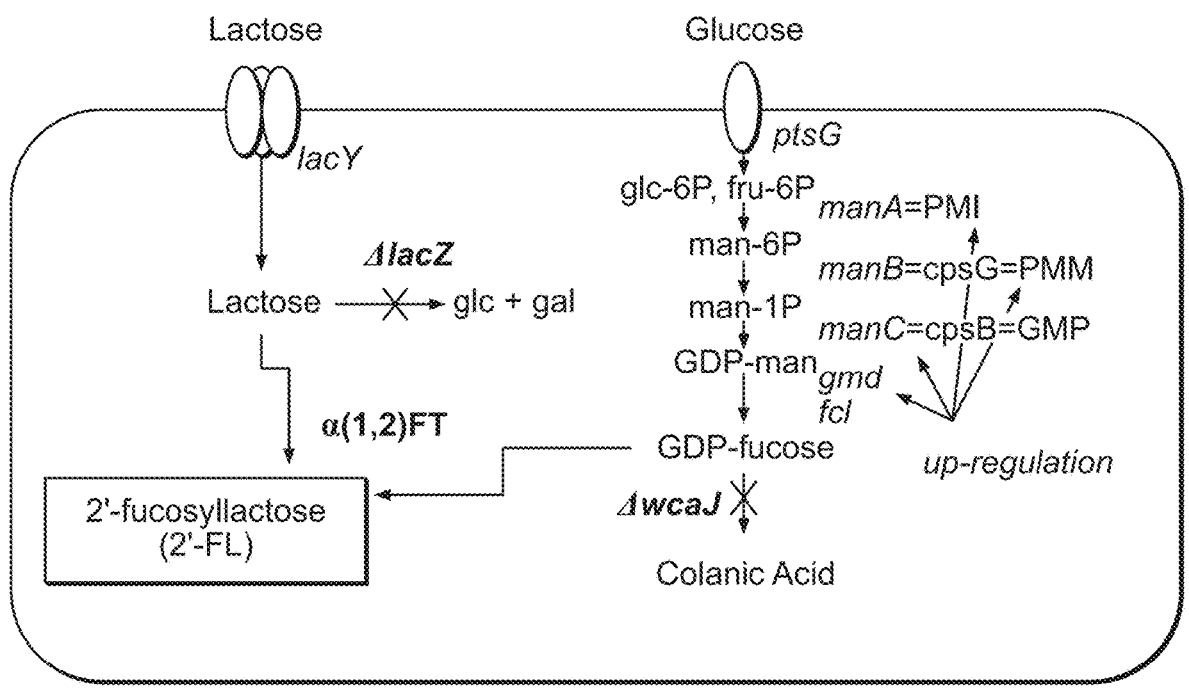
FIG. 2 is a schematic demonstrating metabolic pathways and the changes introduced into them to engineer 2'-fucosyllactose (2'-FL) synthesis in *Escherichia coli* (*E. coli*).

The expression constructs were transformed into a host strain useful for the production of 2'-FL. Biosynthesis of 2'-FL requires the generation of an enhanced cellular pool of both lactose and GDP-fucose (FIG. 2). The wild-type Escherichia coli K12 prototrophic strain W3110 was selected as the parent background to test the ability of the candidates to catalyze 2'-FL production (Bachmann, B. J. (1972). Bacteriol Rev 36, 525-557). The particular W3110 derivative employed was one that previously had been modified by the introduction (at the ampC locus) of a tryptophan-inducible $P_{trpB}$ cI+ repressor cassette, generating an E. coli strain known as GI1724 (LaVallie, E. R. et al. (2000). Methods Enzymol 326, 322-340). Other features of GI1724 include lacIq and lacPL8 promoter mutations. E. coli strain GI1724 affords economical production of recombinant proteins from the phage λ $P_L$ promoter following induction with low levels of exogenous tryptophan (LaVallie, E. R. et al. (1993). Biotechnology (N Y) 11, 187-193; Mieschendahl, et al. (1986). Bio/Technology 4, 802-08). Additional genetic alterations were made to this strain to promote the biosynthesis of 2'-FL. This was achieved in strain GI1724 through several manipulations of the chromosome using λ Red recombineering (Court, D. L. et al. (2002). Annu Rev Genet 36, 361-388) and generalized P1 phage transduction.

First, the ability of the E. coli host strain to accumulate intracellular lactose was engineered by simultaneous deletion of the endogenous β-galactosidase gene (lacZ) and the lactose operon repressor gene (lacI). During construction of this deletion, the lacIq promoter was placed immediately upstream of the lactose permease gene, lacY. The modified strain maintains its ability to transport lactose from the culture medium (via LacY), but is deleted for the wild-type copy of the lacZ (β-galactosidase) gene responsible for lactose catabolism. Therefore, an intracellular lactose pool is created when the modified strain is cultured in the presence of exogenous lactose. A schematic of the $P_{lacIq}$ lacY⁺ chromosomal construct is shown in FIG. 6.

Genomic DNA sequence of the $P_{lacIq}$ lacY⁺ chromosomal construct is set forth below (SEQ ID NO: 13):

CACCATCGAATGGCGCAAAACCTTTCGCGGTATGGCATGATAGCGCCCGG

AAGAGAGTCAAGTGTAGGCTGGAGCTGCTTCGAAGTTCCTATACTTTCTA

GAGAATAGGAACTTCGGAATAGGAACTTCGGAATAGGAACTAAGGAGGAT

ATTCATATGTACTATTTAAAAAACACAAACTTTTGGATGTTCGGTTTATT

CTTTTTCTTTTACTTTTTTATCATGGGAGCCTACTTCCCGTTTTTCCCGA

TTTGGCTACATGACATCAACCATATCAGCAAAAGTGATACGGGTATTATT

TTTGCCGCTATTTCTCTGTTCTCGCTATTATTCCAACCGCTGTTTGGTCT

GCTTTCTGACAAACTCGGGCTGCGCAAATACCTGCTGTGGATTATTACCG

GCATGTTAGTGATGTTTGCGCCGTTCTTTATTTTTATCTTCGGGCCACTG

TTACAATACAACATTTTAGTAGGATCGATTGTTGGTGGTATTTATCTAGG

CTTTTGTTTTAACGCCGGTGCGCCAGCAGTAGAGGCATTTATTGAGAAAG

TCAGCCGTCGCAGTAATTTCGAATTTGGTCGCGCGCGGATGTTTGGCTGT

GTTGGCTGGGCGCTGTGTGCCTCGATTGTCGGCATCATGTTCACCATCAA

TAATCAGTTTGTTTTCTGGCTGGGCTCTGGCTGTGCACTCATCCTCGCCG

TTTTACTCTTTTTCGCCAAAACGGATGCGCCCTCTTCTGCCACGGTTGCC

AATGCGGTAGGTGCCAACCATTCGGCATTTAGCCTTAAGCTGGCACTGGA

ACTGTTCAGACAGCCAAAACTGTGGTTTTTGTCACTGTATGTTATTGGCG

TTTCCTGCACCTACGATGTTTTTGACCAACAGTTTGCTAATTTCTTTACT

TCGTTCTTTGCTACCGGTGAACAGGGTACGCGGGTATTTGGCTACGTAAC

GACAATGGGCGAATTACTTAACGCCTCGATTATGTTCTTTGCGCCACTGA

TCATTAATCGCATCGGTGGGAAAAACGCCCTGCTGCTGGCTGGCACTATT

ATGTCTGTACGTATTATTGGCTCATCGTTCGCCACCTCAGCGCTGGAAGT

GGTTATTCTGAAAACGCTGCATATGTTTGAAGTACCGTTCCTGCTGGTGG

GCTGCTTTAAATATATTACCAGCCAGTTTGAAGTGCGTTTTTCAGCGACG

ATTTATCTGGTCTGTTTCTGCTTCTTTAAGCAACTGGCGATGATTTTTAT

GTCTGTACTGGCGGGCAATATGTATGAAAGCATCGGTTTCCAGGGCGCTT

ATCTGGTGCTGGGTCTGGTGGCGCTGGGCTTCACCTTAATTTCCGTGTTC

ACGCTTAGCGGCCCCGGCCCGCTTTCCCTGCTGCGTCGTCAGGTGAATGA

```
AGTCGCTTAAGCAATCAATGTCGGATGCGGCGCGAGCGCCTTATCCGACC

AACATATCATAACGGAGTGATCGCATTGTAAATTATAAAAATTGCCTGAT

ACGCTGCGCTTATCAGGCCTACAAGTTCAGCGATCTACATTAGCCGCATC

CGGCATGAACAAAGCGCAGGAACAAGCGTCGCA
```

Second, the ability of the host *E. coli* strain to synthesize colanic acid, an extracellular capsular polysaccharide, was eliminated by the deletion of the wcaJ gene, encoding the UDP-glucose lipid carrier transferase (Stevenson, G. et al. (1996). J Bacteriol 178, 4885-893). In a wcaJ null background GDP-fucose accumulates in the *E. coli* cytoplasm (Dumon, C. et al. (2001). Glycoconj J 18, 465-474). A schematic of the chromosomal deletion of wcaJ is shown in FIG. 7.

The sequence of the chromosomal region bearing the ΔwcaJ::FRT mutation is set forth below (SEQ ID NO: 14):

```
GTTCGGTTATATCAATGTCAAAAACCTCACGCCGCTCAAGCTGGTGATCA

ACTCCGGGAACGGCGCAGCGGGTCCGGTGGTGGACGCCATTGAAGCCCGC

TTTAAAGCCCTCGGCGCGCCCGTGGAATTAATCAAAGTGCACAACACGCC

GGACGGCAATTTCCCCAACGGTATTCCTAACCCACTACTGCCGGAATGCC

GCGACGACACCCGCAATGCGGTCATCAAACACGGCGCGGATATGGGCATT

GCTTTTGATGGCGATTTTGACCGCTGTTTCCTGTTTGACGAAAAAGGGCA

GTTTATTGAGGGCTACTACATTGTCGGCCTGTTGGCAGAAGCATTCCTCG

AAAAAAATCCCGGCGCGAAGATCATCCACGATCCACGTCTCTCCTGGAAC

ACCGTTGATGTGGTGACTGCCGCAGGTGGCACGCCGGTAATGTCGAAAAC

CGGACACGCCTTTATTAAAGAACGTATGCGCAAGGAAGACGCCATCTATG

GTGGCGAAATGAGCGCCCACCATTACTTCCGTGATTTCGCTTACTGCGAC

AGCGGCATGATCCCGTGGCTGCTGGTCGCCGAACTGGTGTGCCTGAAAGA

TAAAACGCTGGGCGAACTGGTACGCGACCGGATGGCGGCGTTTCCGGCAA

GCGGTGAGATCAACAGCAAACTGGCGCAACCCGTTGAGGCGATTAACCGC

GTGGAACAGCATTTTAGCCGTGAGGCGCTGGCGGTGGATCGCACCGATGG

CATCAGCATGACCTTTGCCGACTGGCGCTTTAACCTGCGCACCTCCAATA

CCGAACCGGTGGTGCGCCTGAATGTGGAATCGCGCGGTGATGTGCCGCTG

ATGGAAGCGCGAACGCGAACTCTGCTGACGTTGCTGAACGAGTAATGTCG

GATCTTCCCTTACCCCACTGCGGGTAAGGGGCTAATAACAGGAACAACGA

TGATTCCGGGGATCCGTCGACCTGCAGTTCGAAGTTCCTATTCTCTAGAA

AGTATAGGAACTTCGAAGCAGCTCCAGCCTACAGTTAACAAAGCGGCATA

TTGATATGAGCTTACGTGAAAAAACCATCAGCGGCGCGAAGTGGTCGGCG

ATTGCCACGGTGATCATCATCGGCCTCGGGCTGGTGCAGATGACCGTGCT

GGCGCGGATTATCGACAACCACCAGTTCGGCCTGCTTACCGTGTCGCTGG

TGATTATCGCGCTGGCAGATACGCTTTCTGACTTCGGTATCGCTAACTCG

ATTATTCAGCGAAAAGAAATCAGTCACCTTGAACTCACCACGTTGTACTG

GCTGAACGTCGGGCTGGGGATCGTGGTGTGCGTGGCGGTGTTTTTGTTGA

GTGATCTCATCGGCGACGTGCTGAATAACCCGGACCTGGCACCGTTGATT

AAAACATTATCGCTGGCGTTTGTGGTAATCCCCCACGGGCAACAGTTCCG

CGCGTTGATGCAAAAAGAGCTGGAGTTCAACAAAATCGGCATGATCGAAA

CCAGCGCGGTGCTGGCGGGCTTCACTTGTACGGTGGTTAGCGCCCATTTC

TGGCCGCTGGCGATGACCGCGATCCTCGGTTATCTGGTCAATAGTGCGGT

GAGAACGCTGCTGTTTGGCTACTTTGGCCGCAAAATTTATCGCCCCGGTC

TGCATTTCTCGCTGGCGTCGGTGGCACCGAACTTACGCTTTGGTGCCTGG

CTGACGGCGGACAGCATCATCAACTATCTCAATACCAACCTTTCAACGCT

CGTGCTGGCGCGTATTCTCGGCGCGGGCGTGGCAGGGGGATACAACCTGG

CGTACAACGTGGCCGTTGTGCCACCGATGAAGCTGAACCCAATCATCACC

CGCGTGTTGTTTCCGGCATTCGCCAAAATTCAGGACGATACCGAAAAGCT

GCGTGTTAACTTCTACAAGCTGCTGTCGGTAGTGGGGATTATCAACTTTC

CGGCGCTGCTCGGGCTAATGGTGGTGTCGAATAACTTTGTACCGCTGGTC

TTTGGTGAGAAGTGGAACAGCATTATTCCGGTGCTGCAATTGCTGTGTGT

GGTGGGTCTGCTGCGCTCCG
```

Third, the magnitude of the cytoplasmic GDP-fucose pool was enhanced by the introduction of a null mutation into the lon gene. Lon is an ATP-dependant intracellular protease that is responsible for degrading RcsA, which is a positive transcriptional regulator of colanic acid biosynthesis in *E. coli* (Gottesman, S. & Stout, V. Mol Microbiol 5, 1599-1606 (1991)). In a lon null background, RcsA is stabilized, RcsA levels increase, the genes responsible for GDP-fucose synthesis in *E. coli* are up-regulated, and intracellular GDP-fucose concentrations are enhanced. The lon gene was almost entirely deleted and replaced by an inserted functional, wild-type, but promoter-less *E. coli* lacZ+ gene (Δlon::(kan, lacZ+). λ Red recombineering was used to perform the construction. A schematic of the kan, lacZ+ insertion into the lon locus is shown in FIG. 8.

Genomic DNA sequence surrounding the lacZ+ insertion into the lon region in the *E. coli* strain is set forth below (SEQ ID NO: 15):

```
GTGGATGGAAGAGGTGGAAAAAGTGGTTATGGAGGAGTGGGTAATTGATG

GTGAAAGGAAAGGGTTGGTGATTTATGGGAAGGGGGAAGGGGAAGAGGGA

TGTGGTGAATAATTAAGGATTGGGATAGAATTAGTTAAGGAAAAAGGGGG

GATTTTATGTGGGGTTTAATTTTTGGTGTATTGTGGGGGTTGAATGTGGG

GGAAAGATGGGGATATAGTGAGGTAGATGTTAATAGATGGGGTGAAGGAG

AGTGGTGTGATGTGATTAGGTGGGGGAAATTAAAGTAAGAGAGAGGTGTA

TGATTGGGGGATGGGTGGAGGTGGAGTTGGAAGTTGGTATTGTGTAGAA

AGTATAGGAAGTTGAGAGGGGTTTTGAAGGTGAGGGTGGGGAAGGAGTG

AGGGGGAAGGGTGGTAAAGGAAGGGGAAGAGGTAGAAAGGGAGTGGGG

AGAAAGGGTGGTGAGGGGGATGAATGTGAGGTAGTGGGGTATGTGGAGA

AGGGAAAGGGAAGGGAAAGAGAAAGGAGGTAGGTTGGAGTGGGGTTAG

ATGGGGATAGGTAGAGTGGGGGGTTTTATGGAGAGGAAGGGAAGGGGAAT

TGGGAGGTGGGGGGGGGTGTGGTAAGGTTGGGAAGGGGTGGAAAGTAAAG

TGGATGGGTTTGTTGGGGGGAAGGATGTGATGGGGGAGGGGATGAAGATG

TGATGAAGAGAGAGGATGAGGATGGTTTGGGATGATTGAAGAAGATGGAT
```

```
TGGAGGGAGGTTGTGGGGGGGTTGGGTGGAGAGGGTATTGGGGTATGAG
TGGGGAGAAGAGAGAATGGGGTGGTGTGATGGGGGGGTGTTGGGGGTGTG
AGGGGAGGGGGGGGGGTTGTTTTTGTGAAGAGGGAGGTGTGGGGTGGGG
TGAATGAAGTGGAGGAGGAGGGAGGGGGGGTATGGTGGGTGGGGAGGAGG
GGGGTTGGTTGGGGAGGTGTGGTGGAGGTTGTGAGTGAAGGGGGAAGGGA
GTGGGTGGTATTGGGGAAGTGGGGGGGGAGGATGTGGTGTGATGTGAGG
TTGGTGGTGGGGAGAAAGTATGGATGATGGGTGATGGAATGGGGGGGTG
GATAGGGTTGATGGGGGTAGGTGGGGATTGGAGGAGGAAGGGAAAGATGG
GATGGAGGGAGGAGGTAGTGGGATGGAAGGGGGTGTTGTGGATGAGGATG
ATGTGGAGGAAGAGGATGAGGGGGTGGGGGGAGGGGAAGTGTTGGGGAGG
GTGAAGGGGGATGGGGGAGGGGAGGATGTGGTGGTGAGGGATGGGGAT
GGGTGGTTGGGGAATATGATGGTGGAAAATGGGGGGTTTTGTGGATTGAT
GGAGTGTGGGGGGTGGGTGTGGGGAGGGGTATGAGGAGATAGGGTTGG
GTAGGGGTGATATTGGTGAAGAGGTTGGGGGGGAATGGGGTGAGGGGTTG
GTGGTGGTTTAGGGTATGGGGGGTGGGGATTGGGAGGGGATGGGGTTGTA
TGGGGTTGTTGAGGAGTTGTTGTAATAAGGGGATGTTGAAGTTGGTATTG
GGAAGTTGGTATTGTGTAGAAAGTATAGGAAGTTGGAAGGAGGTGGAGGG
TAGATAAAGGGGGGGGTTATTTTTGAGAGGAGAGGAAGTGGTAATGGTAG
GGAGGGGGGGTGAGGTGGAATTGGGGGGATAGTGAGGGGGTGGAGGAGTG
GTGGGGAGGAATGGGGATATGAAAGGGTGGATATTGAGGGATGTGGGTT
GTTGGGGGTGGAGGAGATGGGGATGGGTGGTTTGGATGAGTTGGTGTTGA
GTGTAGGGGGTGATGTTGAAGTGGAAGTGGGGGGGGGAGTGGTGTGGGGG
ATAATTGAATTGGGGGGTGGGGGAGGGGAGAGGGTTTTGGGTGGGGAAGA
GGTAGGGGGTATAGATGTTGAGAATGGGAGATGGGAGGGGTGAAAAGAGG
GGGGAGTAAGGGGGTGGGGATAGTTTTGTTGGGGGGGTAATGGGAGGGAG
TTTAGGGGGTGTGGTAGGTGGGGAGGTGGGAGTTGAGGGGAATGGGGGG
GGGATGGGTGTATGGGTGGGGAGTTGAAGATGAAGGGTAATGGGGATTT
GAGGAGTAGGATGAATGGGGTAGGTTTTGGGGGTGATAAATAAGGTTTTG
GGGTGATGGTGGGAGGGGTGAGGGGTGGTAATGAGGAGGGGATGAGGAAG
TGTATGTGGGGTGGAGTGGAAGAAGGGTGGTTGGGGGTGGTAATGGGGGG
GGGGGTTGGAGGGTTGGAGGGAGGGGTTAGGGTGAATGGGGGTGGGTTGA
GTTAGGGGAATGTGGTTATGGAGGGGTGGAGGGGTGAAGTGATGGGGAG
GGGGGTGAGGAGTTGTTTTTTATGGGGAATGGAGATGTGTGAAAGAAAGG
GTGAGTGGGGGTTAAATTGGGAAGGGTTATTAGGGAGGTGGATGGAAAAA
TGGATTTGGGTGGTGGTGAGATGGGGATGGGTGGGAGGGGGGGGGAG
GGTGAGAGTGAGGTTTTGGGGAGAGGGGAGTGGTGGGAGGGGGTGATGT
GGGGGGGTTGTGAGGATGGGGTGGGGTTGGGTTGGAGTAGGGGTAGTGTG
AGGGAGAGTTGGGGGGGGGTGTGGGGTGGGGTAGTTGAGGGAGTTGAAT
GAAGTGTTTAGGTTGTGGAGGGAGATGGAGAGGGAGTTGAGGGGTTGGGA
GGGGGTTAGGATGGAGGGGGAGGATGGAGTGGAGGAGGTGGTTATGGGTA
```
```
TGAGGGAAGAGGTATTGGGTGGTGAGTTGGATGGTTTGGGGGGATAAAGG
GAAGTGGAAAAGTGGTGGTGGTGTTTTGGTTGGGTGAGGGGTGGATGGG
GGGTGGGGTGGGGAAAGAGGAGAGGGTTGATAGAGAAGTGGGGATGGTTG
GGGGTATGGGGAAAATGAGGGGGGTAAGGGGAGGAGGGGTTGGGGTTTTG
ATGATATTTAATGAGGGAGTGATGGAGGGAGTGGGAGAGGAAGGGGGGGT
GTAAAGGGGATAGTGAGGAAAGGGGTGGGAGTATTTAGGGAAAGGGGGA
AGAGTGTTAGGGATGGGGTGGGGGTATTGGGAAAGGATGAGGGGGGGGGT
GTGTGGAGGTAGGGAAAGGGATTTTTTGATGGAGGGATTTGGGGAGAGGGG
GGAAGGGGTGGTGTTGATGGAGGGGGGGGTAGATGGGGGAAATAATATGG
GTGGGGGTGGTGTGGGGTGGGGGGGGTTGATAGTGGAGGGGGGGGGAAGG
ATGGAGAGATTTGATGGAGGGATAGAGGGGGTGGTGATTAGGGGGGTGGG
GTGATTGATTGGGGAGGGAGGAGATGATGAGAGTGGGGTGATTAGGATGG
GGGTGGAGGATTGGGGTTAGGGGTTGGGTGATGGGGGGTAGGGAGGGGGG
ATGATGGGTGAGAGGATTGATTGGGAGGATGGGGTGGGTTTGAATATTGG
GTTGATGGAGGAGATAGAGGGGGTAGGGGTGGGAGAGGGTGTAGGAGAGG
GGATGGTTGGGATAATGGGAAGAGGGGAGGGGGTTAAAGTTGTTGTGGTT
GATGAGGAGGATATGGTGGAGGATGGTGTGGTGATGGATGAGGTGAGGAT
GGAGAGGATGATGGTGGTGAGGGTTAAGGGGTGGAATGAGGAAGGGGTTG
GGGTTGAGGAGGAGGAGAGGATTTTGAATGGGGAGGTGGGGGAAAGGGAG
ATGGGAGGGTTGTGGTTGAATGAGGGTGGGGTGGGGGGTGTGGAGTTGAA
GGAGGGGAGGATAGAGATTGGGGATTTGGGGGGTGGAGAGTTTGGGGTTT
TGGAGGTTGAGAGGTAGTGTGAGGGGATGGGGATAAGGAGGAGGGTGATG
GATAATTTGAGGGGGGAAAGGGGGGGTGGGGGTGGGAGGTGGGTTTGAG
GGTGGGATAAAGAAAGTGTTAGGGGTAGGTAGTGAGGGAAGTGGGGGGAG
ATGTGAAGTTGAGGGTGGAGTAGAGGGGGGGTGAAATGATGATTAAAGGG
AGTGGGAAGATGGAAATGGGTGATTTGTGTAGTGGGTTTATGGAGGAAGG
AGAGGTGAGGGAAAATGGGGGTGATGGGGGAGATATGGTGATGTTGGAGA
TAAGTGGGGTGAGTGGAGGGGAGGAGGATGAGGGGGAGGGGTTTTGTGG
GGGGGGTAAAAATGGGGTGAGGTGAAATTGAGAGGGGAAAGGAGTGTGGT
GGGGGTAAGGGAGGGAGGGGGGGTTGGAGGAGAGATGAAAGGGGGAGTTA
AGGGGATGAAAAATAATTGGGGTGTGGGGTTGGTGTAGGGAGGTTTGATG
AAGATTAAATGTGAGGGAGTAAGAAGGGGTGGGATTGTGGGTGGGAAGAA
AGGGGGATTGAGGGTAATGGGATAGGTGAGGTTGGTGTAGATGGGGGGA
TGGTAAGGGTGGATGTGGGAGTTTGAGGGGAGGAGGAGAGTATGGGGGTG
AGGAAGATGGGAGGGAGGGAGGTTTGGGGGAGGGGTTGTGGTGGGGGAAA
GGAGGGAAAGGGGGATTGGGGATTGAGGGTGGGGAAGTGTTGGGAAGGGG
GATGGGTGGGGGGGTGTTGGGTATTAGGGGAGGTGGGGAAAGGGGGATGT
GGTGGAAGGGGATTAAGTTGGGTAAGGGGAGGGTTTTGGGAGTGAGGAGG
TTGTAAAAGGAGGGGGAGTGAATGGGTAATGATGGTGATAGTAGGTTTGG
TGAGGTTGTGAGTGGAAAATAGTGAGGTGGGGAAAATGGAGTAATAAAA
AGAGGGGTGGGAGGGTAATTGGGGGTTGGGAGGGTTTTTTTGTGTGGGTA
```

-continued

```
AGTTAGATGGGGGATGGGGGTTGGGGTTATTAAGGGGTGTTGTAAGGGGA

TGGGTGGGGTGATATAAGTGGTGGGGGTTGGTAGGTTGAAGGATTGAAGT

GGGATATAAATTATAAAGAGGAAGAGAAGAGTGAATAAATGTGAATTGAT

GGAGAAGATTGGTGGAGGGGGTGATATGTGTAAAGGTGGGGGTGGGGGTG

GGTTAGATGGTATTATTGGTTGGGTAAGTGAATGTGTGAAAGAAGG
```

Fourth, a thyA (thymidylate synthase) mutation was introduced into the strain by P1 transduction. In the absence of exogenous thymidine, thyA strains are unable to make DNA and die. The defect can be complemented in trans by supplying a wild-type thyA gene on a multicopy plasmid (Belfort, M., Maley, G. F., and Maley, F. (1983). Proc Natl Acad Sci USA 80, 1858-861). This complementation was used here as a means of plasmid maintenance.

An additional modification that is useful for increasing the cytoplasmic pool of free lactose (and hence the final yield of 2'-FL) is the incorporation of a lacA mutation. LacA is a lactose acetyltransferase that is only active when high levels of lactose accumulate in the E. coli cytoplasm. High intracellular osmolarity (e.g., caused by a high intracellular lactose pool) can inhibit bacterial growth, and E. coli has evolved a mechanism for protecting itself from high intra cellular osmolarity caused by lactose by "tagging" excess intracellular lactose with an acetyl group using LacA, and then actively expelling the acetyl-lactose from the cell (Danchin, A. Bioessays 31, 769-773 (2009)). Production of acetyl-lactose in E. coli engineered to produce 2'-FL or other human milk oligosaccharides is therefore undesirable: it reduces overall yield. Moreover, acetyl-lactose is a side product that complicates oligosaccharide purification schemes. The incorporation of a lacA mutation resolves these problems. Sub-optimal production of fucosylated oligosaccharides occurs in strains lacking either or both of the mutations in the colanic acid pathway and the lon protease. Diversion of lactose into a side product (acetyl-lactose) occurs in strains that don't contain the lacA mutation. A schematic of the lacA deletion and corresponding genomic sequence is provided above (SEQ ID NO: 13).

The strain used to test the different $\alpha(1,2)$ FT candidates incorporates all the above genetic modifications and has the following genotype: $\Delta ampC::P_{trp}^{B}cI$, A(lacI-lacZ)::FRT, $P_{lacIq}lacY^+$, $\Delta wcaJ$::FRT, thyA::Tn10, $\Delta lon$:(npt3, lacZ$^+$), $\Delta lacA$ The E. coli strains harboring the different $\alpha(1,2)$ FT candidate expression plasmids were analyzed. Strains were grown in selective media (lacking thymidine) to early exponential phase. Lactose was then added to a final concentration of 1%, and tryptophan (200 μM) was added to induce expression of each candidate $\alpha(1,2)$ FT from the $P_L$ promoter. At the end of the induction period (~20 h) equivalent OD 600 units of each strain were harvested. Lysates were prepared and analyzed for the presence of 2'-FL by thin layer chromatography (TLC). As shown in FIG. 3A, a control strain producing FutC-Myc was efficient in the biosynthesis of 2'-FL and also produced a smaller amount of the tetrasaccharide lactodifucotetraose (LDFT). The previously characterized $\alpha(1,2)$ FT WbsJ from E. coli O128:B12 was also capable of catalyzing 2'-FL synthesis, although only at ~30% the level produced by FutC-Myc (FIG. 3A, lanes 5 and 6). WblA (derived from V. cholerae O22) was able to promote 2'-FL synthesis, although at a significantly lower level compared to FutC (FIG. 3A, lanes 7 and 8). This result was not unexpected, as V. cholerae O22 does not incorporate fucose into cell surface glycans (Cox, A. D. et al. (1997). Carbohydr Res 304, 191-208). The strain producing WbgL (derived from E. coli strain O126) from plasmid pG204 synthesized a significant amount of 2'-FL, approximately ~75% of the amount produced by FutC-Myc (FIG. 3A, lanes 9 and 10). WbgL was also capable of synthesizing LDFT. The strain producing FutL (derived from H. mustelae ATCC 43772) from plasmid pG216 was capable of directing the synthesis of robust amounts of 2'-FL, comparable to the levels obtained utilizing FutC-Myc and WbgL (FIG. 3B, lanes 7 and 8). Furthermore, a strain producing FutN (derived from B. vulgatus ATCC 8482) from plasmid pG217 also produced significant amounts of 2'-FL, approximately ~50% the amount produced by FutC-Myc (FIG. 3C, lanes 5 and 6). FutN is derived from the commensal bacterium B. vulgatus, and therefore may not be subject to the same concerns associated with utilization of an $\alpha(1,2)$ FT obtained from a pathogenic bacterium for the production of a food additive.

Figure 9:
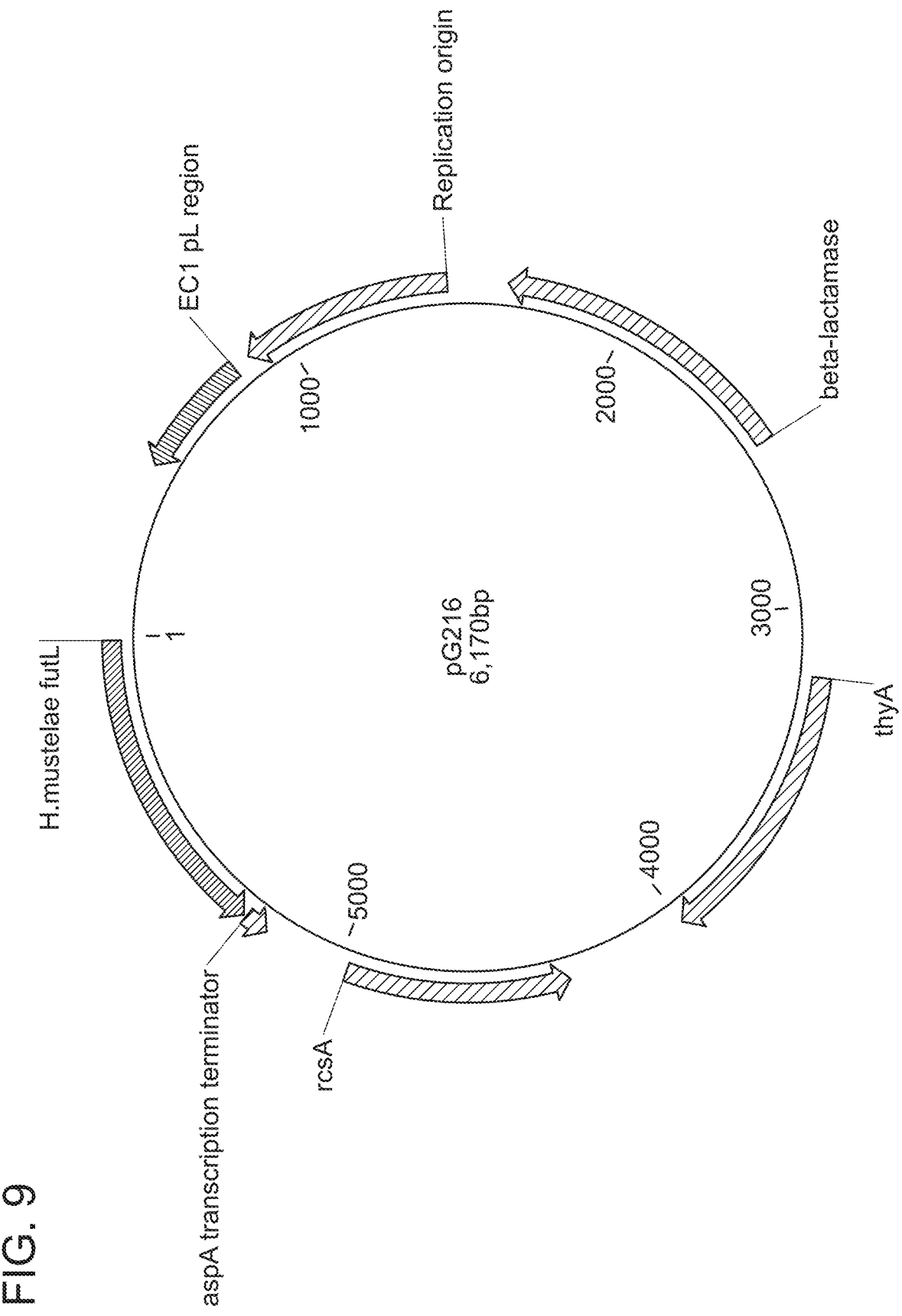
FIG. 9 is a diagram of plasmid pG204.

A map of plasmid pG204 is shown in FIG. 9. The sequence of plasmid pG204 is set forth below (SEQ ID NO: 16):

```
AATTCTAAAAATTGATTGAATGTATGCAAATAAATGCATACACCATAGGT

GTGGTTTAATTTGATGCCCTTTTTCAGGGCTGGAATGTGTAAGAGCGGGG

TTATTTATGCTGTTGTTTTTTTGTTACTCGGGAAGGGCTTTACCTCTTCC

GCATAAACGCTTCCATCAGCGTTTATAGTTAAAAAAATCTTTCGGAACTG

GTTTTGCGCTTACCCCAACCAACAGGGGATTTGCTGCTTTCCATTGAGCC

TGTTTCTCTGCGCGACGTTCGCGGCGGCGTGTTTGTGCATCCATCTGGAT

TCTCCTGTCAGTTAGCTTTGGTGGTGTGTGGCAGTTGTAGTCCTGAACGA

AAACCCCCGCGATTGGCACATTGGCAGCTAATCCGGAATCGCACTTACG

GCCAATGCTTCGTTTCGTATCACACACCCCAAAGCCTTCTGCTTTGAATG

CTGCCCTTCTTCAGGGCTTAATTTTTAAGAGCGTCACCTTCATGGTGGTC

AGTGCGTCCTGCTGATGTGCTCAGTATCACCGCCAGTGGTATTTATGTCA

ACACCGCCAGAGATAATTTATCACCGCAGATGGTTATCTGTATGTTTTTT

ATATGAATTTATTTTTTGCAGGGGGGCATTGTTTGGTAGGTGAGAGATCA

ATTCTGCATTAATGAATCGGCCAACGCGCGGGAGAGGCGGTTTGCGTAT

TGGGCGCTCTTCCGCTTCCTCGCTCACTGACTCGCTGCGCTCGGTCGTTC

GGCTGCGGCGAGCGGTATCAGCTCACTCAAAGGCGGTAATACGGTTATCC

ACAGAATCAGGGGATAACGCAGGAAAGAACATGTGAGCAAAAGGCCAGCA

AAAGGCCAGGAACCGTAAAAAGGCCGCGTTGCTGGCGTTTTTCCATAGGC

TCCGCCCCCCTGACGAGCATCACAAAAATCGACGCTCAAGTCAGAGGTGG

CGAAACCCGACAGGACTATAAAGATACCAGGCGTTTCCCCCTGGAAGCTC

CCTCGTGCGCTCTCCTGTTCCGACCCTGCCGCTTACCGGATACCTGTCCG

CCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGA

ACCCCCCGTTCAGCCCGACCGCTGCGCCTTATCCGGTAACTATCGTCTTG

AGTCCAACCCGGTAAGACACGACTTATCGCCACTGGCAGCAGCCACTGGT

AACAGGATTAGCAGAGCGAGGTATGTAGGCGGTGCTACAGAGTTCTTGAA
```

```
GTGGTGGCCTAACTACGGCTACACTAGAAGGACAGTATTTGGTATCTGCG
CTCTGCTGAAGCCAGTTACCTTCGGAAAAAGAGTTGGTAGCTCTTGATCC
GGCAAACAAACCACCGCTGGTAGCGGTGGTTTTTTTGTTTGCAAGCAGCA
GATTACGCGCAGAAAAAAGGATCTCAAGAAGATCCTTTGATCTTTTCTA
CGGGGTCTGACGCTCAGTGGAACGAAAACTCACGTTAAGGGATTTTGGTC
ATGAGATTATCAAAAGGATCTTCACCTAGATCCTTTTAAATTAAAAATG
AAGTTTTAAATCAATCTAAAGTATATATGAGTAAACTTGGTCTGACAGTT
ACCAATGCTTAATCAGTGAGGCACCTATCTCAGCGATCTGTCTATTTCGT
TCATCCATAGTTGCCTGACTCCCCGTCGTGTAGATAACTACGATACGGGA
GGGCTTACCATCTGGCCCCAGTGCTGCAATGATACCGCGAGACCCACGCT
CACCGGCTCCAGATTTATCAGCAATAAACCAGCCAGCCGGAAGGGCCGAG
CGCAGAAGTGGTCCTGCAACTTTATCCGCCTCCATCCAGTCTATTAATTG
TTGCCGGGAAGCTAGAGTAAGTAGTTCGCCAGTTAATAGTTTGCGCAACG
TTGTTGCCATTGCTACAGGCATCGTGGTGTCACGCTCGTCGTTTGGTATG
GCTTCATTCAGCTCCGGTTCCCAACGATCAAGGCGAGTTACATGATCCCC
CATGTTGTGCAAAAAAGCGGTTAGCTCCTTCGGTCCTCCGATCGTTGTCA
GAAGTAAGTTGGCCGCAGTGTTATCACTCATGGTTATGGCAGCACTGCAT
AATTCTCTTACTGTCATGCCATCCGTAAGATGCTTTTCTGTGACTGGTGA
GTACTCAACCAAGTCATTCTGAGAATAGTGTATGCGGCGACCGAGTTGCT
CTTGCCCGGCGTCAATACGGGATAATACCGCGCCACATAGCAGAACTTTA
AAAGTGCTCATCATTGGAAAACGTTCTTCGGGGCGAAAACTCTCAAGGAT
CTTACCGCTGTTGAGATCCAGTTCGATGTAACCCACTCGTGCACCCAACT
GATCTTCAGCATCTTTTACTTTCACCAGCGTTTCTGGGTGAGCAAAAACA
GGAAGGCAAAATGCCGCAAAAAAGGGAATAAGGGCGACACGGAAATGTTG
AATACTCATACTCTTCCTTTTTCAATATTATTGAAGCATTTATCAGGGTT
ATTGTCTCATGAGCGGATACATATTTGAATGTATTTAGAAAAATAAACAA
ATAGGGGTTCCGCGCACATTTCCCCGAAAAGTGCCACCTGACGTCTAAGA
AACCATTATTATCATGACATTAACCTATAAAAATAGGCGTATCACGAGGC
CCTTTCGTCTCGCGCGTTTCGGTGATGACGGTGAAAACCTCTGACACATG
CAGCTCCCGGAGACGGTCACAGCTTGTCTGTAAGCGGATGCCGGGAGCAG
ACAAGCCCGTCAGGGCGCGTCAGCGGGTGTTGGCGGGTGTCGGGGCTGGC
TTAACTATGCGGCATCAGAGCAGATTGTACTGAGAGTGCACCATATATGC
GGTGTGAAATACCGCACAGATGCGTAAGGAGAAAATACCGCATCAGGCGC
CTCCTCAACCTGTATATTCGTAAACCACGCCCAATGGGAGCTGTCTCAGG
TTTGTTCCTGATTGGTTACGGCGCGTTTCGCATCATTGTTGAGTTTTTCC
GCCAGCCCGACGCGCAGTTTACCGGTGCCTGGGTGCAGTACATCAGCATG
GGGCAAATTCTTTCCATCCCGATGATTGTCGCGGGTGTGATCATGATGGT
CTGGGCATATCGTCGCAGCCCACAGCAACACGTTTCCTGAGGAACCATGA
AACAGTATTTAGAACTGATGCAAAAAGTGCTCGACGAAGGCACACAGAAA
AACGACCGTACCGGAACCGGAACGCTTTCCATTTTTGGTCATCAGATGCG
TTTTAACCTGCAAGATGGATTCCCGCTGGTGACAACTAAACGTTGCCACC
TGCGTTCCATCATCCATGAACTGCTGTGGTTTCTGCAGGGCGACACTAAC
ATTGCTTATCTACACGAAAACAATGTCACCATCTGGGACGAATGGGCCGA
TGAAACGGCGACCTCGGGCCAGTGTATGGTAAACAGTGGCGCGCCTGGC
CAACGCCAGATGGTCGTCATATTGACCAGATCACTACGGTACTGAACCAG
CTGAAAAACGACCCGGATTCGCGCCGCATTATTGTTTCAGCGTGGAACGT
AGGCGAACTGGATAAAATGGCGCTGGCACCGTGCCATGCATTCTTCCAGT
TCTATGTGGCAGACGGCAAACTCTCTTGCCAGCTTTATCAGCGCTCCTGT
GACGTCTTCCTCGGCCTGCCGTTCAACATTGCCAGCTACGCGTTATTGGT
GCATATGATGGCGCAGCAGTGCGATCTGGAAGTGGGTGATTTTGTCTGGA
CCGGTGGCGACACGCATCTGTACAGCAACCATATGGATCAAACTCATCTG
CAATTAAGCCGCGAACCGCGTCCGCTGCCGAAGTTGATTATCAAACGTAA
ACCCGAATCCATCTTCGACTACCGTTTCGAAGACTTTGAGATTGAAGGCT
ACGATCCGCATCCGGGCATTAAAGCGCCGGTGGCTATCTAATTACGAAAC
ATCCTGCCAGAGCCGACGCCAGTGTGCGTCGGTTTTTTTACCCTCCGTTA
AATTCTTCGAGACGCCTTCCCGAAGGCGCCATTCGCCATTCAGGCTGCGC
AACTGTTGGGAAGGGCGATCGGTGCGGGCCTCTTCGCTATTACGCCAGCT
GGCGAAAGGGGGATGTGCTGCAAGGCGATTAAGTTGGGTAACGCCAGGGT
TTTCCCAGTCACGACGTTGTAAAACGACGGCCAGTGCCAAGCTTTCTTTA
ATGAAGCAGGGCATCAGGACGGTATCTTTGTGGAGAAAGCAGAGTAATCT
TATTCAGCCTGACTGGTGGGAAACCACCAGTCAGAATGTGTTAGCGCATG
TTGACAAAAATACCATTAGTCACATTATCCGTCAGTCGGACGACATGGTA
GATAACCTGTTTATTATGCGTTTGATCTTACGTTTAATATTACCTTTAT
GCGATGAAACGGTCTTGGCTTTGATATTCATTTGGTCAGAGATTTGAATG
GTTCCCTGACCTGCCATCCACATTCGCAACATACTCGATTCGGTTCGGCT
CAATGATAACGTCGGCATATTTAAAAACGAGGTTATCGTTGTCTCTTTTT
TCAGAATATCGCCAAGGATATCGTCGAGAGATTCCGGTTTAATCGATTTA
GAACTGATCAATAAATTTTTTCTGACCAATAGATATTCATCAAAATGAAC
ATTGGCAATTGCCATAAAAACGATAAATAACGTATTGGGATGTTGATTAA
TGATGAGCTTGATACGCTGACTGTTAGAAGCATCGTGGATGAAACAGTCC
TCATTAATAAACACCACTGAAGGGCGCTGTGAATCACAAGCTATGGCAAG
GTCATCAACGGTTTCAATGTCGTTGATTTCTCTTTTTTTAACCCCTCTAC
TCAACAGATACCCGGTTAAACCTAGTCGGGTGTAACTACATAAATCCATA
ATAATCGTTGACATGGCATACCCTCACTCAATGCGTAACGATAATTCCCC
TTACCTGAATATTTCATCATGACTAAACGGAACAACATGGGTCACCTAAT
GCGCCACTCTCGCGATTTTTCAGGCGGACTTACTATCCCGTAAAGTGTTG
TATAATTTGCCTGGAATTGTCTTAAAGTAAAGTAAATGTTGCGATATGTG
AGTGAGCTTAAAACAAATATTTCGCTGCAGGAGTATCCTGGAAGATGTTC
GTgAGAAGCTTACTGCTCACAAGAAAAAGGCACGTCATCTGACGTGCCT
TTTTTATTTGTACTACCCTGTACGATTACTGCAGCTCGAGCTAACACGAG
CTATGTTTATCCACGTTTATCCAGTGATTGACTATGGGGATATAAGTATT
```

```
TTTTGGAGTTATATCGTACCAAGGAGTAGGATAAATAACAATCTGTGACG
CTGATGTACCTAAATAAGCCCCCCACCAACTAAAACTACTATTCGCTATA
ATATGATGGTTAGCTAAGCTCATTAACCATAAATCTTCTTCTTGTGATAA
ATCTTCTGAATAATATATATTATATTTTTTACTGAGTAATGTTTCGATAT
TTTCTTTACACCAAAAAATATCATCACTGAAAATAAACACGTCACGTATC
ATTGCCAAATCGCGTATTTTATTTAAAGCTTTTTTGTAATACTCTAACGA
ACAAACGCCATGAGTTAAAGTAGCTGTTTTGTTTTTTATATAATCTCCTC
TTCTTATATGAATAGAAAGTGATGATTGAGATTCAAGAATTTTTGCTGCA
AGTAAATTTGCTTGTTCAGACACATTCTTTGGAATAAAAAATTCTTTTAG
ATCTAATATATGTTTATGGAAAAAGTGCTCAGATTGCCAATACCCTATAT
ATTTTTTGGATTTCCATTTTTGCGCTATATATTCAAAATCATAACCATAG
GCATGAAATTCATTGCAAAAACCTAAAAAAAGAAAGATTTCAGGATATAA
TCTTGACCCACGAACCAAAAATTTATAAATATTATTAATTTTTGGTGTGT
AATACTGTAAATATTCCTCTGGAATTTGTAGATTGTTTAGCCTGTAACCA
CCATGATCATCATTTTCAGCATAATGACTTATATCAAAATATAATGGTGT
CCCATTAATTTTGGAAAGCGCATACCCAAATGAGAACTGAAAAAGTTGAT
TTCCAAGTCCGCCTTGTAATCTTATAATAGACATTATATCTCCTTCTTG
```

Figure 10:
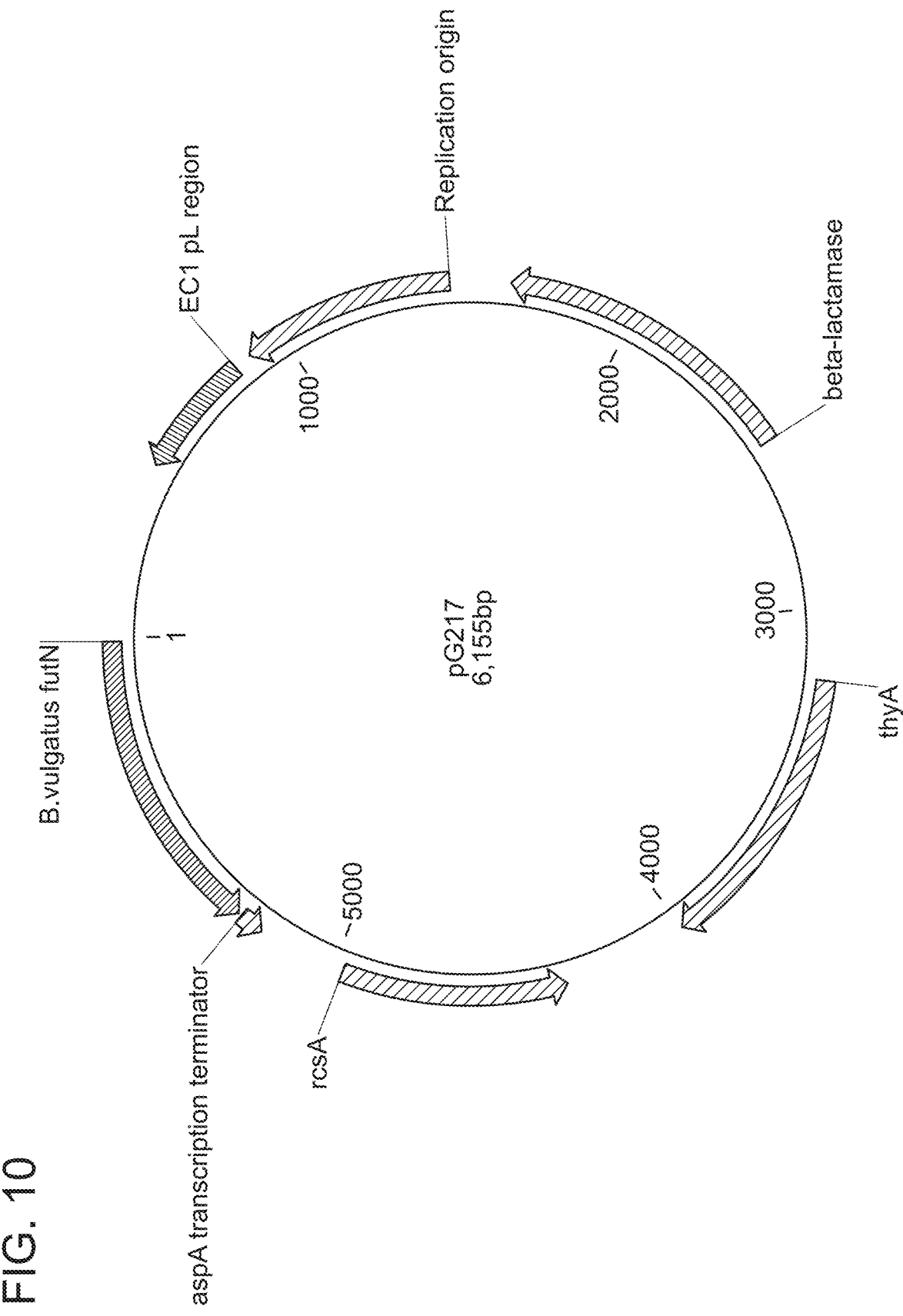
FIG. 10 is a diagram of plasmid pG216.

A map of plasmid pG216 is shown in FIG. 10. The sequence of plasmid pG216 is set forth below (SEQ ID NO: 17):

```
TCTAGAATTCTAAAAATTGATTGAATGTATGCAAATAAATGCATACACCA
TAGGTGTGGTTTAATTTGATGCCCTTTTTCAGGGCTGGAATGTGTAAGAG
CGGGGTTATTTATGCTGTTGTTTTTTTGTTACTCGGGAAGGGCTTTACCT
CTTCCGCATAAACGCTTCCATCAGCGTTTATAGTTAAAAAAATCTTTCGG
AACTGGTTTTGCGCTTACCCCAACCAACAGGGGATTTGCTGCTTTCCATT
GAGCCTGTTTCTCTGCGCGACGTTCGCGGCGGCGTGTTTGTGCATCCATC
TGGATTCTCCTGTCAGTTAGCTTTGGTGGTGTGTGGCAGTTGTAGTCCTG
AACGAAAACCCCCGCGATTGGCACATTGGCAGCTAATCCGGAATCGCAC
TTACGGCCAATGCTTCGTTTCGTATCACACACCCCAAAGCCTTCTGCTTT
GAATGCTGCCCTTCTTCAGGGCTTAATTTTTAAGAGCGTCACCTTCATGG
TGGTCAGTGCGTCCTGCTGATGTGCTCAGTATCACCGCCAGTGGTATTTA
TGTCAACACCGCCAGAGATAATTTATCACCGCAGATGGTTATCTGTATGT
TTTTTATATGAATTTATTTTTTGCAGGGGGGCATTGTTTGGTAGGTGAGA
GATCAATTCTGCATTAATGAATCGGCCAACGCGCGGGGAGAGGCGGTTTG
CGTATTGGGCGCTCTTCCGCTTCCTCGCTCACTGACTCGCTGCGCTCGGT
CGTTCGGCTGCGGCGAGCGGTATCAGCTCACTCAAAGGCGGTAATACGGT
TATCCACAGAATCAGGGGATAACGCAGGAAAGAACATGTGAGCAAAAGGC
CAGCAAAAGGCCAGGAACCGTAAAAAGGCCGCGTTGCTGGCGTTTTTCCA
TAGGCTCCGCCCCCCTGACGAGCATCACAAAAATCGACGCTCAAGTCAGA
GGTGGCGAAACCCGACAGGACTATAAAGATACCAGGCGTTTCCCCCTGGA
AGCTCCCTCGTGCGCTCTCCTGTTCCGACCCTGCCGCTTACCGGATACCT
GTCCGCCTTTCTCCCTTCGGGAAGCGTGGCGCTTTCTCATAGCTCACGCT
GTAGGTATCTCAGTTCGGTGTAGGTCGTTCGCTCCAAGCTGGGCTGTGTG
CACGAACCCCCCGTTCAGCCCGACCGCTGCGCCTTATCCGGTAACTATCG
TCTTGAGTCCAACCCGGTAAGACACGACTTATCGCCACTGGCAGCAGCCA
CTGGTAACAGGATTAGCAGAGCGAGGTATGTAGGCGGTGCTACAGAGTTC
TTGAAGTGGTGGCCTAACTACGGCTACACTAGAAGGACAGTATTTGGTAT
CTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAG
CAGCAGATTACGCGCAGAAAAAAAGGATCTCAAGAAGATCCTTTGATCTT
TTCTACGGGGTCTGACGCTCAGTGGAACGAAAACTCACGTTAAGGGATTT
TGGTCATGAGATTATCAAAAAGGATCTTCACCTAGATCCTTTTAAATTAA
AAATGAAGTTTTAAATCAATCTAAAGTATATATGAGTAAACTTGGTCTGA
CAGTTACCAATGCTTAATCAGTGAGGCACCTATCTCAGCGATCTGTCTAT
TTCGTTCATCCATAGTTGCCTGACTCCCCGTCGTGTAGATAACTACGATA
CGGGAGGGCTTACCATCTGGCCCCAGTGCTGCAATGATACCGCGAGACCC
ACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATT
AATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTG
GTATGGCTTCATTCAGCTCCGGTTCCCAACGATCAAGGCGAGTTACATGA
TCCCCCATGTTGTGCAAAAAAGCGGTTAGCTCCTTCGGTCCTCCGATCGT
TGTCAGAAGTAAGTTGGCCGCAGTGTTATCACTCATGGTTATGGCAGCAC
TGCATAATTCTCTTACTGTCATGCCATCCGTAAGATGCTTTTCTGTGACT
GGTGAGTACTCAACCAAGTCATTCTGAGAATAGTGTATGCGGCGACCGAG
TTGCTCTTGCCCGGCGTCAATACGGGATAATACCGCGCCACATAGCAGAA
CTTTAAAAGTGCTCATCATTGGAAAACGTTCTTCGGGGCGAAAACTCTCA
AGGATCTTACCGCTGTTGAGATCCAGTTCGATGTAACCCACTCGTGCACC
CAACTGATCTTCAGCATCTTTTACTTTCACCAGCGTTTCTGGGTGAGCAA
AAACAGGAAGGCAAAATGCCGCAAAAAAGGGAATAAGGGCGACACGGAAA
TGTTGAATACTCATACTCTTCCTTTTTCAATATTATTGAAGCATTTATCA
GGGTTATTGTCTCATGAGCGGATACATATTTGAATGTATTTAGAAAAATA
AACAAATAGGGGTTCCGCGCACATTTCCCCGAAAAGTGCCACCTGACGTC
TAAGAAACCATTATTATCATGACATTAACCTATAAAAATAGGCGTATCAC
GAGGCCCTTTCGTCTCGCGCGTTTCGGTGATGACGGTGAAAACCTCTGAC
ACATGCAGCTCCCGGAGACGGTCACAGCTTGTCTGTAAGCGGATGCCGGG
AGCAGACAAGCCCGTCAGGGCGCGTCAGCGGGTGTTGGCGGGTGTCGGG
CTGGCTTAACTATGCGGCATCAGAGCAGATTGTACTGAGAGTGCACCATA
TATGCGGTGTGAAATACCGCACAGATGCGTAAGGAGAAAATACCGCATCA
GGCGCCTCCTCAACCTGTATATTCGTAAACCACGCCCAATGGGAGCTGTC
TCAGGTTTGTTCCTGATTGGTTACGGCGCGTTTCGCATCATTGTTGAGTT
TTTCCGCCAGCCCGACGCGCAGTTTACCGGTGCCTGGGTGCAGTACATCA
```

```
GCATGGGGCAAATTCTTTCCATCCCGATGATTGTCGCGGGTGTGATCATG
ATGGTCTGGGCATATCGTCGCAGCCCACAGCAACACGTTTCCTGAGGAAC
CATGAAACAGTATTTAGAACTGATGCAAAAAGTGCTCGACGAAGGCACAC
AGAAAAACGACCGTACCGGAACCGGAACGCTTTCCATTTTTGGTCATCAG
ATGCGTTTTAACCTGCAAGATGGATTCCCGCTGGTGACAACTAAACGTTG
CCACCTGCGTTCCATCATCCATGAACTGCTGTGGTTTCTGCAGGGCGACA
CTAACATTGCTTATCTACACGAAAACAATGTCACCATCTGGGACGAATGG
GCCGATGAAAACGGCGACCTCGGGCCAGTGTATGGTAAACAGTGGCGCGC
CTGGCCAACGCCAGATGGTCGTCATATTGACCAGATCACTACGGTACTGA
ACCAGCTGAAAAACGACCCGGATTCGCGCCGCATTATTGTTTCAGCGTGG
AACGTAGGCGAACTGGATAAAATGGCGCTGGCACCGTGCCATGCATTCTT
CCAGTTCTATGTGGCAGACGGCAAACTCTCTTGCCAGCTTTATCAGCGCT
CCTGTGACGTCTTCCTCGGCCTGCCGTTCAACATTGCCAGCTACGCGTTA
TTGGTGCATATGATGGCGCAGCAGTGCGATCTGGAAGTGGGTGATTTTGT
CTGGACCGGTGGCGACACGCATCTGTACAGCAACCATATGGATCAAACTC
ATCTGCAATTAAGCCGCGAACCGCGTCCGCTGCCGAAGTTGATTATCAAA
CGTAAACCCGAATCCATCTTCGACTACCGTTTCGAAGACTTTGAGATTGA
AGGCTACGATCCGCATCCGGGCATTAAAGCGCCGGTGGCTATCTAATTAC
GAAACATCCTGCCAGAGCCGACGCCAGTGTGCGTCGGTTTTTTTACCCTC
CGTTAAATTCTTCGAGACGCCTTCCCGAAGGCGCCATTCGCCATTCAGGC
TGCGCAACTGTTGGGAAGGGCGATCGGTGCGGGCCTCTTCGCTATTACGC
CAGCTGGCGAAAGGGGGATGTGCTGCAAGGCGATTAAGTTGGGTAACGCC
AGGGTTTTCCCAGTCACGACGTTGTAAAACGACGGCCAGTGCCAAGCTTT
CTTTAATGAAGCAGGGCATCAGGACGGTATCTTTGTGGAGAAAGCAGAGT
AATCTTATTCAGCCTGACTGGTGGGAAACCACCAGTCAGAATGTGTTAGC
GCATGTTGACAAAAATACCATTAGTCACATTATCCGTCAGTCGGACGACA
TGGTAGATAACCTGTTTATTATGCGTTTTGATCTTACGTTTAATATTACC
TTTATGCGATGAAACGGTCTTGGCTTTGATATTCATTTGGTCAGAGATTT
GAATGGTTCCCTGACCTGCCATCCACATTCGCAACATACTCGATTCGGTT
CGGCTCAATGATAACGTCGGCATATTTAAAAACGAGGTTATCGTTGTCTC
TTTTTTCAGAATATCGCCAAGGATATCGTCGAGAGATTCCGGTTTAATCG
ATTTAGAACTGATCAATAAATTTTTTCTGACCAATAGATATTCATCAAAA
TGAACATTGGCAATTGCCATAAAAACGATAAATAACGTATTGGGATGTTG
ATTAATGATGAGCTTGATACGCTGACTGTTAGAAGCATCGTGGATGAAAC
AGTCCTCATTAATAAACACCACTGAAGGGCGCTGTGAATCACAAGCTATG
GCAAGGTCATCAACGGTTTCAATGTCGTTGATTTCTCTTTTTTAACCCC
TCTACTCAACAGATACCCGGTTAAACCTAGTCGGGTGTAACTACATAAAT
CCATAATAATCGTTGACATGGCATACCCTCACTCAATGCGTAACGATAAT
TCCCCTTACCTGAATATTTCATCATGACTAAACGGAACAACATGGGTCAC
CTAATGCGCCACTCTCGCGATTTTTCAGGCGGACTTACTATCCCGTAAAG
TGTTGTATAATTTGCCTGGAATTGTCTTAAAGTAAAGTAAATGTTGCGAT
ATGTGAGTGAGCTTAAAACAAATATTTCGCTGCAGGAGTATCCTGGAAGA
TGTTCGTAGAAGCTTACTGCTCACAAGAAAAAAGGCACGTCATCTGACGT
GCCTTTTTTATTTGTACTACCCTGTACGATTACTGCAGCTCGAGTTAGGA
TTTCGTTTCGAATTGGGATTCGATTTTAACCCAGTCTTTGCACAGGATGT
TTTCGTTACCGTAAATCCAGTGGGACGGACCAATGATAATTTTTTCCGGA
TTTTTGATCAGGTAGGCTGCCCACCAGGAGTAAGTGCTGTTAGTGATGAT
ACCGTGTTTGCAAGACTGCATCAGCATCATGTCCCAGTGGGCTGCACCAT
CACGCGTCGTCATGTCAACAAACGGGTAACCCAGATCCAGGTTCTGTACG
AATTCCAGATCCTCGCAGAACAGGAACAGTTCCAGATTTTGAACACGTTT
TGCCATATACGCAATGGCGCGCAGCTGGTAGGAGATGTCCAGCTGCCAGC
CCAGGCGCATGTAATCGCCACGGCGGATGTGAACGAACACAGAGTTTTTC
GCAGCCAGGATCTGGGACAGTTTACGAGAGTACTGTTCCGCGTGTTCGGT
CGGGTGAGGCAGGGTGAAAGTTTGTTTGATCAGAGGGGAGATATCTTCGA
AATAGCGCGGGTCCTGAAAGTAGCCATGGAAATACGCAATGCGGCTCGGT
TCAAACAGTTCCGGCATGTACTCGAATACAATTTCTTTGCTAACGCGGCC
CAGACCCATACGACGCAGTGCACCACGCACCAGACGCGGCAGGTTCTGCA
TGTGTGCCGCGGCGATCTGCTGGGCGGACGCACACTGCAGGTCGATCGGG
AACAGGTGCAGGCCCAGTTCACGGTTACCGTAATCGAACCAAGTGGTATC
CAGCAGTACCGGAATGTTCAGGTGAGTCTGCAGAGATTTAGCGAATGCGT
ACTGGAACATCTGGTTACCCAGGCCGCCGTGCACCTGAACGATTTTGAAA
TCCATTATATCTCCTTCTTG
```

Figure 11:
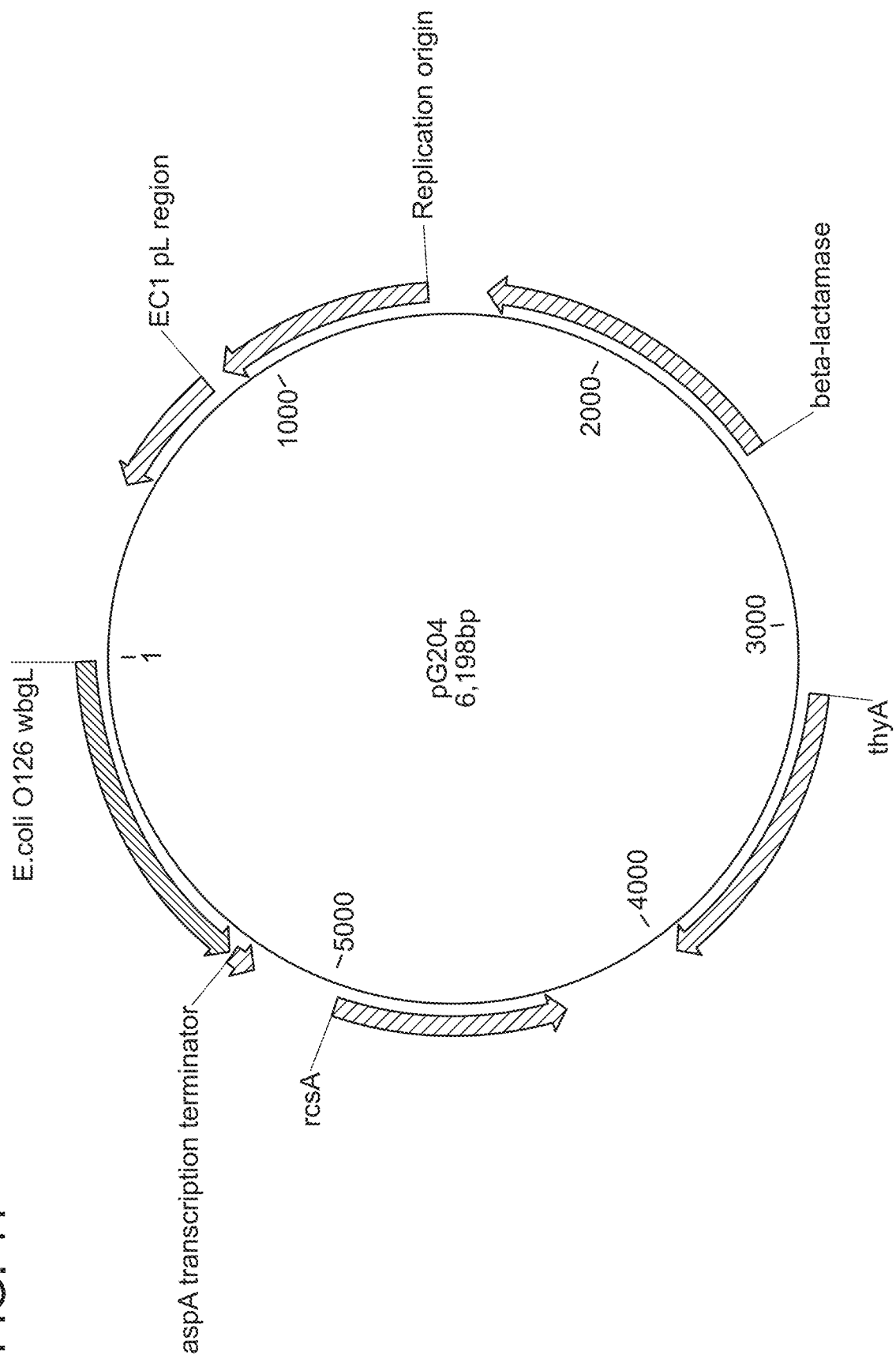
FIG. 11 is a diagram of plasmid pG217.

A map of plasmid pG217 is shown in FIG. 11. The sequence of plasmid pG217 is set forth below (SEQ ID NO: 18):

```
TCTAGAATTCTAAAAATTGATTGAATGTATGCAAATAAATGCATACACCA
TAGGTGTGGTTTAATTTGATGCCCTTTTTCAGGGCTGGAATGTGTAAGAG
CGGGGTTATTTATGCTGTTGTTTTTTTGTTACTCGGGAAGGGCTTTACCT
CTTCCGCATAAACGCTTCCATCAGCGTTTATAGTTAAAAAAATCTTTCGG
AACTGGTTTTGCGCTTACCCCAACCAACAGGGGATTTGCTGCTTTCCATT
GAGCCTGTTTCTCTGCGCGACGTTCGCGGCGGCGTGTTTGTGCATCCATC
TGGATTCTCCTGTCAGTTAGCTTTGGTGGTGTGTGGCAGTTGTAGTCCTG
AACGAAAACCCCCGCGATTGGCACATTGGCAGCTAATCCGGAATCGCAC
TTACGGCCAATGCTTCGTTTCGTATCACACACCCCAAAGCCTTCTGCTTT
GAATGCTGCCCTTCTTCAGGGCTTAATTTTTAAGAGCGTCACCTTCATGG
TGGTCAGTGCGTCCTGCTGATGTGCTCAGTATCACCGCCAGTGGTATTTA
TGTCAACACCGCCAGAGATAATTTATCACCGCAGATGGTTATCTGTATGT
TTTTTATATGAATTTATTTTTTGCAGGGGGGCATTGTTTGGTAGGTGAGA
GATCAATTCTGCATTAATGAATCGGCCAACGCGCGGGGAGAGGCGGTTTG
CGTATTGGGCGCTCTTCCGCTTCCTCGCTCACTGACTCGCTGCGCTCGGT
CGTTCGGCTGCGGCGAGCGGTATCAGCTCACTCAAAGGCGGTAATACGGT
```

```
TATCCACAGAATCAGGGGATAACGCAGGAAAGAACATGTGAGCAAAAGGC
CAGCAAAAGGCCAGGAACCGTAAAAAGGCCGCGTTGCTGGCGTTTTTCCA
TAGGCTCCGCCCCCTGACGAGCATCACAAAAATCGACGCTCAAGTCAGA
GGTGGCGAAACCCGACAGGACTATAAAGATACCAGGCGTTTCCCCCTGGA
AGCTCCCTCGTGCGCTCTCCTGTTCCGACCCTGCCGCTTACCGGATACCT
GTCCGCCTTTCTCCCTTCGGGAAGCGTGGCGCTTTCTCATAGCTCACGCT
GTAGGTATCTCAGTTCGGTGTAGGTCGTTCGCTCCAAGCTGGGCTGTGTG
CACGAACCCCCCGTTCAGCCCGACCGCTGCGCCTTATCCGGTAACTATCG
TCTTGAGTCCAACCCGGTAAGACACGACTTATCGCCACTGGCAGCAGCCA
CTGGTAACAGGATTAGCAGAGCGAGGTATGTAGGCGGTGCTACAGAGTTC
TTGAAGTGGTGGCCTAACTACGGCTACACTAGAAGGACAGTATTTGGTAT
CTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAG
CAGCAGATTACGCGCAGAAAAAAAGGATCTCAAGAAGATCCTTTGATCTT
TTCTACGGGGTCTGACGCTCAGTGGAACGAAAACTCACGTTAAGGGATTT
TGGTCATGAGATTATCAAAAAGGATCTTCACCTAGATCCTTTTAAATTAA
AAATGAAGTTTTAAATCAATCTAAAGTATATATGAGTAAACTTGGTCTGA
CAGTTACCAATGCTTAATCAGTGAGGCACCTATCTCAGCGATCTGTCTAT
TTCGTTCATCCATAGTTGCCTGACTCCCCGTCGTGTAGATAACTACGATA
CGGGAGGGCTTACCATCTGGCCCCAGTGCTGCAATGATACCGCGAGACCC
ACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATT
AATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTG
GTATGGCTTCATTCAGCTCCGGTTCCCAACGATCAAGGCGAGTTACATGA
TCCCCCATGTTGTGCAAAAAAGCGGTTAGCTCCTTCGGTCCTCCGATCGT
TGTCAGAAGTAAGTTGGCCGCAGTGTTATCACTCATGGTTATGGCAGCAC
TGCATAATTCTCTTACTGTCATGCCATCCGTAAGATGCTTTTCTGTGACT
GGTGAGTACTCAACCAAGTCATTCTGAGAATAGTGTATGCGGCGACCGAG
TTGCTCTTGCCCGGCGTCAATACGGGATAATACCGCGCCACATAGCAGAA
CTTTAAAAGTGCTCATCATTGGAAAACGTTCTTCGGGGCGAAAACTCTCA
AGGATCTTACCGCTGTTGAGATCCAGTTCGATGTAACCCACTCGTGCACC
CAACTGATCTTCAGCATCTTTTACTTTCACCAGCGTTTCTGGGTGAGCAA
AAACAGGAAGGCAAAATGCCGCAAAAAAGGGAATAAGGGCGACACGGAAA
TGTTGAATACTCATACTCTTCCTTTTTCAATATTATTGAAGCATTTATCA
GGGTTATTGTCTCATGAGCGGATACATATTTGAATGTATTTAGAAAAATA
AACAAATAGGGGTTCCGCGCACATTTCCCCGAAAAGTGCCACCTGACGTC
TAAGAAACCATTATTATCATGACATTAACCTATAAAAATAGGCGTATCAC
GAGGCCCTTTCGTCTCGCGCGTTTCGGTGATGACGGTGAAAACCTCTGAC
ACATGCAGCTCCCGGAGACGGTCACAGCTTGTCTGTAAGCGGATGCCGGG
AGCAGACAAGCCCGTCAGGGCGCGTCAGCGGGTGTTGGCGGGTGTCGGG
CTGGCTTAACTATGCGGCATCAGAGCAGATTGTACTGAGAGTGCACCATA
TATGCGGTGTGAAATACCGCACAGATGCGTAAGGAGAAAATACCGCATCA
GGCGCCTCCTCAACCTGTATATTCGTAAACCACGCCCAATGGGAGCTGTC
TCAGGTTTGTTCCTGATTGGTTACGGCGCGTTTCGCATCATTGTTGAGTT
TTTCCGCCAGCCCGACGCGCAGTTTACCGGTGCCTGGGTGCAGTACATCA
GCATGGGCAAATTCTTTCCATCCCGATGATTGTCGCGGGTGTGATCATG
ATGGTCTGGGCATATCGTCGCAGCCCACAGCAACACGTTTCCTGAGGAAC
CATGAAACAGTATTTAGAACTGATGCAAAAAGTGCTCGACGAAGGCACAC
AGAAAAACGACCGTACCGAACCGGAACGCTTTCCATTTTTGGTCATCAG
ATGCGTTTTAACCTGCAAGATGGATTCCCGCTGGTGACAACTAAACGTTG
CCACCTGCGTTCCATCATCCATGAACTGCTGTGGTTTCTGCAGGGCGACA
CTAACATTGCTTATCTACACGAAAACAATGTCACCATCTGGGACGAATGG
GCCGATGAAAACGGCGACCTCGGGCCAGTGTATGGTAAACAGTGGCGCGC
CTGGCCAACGCCAGATGGTCGTCATATTGACCAGATCACTACGGTACTGA
ACCAGCTGAAAAACGACCCGGATTCGCGCCGCATTATTGTTTCAGCGTGG
AACGTAGGCGAACTGGATAAAATGGCGCTGGCACCGTGCCATGCATTCTT
CCAGTTCTATGTGGCAGACGGCAAACTCTCTTGCCAGCTTTATCAGCGCT
CCTGTGACGTCTTCCTCGGCCTGCCGTTCAACATTGCCAGCTACGCGTTA
TTGGTGCATATGATGGCGCAGCAGTGCGATCTGGAAGTGGGTGATTTTGT
CTGGACCGGTGGCGACACGCATCTGTACAGCAACCATATGGATCAAACTC
ATCTGCAATTAAGCCGCGAACCGCGTCCGCTGCCGAAGTTGATTATCAAA
CGTAAACCCGAATCCATCTTCGACTACCGTTTCGAAGACTTTGAGATTGA
AGGCTACGATCCGCATCCGGGCATTAAAGCGCCGGTGGCTATCTAATTAC
GAAACATCCTGCCAGAGCCGACGCCAGTGTGCGTCGGTTTTTTTACCCTC
CGTTAAATTCTTCGAGACGCCTTCCCGAAGGCGCCATTCGCCATTCAGGC
TGCGCAACTGTTGGGAAGGGCGATCGGTGCGGGCCTCTTCGCTATTACGC
CAGCTGGCGAAAGGGGGATGTGCTGCAAGGCGATTAAGTTGGGTAACGCC
AGGGTTTTCCCAGTCACGACGTTGTAAAACGACGGCCAGTGCCAAGCTTT
CTTTAATGAAGCAGGGCATCAGGACGGTATCTTTGTGGAGAAAGCAGAGT
AATCTTATTCAGCCTGACTGGTGGGAAACCACCAGTCAGAATGTGTTAGC
GCATGTTGACAAAATACCATTAGTCACATTATCCGTCAGTCGGACGACA
TGGTAGATAACCTGTTTATTATGCGTTTGATCTTACGTTTAATATTACC
TTTATGCGATGAAACGGTCTTGGCTTTGATATTCATTTGGTCAGAGATTT
GAATGGTTCCCTGACCTGCCATCCACATTCGCAACATACTCGATTCGGTT
CGGCTCAATGATAACGTCGGCATATTTAAAAACGAGGTTATCGTTGTCTC
TTTTTTCAGAATATCGCCAAGGATATCGTCGAGAGATTCCGGTTTAATCG
ATTTAGAACTGATCAATAAATTTTTTCTGACCAATAGATATTCATCAAAA
TGAACATTGGCAATTGCCATAAAACGATAAATAACGTATTGGGATGTTG
ATTAATGATGAGCTTGATACGCTGACTGTTAGAAGCATCGTGGATGAAAC
AGTCCTCATTAATAAACACCACTGAAGGGCGCTGTGAATCACAAGCTATG
```

-continued

```
GCAAGGTCATCAACGGTTTCAATGTCGTTGATTTCTCTTTTTTAACCCC

TCTACTCAACAGATACCCGGTTAAACCTAGTCGGGTGTAACTACATAAAT

CCATAATAATCGTTGACATGGCATACCCTCACTCAATGCGTAACGATAAT

TCCCCTTACCTGAATATTTCATCATGACTAAACGGAACAACATGGGTCAC

CTAATGCGCCACTCTCGCGATTTTTCAGGCGGACTTACTATCCCGTAAAG

TGTTGTATAATTTGCCTGGAATTGTCTTAAAGTAAAGTAAATGTTGCGAT

ATGTGAGTGAGCTTAAAACAAATATTTCGCTGCAGGAGTATCCTGGAAGA

TGTTCGTAGAAGCTTACTGCTCACAAGAAAAAAGGCACGTCATCTGACGT

GCCTTTTTTATTTGTACTACCCTGTACGATTACTGCAGCTCGAGTTAGGA

TACCGGCACTTTGATCCAACCAGTCGGGTAGATATCCGGTGCTTCGGAGT

GCTGGAACCAACGGCTCGGCACAATAACAGTCTTATCCATATTAGGGTTC

AGCCAGGCACCCCACCAAGAAAACGTGCTGTTACAAATGATGTGATGTTT

GCAATGAGACATCAGCATCATATCCTGCCAGGAGTCTTCATCAGTGTTCC

AGTCAATATAAACCGCATTCTGCAGTGGCAGATTTTCTTTAACCCACGCG

ATATCGTCGGAGAAGATATAGTAAGATGGGCTAGCAACACGACGGGACAT

TTCCGCGATAGCATTCTGGTAATACGGCAGCTGGCACACGGAACCGGTAG

TAGCCCAGTGTTTCGGCTGCAGATAGTCACCACGACGAATGTGCAGGGAA

ACCGCGTTTTCATCTTTGTCCAGGATTTCCAGCATGTTCAGGCTGCGGGA

ATTTGCTTTGTTCTTATCAAAGGTGAAGGATTCACGCACTTCGTCTTTGA

TATCAGCGAAGAAACGCTCGCTCTGATAGAAACCTTTAAAGTACAGCAGC

GGCCAGAAATACTTCTTCTCGAACGCACGCAGAGAGTTCGGCGCCTGCTT

GCGTTCGTAGATTTTTTTAAAAAACAGGAATTCGATAACTTTTTTCAGCG

GTTGGTTGATGCAGAATTCGGTGTGCGGCAGGTTGAACACGCGGTGCATT

TCGTAACCGTAATGGACTTTGTAATGCATCATGTCGCTCAGGTCGATACG

GACCTTCGGGTAATACTTTTTCATACGCAGATAGAAAGCATAGATAAACA

TCTGGTTGCCCAGACCGCCAGTCACTTTGATCAGACGCATTATATCTCCT

TCTTG
```

Fucosylated oligosaccharides produced by metabolically engineered E. coli cells are purified from culture broth post-fermentation. An exemplary procedure comprises five steps. (1) Clarification: Fermentation broth is harvested and cells removed by sedimentation in a preparative centrifuge at 6000×g for 30 min. Each bioreactor run yields about 5-7 L of partially clarified supernatant. (2) Product capture on coarse carbon: A column packed with coarse carbon (Calgon 12×40 TR) of ~1000 ml volume (dimension 5 cm diameter× 60 cm length) is equilibrated with 1 column volume (CV) of water and loaded with clarified culture supernatant at a flow rate of 40 ml/min. This column has a total capacity of about 120 g of sugar. Following loading and sugar capture, the column is washed with 1.5 CV of water, then eluted with 2.5 CV of 50% ethanol or 25% isopropanol (lower concentrations of ethanol at this step (25-30%) may be sufficient for product elution.) This solvent elution step releases about 95% of the total bound sugars on the column and a small portion of the color bodies. In this first step capture of the maximal amount of sugar is the primary objective. Resolution of contaminants is not an objective. (3) Evaporation: A volume of 2.5 L of ethanol or isopropanol eluate from the capture column is rotary-evaporated at 56 C.° and a sugar syrup in water is generated. Alternative methods that could be used for this step include lyophilization or spray-drying. (4) Flash chromatography on fine carbon and ion exchange media: A column (GE Healthcare HiScale50/40, 5×40 cm, max pressure 20 bar) connected to a Biotage Isolera One FLASH Chromatography System is packed with 750 ml of a Darco Activated Carbon G60 (100-mesh): Celite 535 (coarse) 1:1 mixture (both column packings were obtained from Sigma). The column is equilibrated with 5 CV of water and loaded with sugar from step 3 (10-50 g, depending on the ratio of 2'-FL to contaminating lactose), using either a celite loading cartridge or direct injection. The column is connected to an evaporative light scattering (ELSD) detector to detect peaks of eluting sugars during the chromatography. A four-step gradient of isopropanol, ethanol or methanol is run in order to separate 2'-FL from monosaccharides (if present), lactose and color bodies. Fractions corresponding to sugar peaks are collected automatically in 120-ml bottles, pooled and directed to step 5. In certain purification runs from longer-than-normal fermentations, passage of the 2'-FL-containing fraction through anion-exchange and cation exchange columns can remove excess protein/DNA/caramel body contaminants. Resins tested successfully for this purpose are Dowex 22

Figure 4:
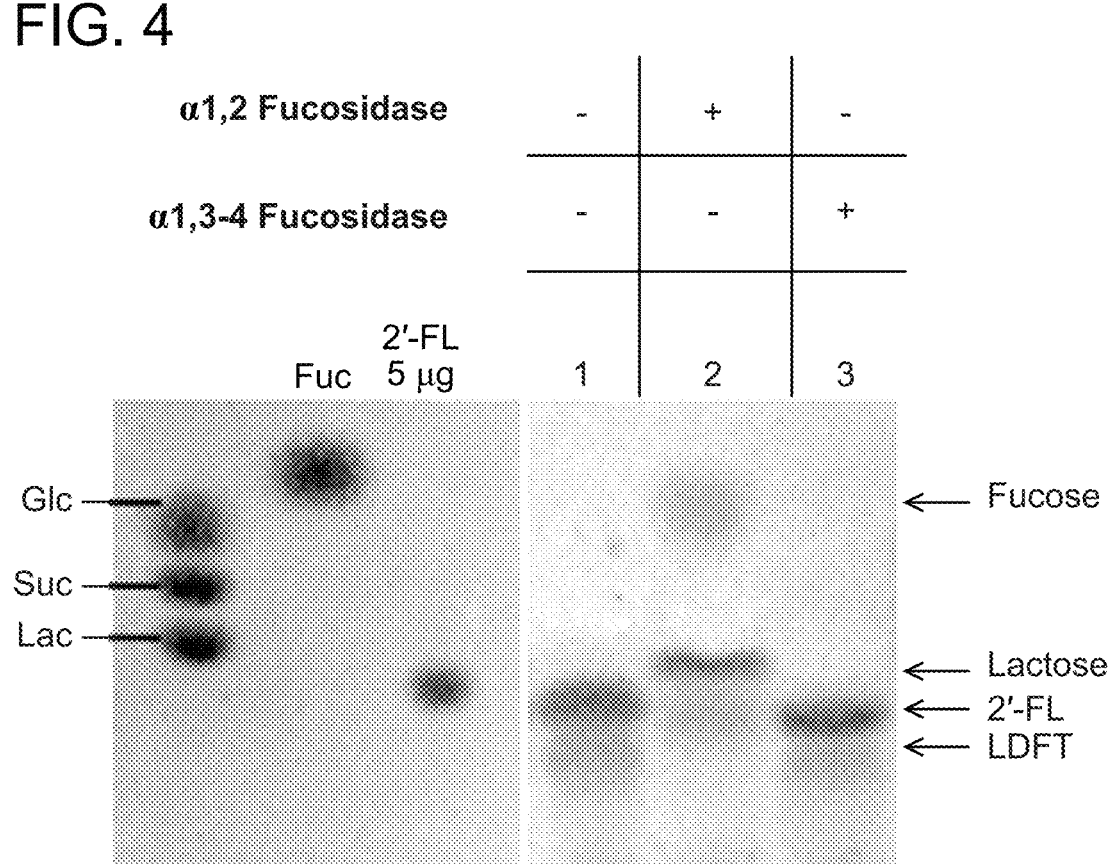
FIG. 4 is a chart and a photograph of thin layer chromatography analysis showing that fucosidase digestion confirms synthesis of bona fide 2'-FL by WbgL. Oligosaccharides produced by an *E. coli* strain expressing wbgL were isolated and subjected to overnight digestion with different fucosidases. Reaction products were analyzed by TLC. The production of fucose and lactose by treatment with α(1,2) fucosidase is illustrated in lane 2.
Figure 5:
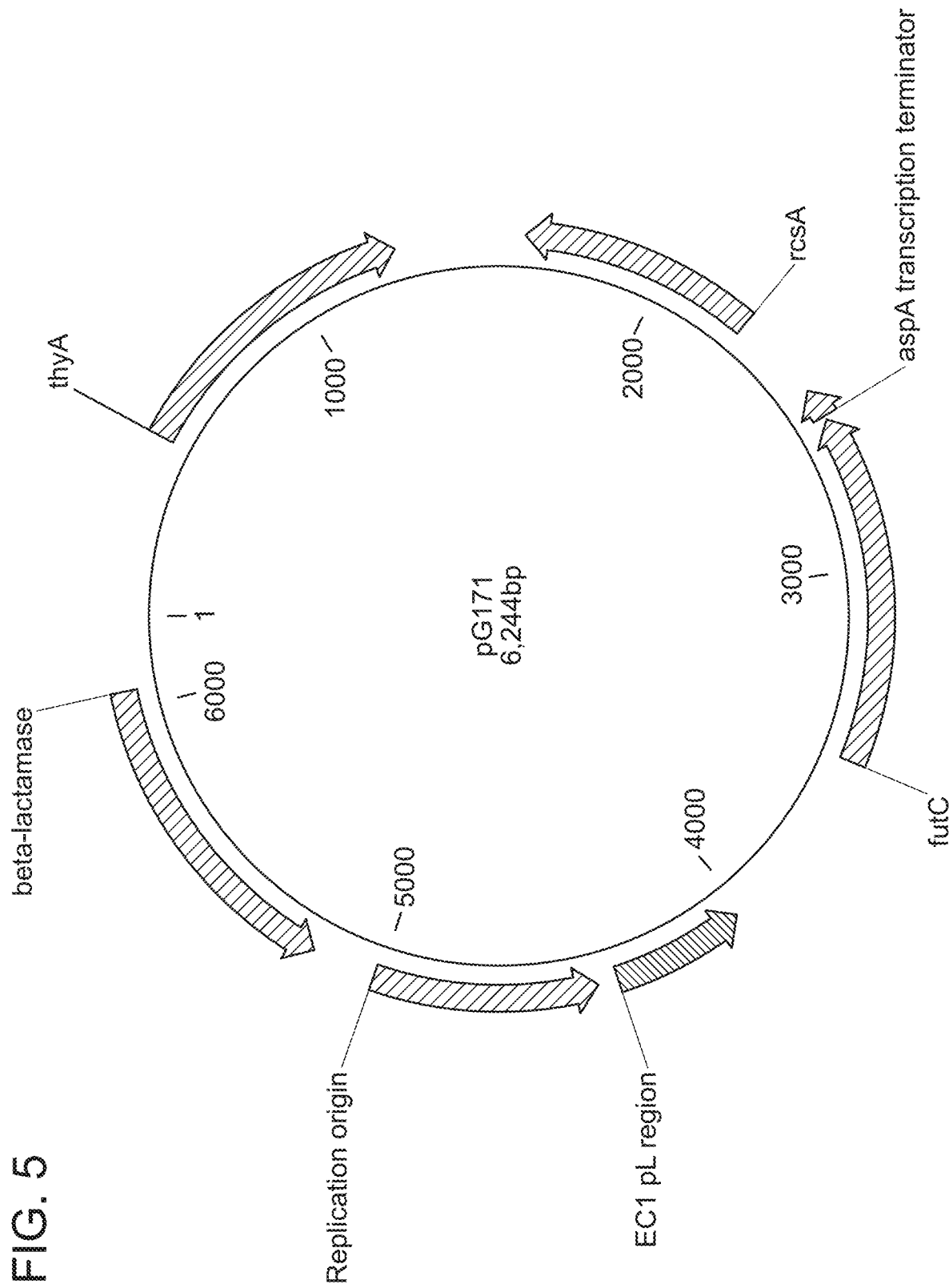
FIG. 5 is a diagram of plasmid pG171.

The identity of the major oligosaccharide synthesized by WbgL was tested and confirmed to be bona fide 2'-FL. Oligosaccharides synthesized in the WbgL strain were immobilized on a carbon column, eluted and resuspended in distilled water. This material was subjected to overnight digestion with fucosidases of different specificities, and the reactions were analyzed by TLC. As shown in FIG. 4, the untreated material consisted primarily of an oligosaccharide with the same mobility as the 2'-FL standard (lane 1). Treatment with α1,2 fucosidase yielded both lactose and fucose, while the presumptive 2'-FL spot was significantly diminished in staining intensity (lane 2). Treatment of the oligosaccharides with an α1,3-4 fucosidase had no effect. These results demonstrate that WbgL is capable of the biosynthesis of bona fide 2'-FL in metabolically engineered E. coli.

The gene screening approach was successfully utilized to identify new α(1,2) FTs for the efficient biosynthesis of 2'-FL in metabolically engineered E. coli host strains. The results of the screen are summarized in Table 1. Specifically, WbgL and FutL both direct the synthesis of 2'-FL at approximately 75% the levels attained by the previously characterized α(1,2) FT FutC. In addition, WbgL also was capable of synthesizing LDFT, which is another therapeutically useful HMO. Furthermore, FutN from the commensal enteric bacterium B. vulgatus was identified as another α(1,2) FT useful for the synthesis of fucosylated oligosaccharides. The approach described herein is useful in the analysis of additional candidate α(1,2) FTs and identifies additional enzymes that are useful for the large-scale production of HMOS.

Production Host Strains

E. coli K-12 is a well-studied bacterium which has been the subject of extensive research in microbial physiology and genetics and commercially exploited for a variety of industrial uses. The natural habitat of the parent species, E. coli, is the large bowel of mammals. E. coli K-12 has a history of safe use, and its derivatives are used in a large number of industrial applications, including the production of chemicals and drugs for human administration and consumption. E. coli K-12 was originally isolated from a convalescent diphtheria patient in 1922. Because it lacks virulence characteristics, grows readily on common laboratory media, and has been used extensively for microbial physiology and genetics research, it has become the standard bacteriological strain used in microbiological research, teaching, and production of products for industry and medicine. E. coli K-12 is now considered an enfeebled organism as a result of being maintained in the laboratory environment for over 70 years. As a result, K-12 strains are unable to colonize the intestines of humans and other animals under normal conditions. Additional information on this well known strain is available at http://epa.gov/oppt/biotech/pubs/fra/fra004.htm. In addition to E. coli K12, other bacterial strains are used as production host strains, e.g., a variety of bacterial species may be used in the oligosaccharide biosynthesis methods, e.g., Erwinia herbicola (Pantoea agglomerans), Citrobacter freundii, Pantoea citrea, Pectobacterium carotovorum, or Xanthomonas campestris. Bacteria of the genus Bacillus may also be used, including Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacillus cereus, and Bacillus circulans. Similarly, bacteria of the genera Lactobacillus and Lactococcus may be modified using the methods of this invention, including but not limited to Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii, and Lactococcus lactis, Streptococcus thermophiles and Proprionibacterium freudenreichii are also suitable bacterial species for the invention described herein. Also included as part of this invention are strains, modified as described here, from the genera Enterococcus (e.g., Enterococcus faecium and Enterococcus thermophiles), Bifidobacterium (e.g., Bifidobacterium longum, Bifidobacterium infantis, and Bifidobacterium bifidum), Sporolactobacillus spp., Micromomospora spp., Micrococcus spp., Rhodococcus spp., and Pseudomonas (e.g., Pseudomonas fluorescens and Pseudomonas aeruginosa).

Suitable host strains are amenable to genetic manipulation, e.g., they maintain expression constructs, accumulate precursors of the desired end product, e.g., they maintain pools of lactose and GDP-fucose, and accumulate endproduct, e.g., 2'-FL. Such strains grow well on defined minimal media that contains simple salts and generally a single carbon source. The strains engineered as described above to produce the desired fucosylated oligosaccharide(s) are grown in a minimal media. An exemplary minimal medium used in a bioreactor, minimal "FERM" medium, is detailed below.

Ferm (10 liters): Minimal medium comprising:
40 g $(NH_4)_2HPO_4$
100 g $KH_2PO_4$
10 g $MgSO_4.7H_2O$
40 g NaOH Trace elements:
1.3 g NTA (nitrilotriacetic acid)
0.5 g $FeSO_4.7H_2O$
0.09 g $MnCl_2.4H_2O$
0.09 g $ZnSO_4.7H_2O$
0.01 g $CoCl_2.6H_2O$
0.01 g $CuCl_2.2H_2O$
0.02 g $H_3BO_3$
0.01 g $Na_2MoO_4.2H_2O$ (pH 6.8)
Water to 10 liters
DF204 antifoam (0.1 ml/L)
150 g glycerol (initial batch growth), followed by fed batch mode with a 90% glycerol-1% $MgSO_4$-1× trace elements feed, at various rates for various times.

A suitable production host strain is one that is not the same bacterial strain as the source bacterial strain from which the fucosyltransferase-encoding nucleic acid sequence was identified. For example, the fucosyltransferase-encoding nucleic acid sequence FutL was identified in Helicobacter mustelae and a suitable host strain is a bacteria other than Helicobacter mustelae, e.g., FutL is produced in production host strain E. coli K12 or any of the other strains described above.

Bacteria comprising the characteristics described herein are cultured in the presence of lactose, and a fucosylated oligosaccharide is retrieved, either from the bacterium itself or from a culture supernatant of the bacterium. The fucosylated oligosaccharide is purified for use in therapeutic or nutritional products, or the bacteria are used directly in such products.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for producing a fucosylated oligosaccharide in a host bacterium comprising
providing said host bacterium comprising a genetic modification to reduce level of β-galactosidase activity, a defective colanic acid synthesis pathway, a mutation in an ATP-dependent intracellular protease, a mutation in a thyA gene, and an exogenous lactose-accepting α(1,2) fucosyltransferase gene from a genus consisting of Bacteroides;
culturing said host bacterium in the presence of lactose; and
retrieving the fucosylated oligosaccharide from said host bacterium or from a culture supernatant of said host bacterium, wherein less than 1% (w/w) of the level of the fucosylated oligosaccharide produced by said host bacterium is from 3-fucosyllactose (3-FL).

2. The method of claim 1, wherein said host bacterium comprises E. coli.

3. The method of claim 1, wherein said fucosylated oligosaccharide comprises 2'-fucosyllactose (2'-FL), lacto-difucotetraose (LDFT), Lacto-N-fucopentaose I (LNF I), or lacto-N-difucohexaose I (LDFH I).

4. The method of claim 1, wherein said method further comprises culturing said host bacterium in the presence of tryptophan and in the absence of thymidine.

5. The method of claim 2, wherein an endogenous lacZ gene and an endogenous lacI gene of said E. coli are deleted to reduce the level of β-galactosidase activity.

6. The method of claim 5, wherein said E. coli bacterium further comprises a lacIq gene promoter immediately upstream of a lacY gene.

7. The method of claim 2, wherein an endogenous wcaJ gene of said E. coli is deleted to inactivate the colanic acid synthesis pathway.

8. The method of claim 1, wherein said mutation in said ATP-dependent intracellular protease is a null mutation in a lon gene.

9. The method of claim 1, wherein said host bacterium accumulates intracellular lactose in the presence of exogenous lactose.

10. The method of claim 1, wherein said host bacterium accumulates intracellular guanosine diphosphate (GDP)-fucose.

11. The method of claim 1, wherein said exogenous lactose-accepting α(1,2) fucosyltransferase gene encodes an amino acid sequence comprising SEQ ID NO: 8 (FutN).

12. The method of claim 2, wherein said E. coli bacterium comprises the genotype characterized by $\Delta ampC::P_{trp}{}^{B}cI$, $\Delta(lacI-lacZ)::FRT$, $P_{lacIq}lacY^+$, $\Delta wcaJ::FRT$, thyA::Tn10, $\Delta lon:(npt3, lacZ^+)$, and $\Delta lacA$.

13. The method of claim 1, wherein the level of 3-FL produced by said host bacterium is less than 0.5% (w/w) of the level of the produced fucosylated oligosaccharide.

14. The method of claim 1, wherein said exogenous lactose-accepting α(1,2) fucosyltransferase gene is from a commensal microbe rather than a pathogen.

15. The method of claim 1, wherein said exogenous lactose-accepting α(1,2) fucosyltransferase gene is derived from Bacteroides vulgatus.

16. The method of claim 1, wherein said exogenous lactose-accepting (1,2) fucosyltransferase gene encodes a Bacteroides vulgatus glycosyl transferase family protein.

17. The method of claim 1, wherein said exogenous lactose-accepting α(1,2) fucosyltransferase gene encodes a Bacteroides vulgatus ATCC 8482 glycosyl transferase family protein.

18. The method of claim 1, wherein said exogenous lactose-accepting α(1,2) fucosyltransferase gene encodes a polypeptide having at least 10% identity at the amino acid level and less than about 40% to Helicobacter pylori 26695 α(1,2) fucosyltransferase (FutC).

19. The method of claim 1, wherein said exogenous lactose-accepting α(1,2) fucosyltransferase gene encodes a polypeptide having at least 20% identity at the amino acid level and less than about 40% to Helicobacter pylori 26695 α(1,2) fucosyltransferase (FutC).

20. The method of claim 1, wherein said exogenous lactose-accepting α(1,2) fucosyltransferase gene encodes a polypeptide having at least 20% identity at the amino acid level and less than about 30% to Helicobacter pylori 26695 α(1,2) fucosyltransferase (FutC).

21. The method of claim 1, wherein said exogenous lactose-accepting α(1,2) fucosyltransferase gene encodes a polypeptide having at least 20% identity at the amino acid level and less than about 25% to Helicobacter pylori 26695 α(1,2) fucosyltransferase (FutC).

22. The method of claim 1, wherein said exogenous lactose-accepting α(1,2) fucosyltransferase gene encodes a Bacteroides sp. lactose-accepting α(1,2) fucosyltransferase enzyme.

23. The method of claim 22, wherein said exogenous lactose-accepting α(1,2) fucosyltransferase gene encodes a Bacteroides vulgatus lactose-accepting α(1,2) fucosyltransferase enzyme.

24. The method of claim 22, wherein said exogenous lactose-accepting α(1,2) fucosyltransferase gene encodes a Bacteroides fragilis lactose-accepting α(1,2) fucosyltransferase enzyme.

25. The method of claim 1, wherein said exogenous lactose-accepting α(1,2) fucosyltransferase gene encodes a polypeptide having about 27% identity at the amino acid level to Helicobacter pylori 26695 α(1,2) fucosyltransferase (FutC).

26. A method for producing a fucosylated oligosaccharide in a host bacterium comprising
providing said host bacterium comprising a reduced level of β-galactosidase activity, a defective colanic acid synthesis pathway, a mutation in an ATP-dependent intracellular protease, a mutation in a thyA gene, and an exogenous lactose-accepting α(1,2) fucosyltransferase gene;
culturing said host bacterium in the presence of lactose; and
retrieving a fucosylated oligosaccharide from said host bacterium or from a culture supernatant of said host bacterium, wherein said exogenous lactose-accepting α(1,2) fucosyltransferase gene is from a bacterial strain consisting of Bacteroides vulgatus.

* * * * *

SEQUENCE LISTING

```
<160> NUMBER OF SEQ ID NOS: 18

<210> SEQ ID NO 1
<211> LENGTH: 6244
<212> TYPE: DNA
<213> ORGANISM: Artificial Sequence
<220> FEATURE:
```

<223> OTHER INFORMATION: plasmid pG171

<400> SEQUENCE: 1

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatatg cggtgtgaaa taccgcacag atgcgtaagg agaaaatacc gcatcaggcg     240
cctcctcaac ctgtatattc gtaaaccacg cccaatggga gctgtctcag gtttgttcct    300
gattggttac ggcgcgtttc gcatcattgt tgagttttc cgccagcccg acgcgcagtt     360
taccggtgcc tgggtgcagt acatcagcat ggggcaaatt ctttccatcc cgatgattgt    420
cgcgggtgtg atcatgatgg tctgggcata tcgtcgcagc ccacagcaac acgtttcctg    480
aggaaccatg aaacagtatt tagaactgat gcaaaaagtg ctcgacgaag gcacacagaa    540
aaacgaccgt accggaaccg gaacgctttc cattttttggt catcagatgc gttttaacct    600
gcaagatgga ttcccgctgg tgacaactaa acgttgccac ctgcgttcca tcatccatga    660
actgctgtgg tttctgcagg gcgacactaa cattgcttat ctacacgaaa acaatgtcac    720
catctgggac gaatgggccg atgaaaacgg cgacctcggg ccagtgtatg gtaaacagtg    780
gcgcgcctgg ccaacgccag atggtcgtca tattgaccag atcactacgg tactgaacca    840
gctgaaaaac gacccggatt cgcgccgcat tattgtttca gcgtggaacg taggcgaact    900
ggataaaatg gcgctggcac cgtgccatgc attcttccag ttctatgtgg cagacggcaa    960
actctcttgc cagctttatc agcgctcctg tgacgtcttc ctcggcctgc cgttcaacat   1020
tgccagctac gcgttattgg tgcatatgat ggcgcagcag tgcgatctgg aagtgggtga   1080
ttttgtctgg accggtggcg acacgcatct gtacagcaac catatggatc aaactcatct   1140
gcaattaagc cgcgaaccgc gtccgctgcc gaagttgatt atcaaacgta acccgaatc    1200
catcttcgac taccgtttcg aagactttga gattgaaggc tacgatccgc atccgggcat   1260
taaagcgccg gtggctatct aattacgaaa catcctgcca gagccgacgc cagtgtgcgt   1320
cggtttttt accctccgtt aaattcttcg agacgccttc ccgaaggcgc cattcgccat   1380
tcaggctgcg caactgttgg gaagggcgat cggtgcgggc ctcttcgcta ttacgccagc   1440
tggcgaaagg gggatgtgct gcaaggcgat taagttgggt aacgccaggg ttttcccagt   1500
cacgacgttg taaaacgacg gccagtgcca agctttcttt aatgaagcag ggcatcagga   1560
cggtatcttt gtggagaaag cagagtaatc ttattcagcc tgactggtgg gaaaccacca   1620
gtcagaatgt gttagcgcat gttgacaaaa ataccattag tcacattatc cgtcagtcgg   1680
acgacatggt agataacctg tttattatgc gttttgatct tacgtttaat attaccttta   1740
tgcgatgaaa cggtcttggc tttgatattc atttggtcag agatttgaat ggttccctga   1800
cctgccatcc acattcgcaa catactcgat tcggttcggc tcaatgataa cgtcggcata   1860
tttaaaaacg aggttatcgt tgtctctttt ttcagaatat cgccaaggat atcgtcgaga   1920
gattccggtt taatcgattt agaactgatc aataaatttt ttctgaccaa tagatattca   1980
tcaaaatgaa cattggcaat tgccataaaa acgataaata acgtattggg atgttgatta   2040
atgatgagct tgatacgctg actgttagaa gcatcgtgga tgaaacagtc ctcattaata   2100
aacaccactg aagggcgctg tgaatcacaa gctatggcaa ggtcatcaac ggtttcaatg   2160
tcgttgattt ctcttttttt aaccccctcta ctcaacagat accggttaa acctagtcgg   2220
gtgtaactac ataaatccat aataatcgtt gacatggcat accctcactc aatgcgtaac   2280
```

```
gataattccc cttacctgaa tatttcatca tgactaaacg gaacaacatg ggtcaccctaa    2340 tgcgccactc tcgcgatttt tcaggcggac ttactatccc gtaaagtgtt gtataatttg    2400
cctggaattg tcttaaagta aagtaaatgt tgcgatatgt gagtgagctt aaaacaaata    2460
tttcgctgca ggagtatcct ggaagatgtt cgtagaagct tactgctcac aagaaaaaag    2520
gcacgtcatc tgacgtgcct tttttatttg tactaccctg tacgattact gcagctcgag    2580
tttaattcaa atcttcttca gaaatcaatt tttgttcagc gttatacttt tgggatttta    2640
cctcaaaatg ggattctatt ttcacccact ccttacaaag atattctca tgcccaaaaa    2700 gccagtgttt ggggccaata atgattttt ctggattttc tatcaaatag ccgcccacc    2760 agctataagt gctattagcg ataatgccat gctgacaaga ttgcatgagc agcatgtccc    2820
aatacgcctc ttcttcttta tccctagtgg tcatgtccat aaaagggtag ccaagatcaa    2880
gattttgcgt gaattctaag tcttcgcaaa acacaaaaag ctccatgttt ggcacgcgct    2940
ttgccatata ctcaagcgcc ttttttgat agtcaatacc aagctgacag ccaatcccca    3000
cataatcccc tcttcttata tgcacaaaca cgctgttttt agcggctaaa atcaaagaaa    3060
gcttgcactg atattcttcc tctttttat tattattctt attatttcg ggtggtggtg    3120 gtagagtgaa ggtttgcttg attaaagggg atatagcatc aaagtatcgt ggatcttgga    3180
aatagccaaa aaaataagtc aagcggcttg gctttagcaa tttaggctcg tattcaaaaa    3240
cgatttcttg actcacccta tcaaatccca tgcatttgag cgcgtctctt actagcttgg    3300
ggaggtgttg cattttagct atagcgattt ctttcgcgct cgcatagggc aaatcaatag    3360
ggaaaagttc taattgcatt ttcctatcgc tccaatcaaa agaagtgata tctaacagca    3420
caggcgtatt agagtgtttt tgcaaacttt tagcgaaagc gtattgaaac atttgattcc    3480
caagccctcc gcaaatttgc accaccttaa aagccatatg tatatctcct tcttgaattc    3540
taaaaattga ttgaatgtat gcaaataaat gcatacacca taggtgtggt ttaatttgat    3600 gcccttttc agggctggaa tgtgtaagag cggggttatt tatgctgttg ttttttttgtt    3660 actcgggaag ggctttacct cttccgcata acgcttcca tcagcgttta tagttaaaaa    3720
aatctttcgg aactggtttt gcgcttaccc caaccaacag gggatttgct gctttccatt    3780
gagcctgttt ctctgcgcga cgttcgcggc ggcgtgtttg tgcatccatc tggattctcc    3840
tgtcagttag ctttggtggt gtgtggcagt tgtagtcctg aacgaaaacc ccccgcgatt    3900
ggcacattgg cagctaatcc ggaatcgcac ttacggccaa tgcttcgttt cgtatcacac    3960
accccaaagc cttctgcttt gaatgctgcc cttcttcagg gcttaatttt taagagcgtc    4020
accttcatgg tggtcagtgc gtcctgctga tgtgctcagt atcaccgcca gtggtattta    4080
tgtcaacacc gccagagata atttatcacc gcagatggtt atctgtatgt ttttttatatg    4140 aatttatttt ttgcaggggg gcattgtttg gtaggtgaga atcaattct gcattaatga    4200 atcggccaac gcgcggggag aggcggtttg cgtattgggc gctcttccgc ttcctcgctc    4260
actgactcgc tgcgctcggt cgttcggctg cggcgagcgg tatcagctca ctcaaaggcg    4320
gtaatacggt tatccacaga atcagggat aacgcaggaa agaacatgtg agcaaaaggc    4380
cagcaaaagg ccaggaaccg taaaaaggcc gcgttgctgg cgttttttcca taggctccgc    4440 ccccctgacg agcatcacaa aaatcgacgc tcaagtcaga ggtggcgaaa cccgacagga    4500
ctataaagat accaggcgtt tcccctgga agctccctcg tgcgctctcc tgttccgacc    4560
ctgccgctta ccggatacct gtccgccttt ctcccttcgg gaagcgtggc gctttctcat    4620
```

-continued

```
agctcacgct gtaggtatct cagttcggtg taggtcgttc gctccaagct gggctgtgtg    4680
cacgaacccc ccgttcagcc cgaccgctgc gccttatccg gtaactatcg tcttgagtcc    4740
aacccggtaa gacacgactt atcgccactg gcagcagcca ctggtaacag gattagcaga    4800
gcgaggtatg taggcggtgc tacagagttc ttgaagtggt ggcctaacta cggctacact    4860
agaaggacag tatttggtat ctgcgctctg ctgaagccag ttaccttcgg aaaaagagtt    4920
ggtagctctt gatccggcaa acaaaccacc gctggtagcg gtggttttt tgtttgcaag    4980
cagcagatta cgcgcagaaa aaaggatct caagaagatc ctttgatctt ttctacgggg    5040
tctgacgctc agtggaacga aaactcacgt taagggattt tggtcatgag attatcaaaa    5100
aggatcttca cctagatcct tttaaattaa aaatgaagtt ttaaatcaat ctaaagtata    5160
tatgagtaaa cttggtctga cagttaccaa tgcttaatca gtgaggcacc tatctcagcg    5220
atctgtctat ttcgttcatc catagttgcc tgactccccg tcgtgtagat aactacgata    5280
cgggagggct taccatctgg ccccagtgct gcaatgatac cgcgagaccc acgctcaccg    5340
gctccagatt tatcagcaat aaaccagcca gccggaaggg ccgagcgcag aagtggtcct    5400
gcaactttat ccgcctccat ccagtctatt aattgttgcc gggaagctag agtaagtagt    5460
tcgccagtta atagtttgcg caacgttgtt gccattgcta caggcatcgt ggtgtcacgc    5520
tcgtcgtttg gtatggcttc attcagctcc ggttcccaac gatcaaggcg agttacatga    5580
tcccccatgt tgtgcaaaaa agcggttagc tccttcggtc ctccgatcgt tgtcagaagt    5640
aagttggccg cagtgttatc actcatggtt atggcagcac tgcataattc tcttactgtc    5700
atgccatccg taagatgctt ttctgtgact ggtgagtact caaccaagtc attctgagaa    5760
tagtgtatgc ggcgaccgag ttgctcttgc ccggcgtcaa tacgggataa taccgcgcca    5820
catagcagaa ctttaaaagt gctcatcatt ggaaaacgtt cttcggggcg aaaactctca    5880
aggatcttac cgctgttgag atccagttcg atgtaaccca ctcgtgcacc caactgatct    5940
tcagcatctt ttactttcac cagcgtttct gggtgagcaa aaacaggaag gcaaaatgcc    6000
gcaaaaaagg gaataagggc gacacggaaa tgttgaatac tcatactctt cctttttcaa    6060
tattattgaa gcatttatca gggttattgt ctcatgagcg gatacatatt tgaatgtatt    6120
tagaaaaata aacaaatagg ggttccgcgc acatttcccc gaaaagtgcc acctgacgtc    6180
taagaaacca ttattatcat gacattaacc tataaaaata ggcgtatcac gaggcccttt    6240
cgtc                                                                 6244
```

<210> SEQ ID NO 2
<211> LENGTH: 298
<212> TYPE: PRT
<213> ORGANISM: Helicobacter pylori

<400> SEQUENCE: 2

```
Met Ala Phe Lys Val Val Gln Ile Cys Gly Gly Leu Gly Asn Gln Met
1               5                   10                  15

Phe Gln Tyr Ala Phe Ala Lys Ser Leu Gln Lys His Leu Asn Thr Pro
            20                  25                  30

Val Leu Leu Asp Ile Thr Ser Phe Asp Trp Ser Asn Arg Lys Met Gln
        35                  40                  45

Leu Glu Leu Phe Pro Ile Asp Leu Pro Tyr Ala Ser Ala Lys Glu Ile
    50                  55                  60

Ala Ile Ala Lys Met Gln His Leu Pro Lys Leu Val Arg Asp Thr Leu
65                  70                  75                  80
```

```
Lys Cys Met Gly Phe Asp Arg Val Ser Gln Glu Ile Val Phe Glu Tyr
                85                  90                  95

Glu Pro Gly Leu Leu Lys Pro Ser Arg Leu Thr Tyr Phe Tyr Gly Tyr
            100                 105                 110

Phe Gln Asp Pro Arg Tyr Phe Asp Ala Ile Ser Pro Leu Ile Lys Gln
        115                 120                 125

Thr Phe Thr Leu Pro Pro Glu Asn Gly Asn Asn Lys Lys Lys Glu
    130                 135                 140

Glu Glu Tyr His Arg Lys Leu Ala Leu Ile Leu Ala Ala Lys Asn Ser
145                 150                 155                 160

Val Phe Val His Val Arg Arg Gly Asp Tyr Val Gly Ile Gly Cys Gln
                165                 170                 175

Leu Gly Ile Asp Tyr Gln Lys Lys Ala Leu Glu Tyr Ile Ala Lys Arg
            180                 185                 190

Val Pro Asn Met Glu Leu Phe Val Phe Cys Glu Asp Leu Lys Phe Thr
        195                 200                 205

Gln Asn Leu Asp Leu Gly Tyr Pro Phe Met Asp Met Thr Thr Arg Asp
    210                 215                 220

Lys Glu Glu Glu Ala Tyr Trp Asp Met Leu Leu Met Gln Ser Cys Lys
225                 230                 235                 240

His Gly Ile Ile Ala Asn Ser Thr Tyr Ser Trp Ala Ala Tyr Leu
                245                 250                 255

Ile Asn Asn Pro Glu Lys Ile Ile Gly Pro Lys His Trp Leu Phe
            260                 265                 270

Gly His Glu Asn Ile Leu Cys Lys Glu Trp Val Lys Ile Glu Ser His
        275                 280                 285

Phe Glu Val Lys Ser Lys Lys Tyr Asn Ala
    290                 295

<210> SEQ ID NO 3
<211> LENGTH: 281
<212> TYPE: PRT
<213> ORGANISM: Vibrio cholerae

<400> SEQUENCE: 3

Met Ile Val Met Lys Ile Ser Gly Gly Leu Gly Asn Gln Leu Phe Gln
1               5                   10                  15

Tyr Ala Val Gly Arg Ala Ile Ala Ile Gln Tyr Gly Val Pro Leu Lys
            20                  25                  30

Leu Asp Val Ser Ala Tyr Lys Asn Tyr Lys Leu His Asn Gly Tyr Arg
        35                  40                  45

Leu Asp Gln Phe Asn Ile Asn Ala Asp Ile Ala Asn Glu Asp Glu Ile
    50                  55                  60

Phe His Leu Lys Gly Ser Ser Asn Arg Leu Ser Arg Ile Leu Arg Arg
65                  70                  75                  80

Leu Gly Trp Leu Lys Lys Asn Thr Tyr Tyr Ala Glu Lys Gln Arg Thr
                85                  90                  95

Ile Tyr Asp Val Ser Val Phe Met Gln Ala Pro Arg Tyr Leu Asp Gly
            100                 105                 110

Tyr Trp Gln Asn Glu Gln Tyr Phe Ser Gln Ile Arg Ala Val Leu Leu
        115                 120                 125

Gln Glu Leu Trp Pro Asn Gln Pro Leu Ser Ile Asn Ala Gln Ala His
    130                 135                 140

Gln Ile Lys Ile Gln Gln Thr His Ala Val Ser Ile His Val Arg Arg
145                 150                 155                 160
```

```
Gly Asp Tyr Leu Asn His Pro Glu Ile Gly Val Leu Asp Ile Asp Tyr
                165                 170                 175

Tyr Lys Arg Ala Val Asp Tyr Ile Lys Glu Lys Ile Glu Ala Pro Val
            180                 185                 190

Phe Phe Val Phe Ser Asn Asp Val Ala Trp Cys Lys Asp Asn Phe Asn
        195                 200                 205

Phe Ile Asp Ser Pro Val Phe Ile Glu Asp Thr Gln Thr Glu Ile Asp
    210                 215                 220

Asp Leu Met Leu Met Cys Gln Cys Gln His Asn Ile Val Ala Asn Ser
225                 230                 235                 240

Ser Phe Ser Trp Trp Ala Ala Trp Leu Asn Ser Asn Val Asp Lys Ile
                245                 250                 255

Val Ile Ala Pro Lys Thr Trp Met Ala Glu Asn Pro Lys Gly Tyr Lys
            260                 265                 270

Trp Val Pro Asp Ser Trp Arg Glu Ile
        275                 280

<210> SEQ ID NO 4
<211> LENGTH: 297
<212> TYPE: PRT
<213> ORGANISM: Escherichia coli

<400> SEQUENCE: 4

Met Ser Ile Ile Arg Leu Gln Gly Gly Leu Gly Asn Gln Leu Phe Gln
1               5                   10                  15

Phe Ser Phe Gly Tyr Ala Leu Ser Lys Ile Asn Gly Thr Pro Leu Tyr
            20                  25                  30

Phe Asp Ile Ser His Tyr Ala Glu Asn Asp Asp His Gly Gly Tyr Arg
        35                  40                  45

Leu Asn Asn Leu Gln Ile Pro Glu Glu Tyr Leu Gln Tyr Tyr Thr Pro
    50                  55                  60

Lys Ile Asn Asn Ile Tyr Lys Phe Leu Val Arg Gly Ser Arg Leu Tyr
65                  70                  75                  80

Pro Glu Ile Phe Leu Phe Leu Gly Phe Cys Asn Glu Phe His Ala Tyr
                85                  90                  95

Gly Tyr Asp Phe Glu Tyr Ile Ala Gln Lys Trp Lys Ser Lys Lys Tyr
            100                 105                 110

Ile Gly Tyr Trp Gln Ser Glu His Phe Phe His Lys His Ile Leu Asp
        115                 120                 125

Leu Lys Glu Phe Phe Ile Pro Lys Asn Val Ser Glu Gln Ala Asn Leu
    130                 135                 140

Leu Ala Ala Lys Ile Leu Glu Ser Gln Ser Ser Leu Ser Ile His Ile
145                 150                 155                 160

Arg Arg Gly Asp Tyr Ile Lys Asn Lys Thr Ala Thr Leu Thr His Gly
                165                 170                 175

Val Cys Ser Leu Glu Tyr Tyr Lys Lys Ala Leu Asn Lys Ile Arg Asp
            180                 185                 190

Leu Ala Met Ile Arg Asp Val Phe Ile Phe Ser Asp Asp Ile Phe Trp
        195                 200                 205

Cys Lys Glu Asn Ile Glu Thr Leu Leu Ser Lys Lys Tyr Asn Ile Tyr
    210                 215                 220

Tyr Ser Glu Asp Leu Ser Gln Glu Glu Asp Leu Trp Leu Met Ser Leu
225                 230                 235                 240

Ala Asn His His Ile Ile Ala Asn Ser Ser Phe Ser Trp Trp Gly Ala
```

```
                        245                 250                 255
Tyr Leu Gly Thr Ser Ala Ser Gln Ile Val Ile Tyr Pro Thr Pro Trp
            260                 265                 270

Tyr Asp Ile Thr Pro Lys Asn Thr Tyr Ile Pro Ile Val Asn His Trp
            275                 280                 285

Ile Asn Val Asp Lys His Ser Ser Cys
            290                 295

<210> SEQ ID NO 5
<211> LENGTH: 293
<212> TYPE: PRT
<213> ORGANISM: Helicobacter bilis

<400> SEQUENCE: 5

Met Gly Asp Tyr Lys Ile Val Glu Leu Thr Cys Gly Leu Gly Asn Gln
1               5                   10                  15

Met Phe Gln Tyr Ala Phe Ala Lys Ala Leu Gln Lys His Leu Gln Val
            20                  25                  30

Pro Val Leu Leu Asp Lys Thr Trp Tyr Asp Thr Gln Asp Asn Ser Thr
        35                  40                  45

Gln Phe Ser Leu Asp Ile Phe Asn Val Asp Leu Glu Tyr Ala Thr Asn
    50                  55                  60

Thr Gln Ile Glu Lys Ala Lys Ala Arg Val Ser Lys Leu Pro Gly Leu
65                  70                  75                  80

Leu Arg Lys Met Phe Gly Leu Lys Lys His Asn Ile Ala Tyr Ser Gln
                85                  90                  95

Ser Phe Asp Phe His Asp Glu Tyr Leu Leu Pro Asn Asp Phe Thr Tyr
            100                 105                 110

Phe Ser Gly Phe Phe Gln Asn Ala Lys Tyr Leu Lys Gly Leu Glu Gln
        115                 120                 125

Glu Leu Lys Ser Ile Phe Tyr Tyr Asp Ser Asn Asn Phe Ser Asn Phe
    130                 135                 140

Gly Lys Gln Arg Leu Glu Leu Ile Leu Gln Ala Lys Asn Ser Ile Phe
145                 150                 155                 160

Ile His Ile Arg Arg Gly Asp Tyr Cys Lys Ile Gly Trp Glu Leu Gly
                165                 170                 175

Met Asp Tyr Tyr Lys Arg Ala Ile Gln Tyr Ile Met Asp Arg Val Glu
            180                 185                 190

Glu Pro Lys Phe Phe Ile Phe Gly Ala Thr Asp Met Ser Phe Thr Glu
        195                 200                 205

Gln Phe Gln Lys Asn Leu Gly Leu Asn Glu Asn Asn Ser Ala Asn Leu
    210                 215                 220

Ser Glu Lys Thr Ile Thr Gln Asp Asn Gln His Glu Asp Met Phe Leu
225                 230                 235                 240

Met Cys Tyr Cys Lys His Ala Ile Leu Ala Asn Ser Ser Tyr Ser Phe
                245                 250                 255

Trp Ser Ala Tyr Leu Asn Asn Asp Ala Asn Asn Ile Val Ile Ala Pro
            260                 265                 270

Thr Pro Trp Leu Leu Asp Asn Asp Asn Ile Ile Cys Asp Asp Trp Ile
        275                 280                 285

Lys Ile Ser Ser Lys
    290

<210> SEQ ID NO 6
<211> LENGTH: 257
```

```
<212> TYPE: PRT
<213> ORGANISM: Helicobacter cinaedi

<400> SEQUENCE: 6

Met Leu Phe Pro Phe Lys Phe Ile Tyr Asn Arg Leu Arg Tyr Lys Ala
1               5                   10                  15

Ile Arg Leu Ile Arg Arg Ala Ser Tyr Arg Pro Phe Tyr Glu Phe
            20                  25                  30

Tyr Ala His Ile Val Trp Gly Glu Gly Val Val Asn Asp Arg Ile
        35                  40                  45

Met Lys His Tyr Arg Glu Ser Ser Phe Lys Pro Tyr Ala Phe Pro Tyr
    50                  55                  60

Gly Ile Asn Met Ser Phe Val Tyr Ser Asn Asp Val Tyr Ala Leu Leu
65                  70                  75                  80

Lys Asp Asp Phe Arg Leu Lys Ile Pro Leu Arg Tyr Asp Asn Ala Met
                85                  90                  95

Leu Lys Lys Gln Ile Gln Asn Thr Asp Lys Ser Val Phe Leu His Ile
            100                 105                 110

Arg Arg Gly Asp Tyr Leu Gln Ser Glu Gly Leu Tyr Val Val Leu Gly
        115                 120                 125

Val Thr Tyr Tyr Gln Lys Ala Leu Glu Ile Leu Lys Ser Lys Ile Thr
130                 135                 140

Asn Pro His Ile Phe Val Phe Ser Asn Asp Met Cys Trp Cys Lys Glu
145                 150                 155                 160

Tyr Leu Met Arg Tyr Val Asp Phe Ser Gly Cys Thr Ile Asp Phe Ile
                165                 170                 175

Glu Gly Asn Thr Glu Gly Asn Ala Val Glu Glu Met Glu Leu Met Arg
            180                 185                 190

Ser Cys Gln His Ala Ile Ile Ala Asn Ser Thr Phe Ser Trp Trp Ala
        195                 200                 205

Ala Tyr Leu Ile Glu Asn Pro Asp Lys Ile Val Ile Met Pro Lys Glu
210                 215                 220

Tyr Leu Asn Asp Ser Ser Arg Phe Leu Pro Lys Gln Phe Leu Ala Leu
225                 230                 235                 240

Lys Asn Trp Phe Leu Val Asp His Ile Trp Gly Ser Val Glu Leu Ala
                245                 250                 255

Asn

<210> SEQ ID NO 7
<211> LENGTH: 286
<212> TYPE: PRT
<213> ORGANISM: Helicobacter mustelae

<400> SEQUENCE: 7

Met Asp Phe Lys Ile Val Gln Val His Gly Gly Leu Gly Asn Gln Met
1               5                   10                  15

Phe Gln Tyr Ala Phe Ala Lys Ser Leu Gln Thr His Leu Asn Ile Pro
            20                  25                  30

Val Leu Leu Asp Thr Thr Trp Phe Asp Tyr Gly Asn Arg Glu Leu Gly
        35                  40                  45

Leu His Leu Phe Pro Ile Asp Leu Gln Cys Ala Ser Ala Gln Gln Ile
    50                  55                  60

Ala Ala Ala His Met Gln Asn Leu Pro Arg Leu Val Arg Gly Ala Leu
65                  70                  75                  80

Arg Arg Met Gly Leu Gly Arg Val Ser Lys Glu Ile Val Phe Glu Tyr
```

```
              85                  90                  95
Met Pro Glu Leu Phe Glu Pro Ser Arg Ile Ala Tyr Phe His Gly Tyr
            100                 105                 110

Phe Gln Asp Pro Arg Tyr Phe Glu Asp Ile Ser Pro Leu Ile Lys Gln
            115                 120                 125

Thr Phe Thr Leu Pro His Pro Thr Glu His Ala Glu Gln Tyr Ser Arg
        130                 135                 140

Lys Leu Ser Gln Ile Leu Ala Ala Lys Asn Ser Val Phe Val His Ile
145                 150                 155                 160

Arg Arg Gly Asp Tyr Met Arg Leu Gly Trp Gln Leu Asp Ile Ser Tyr
                165                 170                 175

Gln Leu Arg Ala Ile Ala Tyr Met Ala Lys Arg Val Gln Asn Leu Glu
            180                 185                 190

Leu Phe Leu Phe Cys Glu Asp Leu Glu Phe Val Gln Asn Leu Asp Leu
        195                 200                 205

Gly Tyr Pro Phe Val Asp Met Thr Thr Arg Asp Gly Ala Ala His Trp
    210                 215                 220

Asp Met Met Leu Met Gln Ser Cys Lys His Gly Ile Ile Thr Asn Ser
225                 230                 235                 240

Thr Tyr Ser Trp Trp Ala Ala Tyr Leu Ile Lys Asn Pro Glu Lys Ile
                245                 250                 255

Ile Ile Gly Pro Ser His Trp Ile Tyr Gly Asn Glu Asn Ile Leu Cys
            260                 265                 270

Lys Asp Trp Val Lys Ile Glu Ser Gln Phe Glu Thr Lys Ser
            275                 280                 285

<210> SEQ ID NO 8
<211> LENGTH: 281
<212> TYPE: PRT
<213> ORGANISM: Bacteroides vulgatus

<400> SEQUENCE: 8

Met Arg Leu Ile Lys Val Thr Gly Gly Leu Gly Asn Gln Met Phe Ile
1               5                   10                  15

Tyr Ala Phe Tyr Leu Arg Met Lys Lys Tyr Tyr Pro Lys Val Arg Ile
                20                  25                  30

Asp Leu Ser Asp Met Met His Tyr Lys Val His Tyr Gly Tyr Glu Met
            35                  40                  45

His Arg Val Phe Asn Leu Pro His Thr Glu Phe Cys Ile Asn Gln Pro
        50                  55                  60

Leu Lys Lys Val Ile Glu Phe Leu Phe Lys Lys Ile Tyr Glu Arg
65                  70                  75                  80

Lys Gln Ala Pro Asn Ser Leu Arg Ala Phe Glu Lys Lys Tyr Phe Trp
                85                  90                  95

Pro Leu Leu Tyr Phe Lys Gly Phe Tyr Gln Ser Glu Arg Phe Phe Ala
            100                 105                 110

Asp Ile Lys Asp Glu Val Arg Glu Ser Phe Thr Phe Asp Lys Asn Lys
        115                 120                 125

Ala Asn Ser Arg Ser Leu Asn Met Leu Glu Ile Leu Asp Lys Asp Glu
130                 135                 140

Asn Ala Val Ser Leu His Ile Arg Arg Gly Asp Tyr Leu Gln Pro Lys
                150                 155                 160

His Trp Ala Thr Thr Gly Ser Val Cys Gln Leu Pro Tyr Tyr Gln Asn
            165                 170                 175
```

```
Ala Ile Ala Glu Met Ser Arg Arg Val Ala Ser Pro Ser Tyr Tyr Ile
            180                 185                 190

Phe Ser Asp Asp Ile Ala Trp Val Lys Glu Asn Leu Pro Leu Gln Asn
            195                 200                 205

Ala Val Tyr Ile Asp Trp Asn Thr Asp Glu Asp Ser Trp Gln Asp Met
            210                 215                 220

Met Leu Met Ser His Cys Lys His His Ile Ile Cys Asn Ser Thr Phe
225                 230                 235                 240

Ser Trp Trp Gly Ala Trp Leu Asn Pro Asn Met Asp Lys Thr Val Ile
            245                 250                 255

Val Pro Ser Arg Trp Phe Gln His Ser Glu Ala Pro Asp Ile Tyr Pro
            260                 265                 270

Thr Gly Trp Ile Lys Val Pro Val Ser
            275                 280

<210> SEQ ID NO 9
<211> LENGTH: 292
<212> TYPE: PRT
<213> ORGANISM: Bacteroides ovatus

<400> SEQUENCE: 9

Met Lys Ile Val Asn Ile Leu Gly Gly Leu Gly Asn Gln Met Phe Val
1               5                   10                  15

Tyr Ala Met Tyr Leu Ala Leu Lys Glu Ala His Pro Glu Glu Glu Ile
            20                  25                  30

Leu Leu Cys Arg Arg Ser Tyr Lys Gly Tyr Pro Leu His Asn Gly Tyr
            35                  40                  45

Glu Leu Glu Arg Ile Phe Gly Val Glu Ala Pro Glu Ala Ala Leu Ser
50                  55                  60

Gln Leu Ala Arg Val Ala Tyr Pro Phe Phe Asn Tyr Lys Ser Trp Gln
65                  70                  75                  80

Leu Met Arg His Phe Leu Pro Leu Arg Lys Ser Met Ala Ser Gly Thr
            85                  90                  95

Thr Gln Ile Pro Phe Asp Tyr Ser Glu Val Thr Arg Asn Asp Asn Val
            100                 105                 110

Tyr Tyr Asp Gly Tyr Trp Gln Asn Glu Lys Asn Phe Leu Ser Ile Arg
            115                 120                 125

Asp Lys Val Ile Lys Ala Phe Thr Phe Pro Glu Phe Arg Asp Glu Lys
            130                 135                 140

Asn Lys Ala Leu Ser Asp Lys Leu Lys Ser Val Lys Thr Ala Ser Cys
145                 150                 155                 160

His Ile Arg Arg Gly Asp Tyr Leu Lys Asp Pro Ile Tyr Gly Val Cys
            165                 170                 175

Asn Ser Asp Tyr Tyr Thr Arg Ala Ile Thr Glu Leu Asn Gln Ser Val
            180                 185                 190

Asn Pro Asp Met Tyr Cys Ile Phe Ser Asp Asp Ile Gly Trp Cys Lys
            195                 200                 205

Glu Asn Phe Lys Phe Leu Ile Gly Asp Lys Glu Val Val Phe Val Asp
            210                 215                 220

Trp Asn Lys Gly Gln Glu Ser Phe Tyr Asp Met Gln Leu Met Ser Leu
225                 230                 235                 240

Cys His Tyr Asn Ile Ile Ala Asn Ser Ser Phe Ser Trp Trp Gly Ala
            245                 250                 255

Trp Leu Asn Asn Asn Asp Asp Lys Val Val Val Ala Pro Glu Arg Trp
            260                 265                 270
```

```
Met Asn Lys Thr Leu Glu Asn Asp Pro Ile Cys Asp Asn Trp Lys Arg
        275                 280                 285

Ile Lys Val Glu
        290

<210> SEQ ID NO 10
<211> LENGTH: 290
<212> TYPE: PRT
<213> ORGANISM: Escherichia coli

<400> SEQUENCE: 10

Met Ser Ile Val Val Ala Arg Leu Ala Gly Gly Leu Gly Asn Gln Met
1               5                   10                  15

Phe Gln Tyr Ala Lys Gly Tyr Ala Glu Ser Val Glu Arg Asn Ser Ser
            20                  25                  30

Leu Lys Leu Asp Leu Arg Gly Tyr Lys Asn Tyr Thr Leu His Gly Gly
        35                  40                  45

Phe Arg Leu Asp Lys Leu Asn Ile Asp Asn Thr Phe Val Met Ser Lys
    50                  55                  60

Lys Glu Met Cys Ile Phe Pro Asn Phe Ile Val Arg Ala Ile Asn Lys
65                  70                  75                  80

Phe Pro Lys Leu Ser Leu Cys Ser Lys Arg Phe Glu Ser Glu Gln Tyr
                85                  90                  95

Ser Lys Lys Ile Asn Gly Ser Met Lys Gly Ser Val Glu Phe Ile Gly
            100                 105                 110

Phe Trp Gln Asn Glu Arg Tyr Phe Leu Glu His Lys Glu Lys Leu Arg
        115                 120                 125

Glu Ile Phe Thr Pro Ile Asn Ile Asn Leu Asp Ala Lys Glu Leu Ser
    130                 135                 140

Asp Val Ile Arg Cys Thr Asn Ser Val Ser Val His Ile Arg Arg Gly
145                 150                 155                 160

Asp Tyr Val Ser Asn Val Glu Ala Leu Lys Ile His Gly Leu Cys Thr
                165                 170                 175

Glu Arg Tyr Tyr Ile Asp Ser Ile Arg Tyr Leu Lys Glu Arg Phe Asn
            180                 185                 190

Asn Leu Val Phe Phe Val Phe Ser Asp Asp Ile Glu Trp Cys Lys Lys
        195                 200                 205

Tyr Lys Asn Glu Ile Phe Ser Arg Ser Asp Val Lys Phe Ile Glu
    210                 215                 220

Gly Asn Thr Gln Glu Val Asp Met Trp Leu Met Ser Asn Ala Lys Tyr
225                 230                 235                 240

His Ile Ile Ala Asn Ser Ser Phe Ser Trp Trp Gly Ala Trp Leu Lys
                245                 250                 255

Asn Tyr Asp Leu Gly Ile Thr Ile Ala Pro Thr Pro Trp Phe Glu Arg
            260                 265                 270

Glu Glu Leu Asn Ser Phe Asp Pro Cys Pro Glu Lys Trp Val Arg Ile
        275                 280                 285

Glu Lys
    290

<210> SEQ ID NO 11
<211> LENGTH: 289
<212> TYPE: PRT
<213> ORGANISM: Bacteroides fragilis

<400> SEQUENCE: 11
```

Met Phe Phe Arg Cys Cys Met Lys Ile Val Gln Ile Ile Gly Gly Leu
1               5                   10                  15

Gly Asn Gln Met Phe Gln Phe Ala Phe Tyr Leu Ala Leu Lys Glu Lys
            20                  25                  30

Tyr Val Asn Val Lys Leu Asp Thr Ser Ser Phe Gly Ala Tyr Thr His
        35                  40                  45

Asn Gly Phe Glu Leu Asp Lys Val Phe His Val Glu Tyr Leu Lys Ala
    50                  55                  60

Ser Ile Arg Glu Arg Ile Lys Leu Ser Tyr Gln Gly Ser Glu Ile Trp
65                  70                  75                  80

Ile Arg Val Leu Arg Lys Leu Leu Lys Arg Lys Lys Thr Glu Tyr Val
                85                  90                  95

Glu Pro Tyr Leu Cys Phe Asp Glu Asn Ala Ile Ser Leu Ser Cys Asp
            100                 105                 110

Lys Tyr Tyr Ile Gly Tyr Trp Gln Ser Tyr Lys Tyr Phe Thr Asn Ile
        115                 120                 125

Glu Ala Ala Ile Arg Gly Gln Phe His Phe Ser Lys Val Leu Ser Asp
    130                 135                 140

Lys Asn Glu Phe Ile Lys Lys Gln Met Gln Asn Ser Asn Ser Val Ser
145                 150                 155                 160

Leu His Val Arg Leu Gly Asp Tyr Val Asn Asn Pro Ala Tyr Ser Asn
                165                 170                 175

Ile Cys Thr Ser Ala Tyr Tyr Asn Lys Ala Ile Asn Ile Ile Gln Ser
            180                 185                 190

Lys Val Ser Glu Pro Lys Phe Phe Val Phe Ser Asp Asp Thr Val Trp
        195                 200                 205

Cys Lys Asp His Leu Lys Ile Pro Asn Cys His Ile Ile Asp Trp Asn
    210                 215                 220

Asn Lys Glu Glu Ser Tyr Trp Asp Met Cys Leu Met Thr Tyr Cys Lys
225                 230                 235                 240

His Asn Ile Ile Ala Asn Ser Ser Phe Ser Trp Trp Gly Ala Trp Leu
                245                 250                 255

Asn Thr Asn Pro Glu Arg Ile Val Ile Ala Pro Gly Lys Trp Ile Asn
            260                 265                 270

Asp Asp Arg Val Gln Val Ser Asp Ile Pro Ser Asp Trp Ile Cys
        275                 280                 285

Val

<210> SEQ ID NO 12
<211> LENGTH: 287
<212> TYPE: PRT
<213> ORGANISM: Bacteroides fragilis

<400> SEQUENCE: 12

Met Leu Tyr Val Ile Leu Arg Gly Arg Leu Gly Asn Asn Leu Phe Gln
1               5                   10                  15

Ile Ala Thr Ala Ala Ser Leu Thr Gln Asn Phe Ile Phe Cys Thr Val
            20                  25                  30

Asn Lys Asp Gln Glu Arg Gln Val Leu Leu Tyr Lys Asp Ser Phe Phe
        35                  40                  45

Lys Asn Ile Lys Val Met Lys Gly Val Pro Asp Gly Ile Pro Tyr Tyr
    50                  55                  60

Lys Glu Pro Phe His Glu Phe Ser Arg Ile Pro Tyr Glu Glu Gly Lys
65                  70                  75                  80

```
Asp Leu Ile Ile Asp Gly Tyr Phe Gln Ser Glu Lys Tyr Phe Lys Arg
                85                  90                  95
Ser Val Val Leu Asp Leu Tyr Arg Ile Thr Asp Glu Leu Arg Lys Lys
            100                 105                 110
Ile Trp Asn Ile Cys Gly Asn Ile Leu Glu Lys Gly Glu Thr Val Ser
        115                 120                 125
Ile His Val Arg Arg Gly Asp Tyr Leu Lys Leu Pro His Ala Leu Pro
    130                 135                 140
Phe Cys Gly Lys Ser Tyr Tyr Lys Asn Ala Ile Gln Tyr Ile Gly Glu
145                 150                 155                 160
Asp Lys Ile Phe Ile Ile Cys Ser Asp Asp Ile Asp Trp Cys Lys Lys
                165                 170                 175
Asn Phe Ile Gly Lys Arg Tyr Tyr Phe Ile Glu Asn Thr Thr Pro Leu
            180                 185                 190
Leu Asp Leu Tyr Ile Gln Ser Leu Cys Thr His Asn Ile Ile Ser Asn
        195                 200                 205
Ser Ser Phe Ser Trp Trp Gly Ala Trp Leu Asn Glu Asn Ser Asn Lys
    210                 215                 220
Ile Val Ile Ala Pro Gln Met Trp Phe Gly Ile Ser Val Lys Leu Gly
225                 230                 235                 240
Val Ser Asp Leu Leu Pro Val Ser Trp Val Arg Leu Pro Asn Asn Tyr
                245                 250                 255
Thr Leu Gly Arg Tyr Cys Phe Ala Leu Tyr Lys Val Val Glu Asp Tyr
            260                 265                 270
Leu Leu Asn Ile Leu Arg Leu Ile Trp Lys Arg Lys Lys Asn Met
        275                 280                 285

<210> SEQ ID NO 13
<211> LENGTH: 1583
<212> TYPE: DNA
<213> ORGANISM: Artificial Sequence
<220> FEATURE:
<223> OTHER INFORMATION: Genomic DNA sequence of the PlacIq lacY+
      chromosomal construct derived from Escherichia coli

<400> SEQUENCE: 13
caccatcgaa tggcgcaaaa ccttctgcgg tatggcatga tagcgcccgg aagagagtca    60
agtgtaggct ggagctgctt cgaagttcct atactttcta gagaatagga acttcggaat   120
aggaacttcg gaataggaac taaggaggat attcatatgt actatttaaa aaacacaaac   180
ttttggatgt tcggtttatt cttttttctt tactttttta tcatgggagc ctacttcccg   240
tttttcccga tttggctaca tgacatcaac catatcagca aaagtgatac gggtattatt   300
tttgccgcta tttctctgtt ctcgctatta ttccaaccgc tgtttggtct gctttctgac   360
aaactcgggc tgcgcaaata cctgctgtgg attattaccg gcatgttagt gatgtttgcg   420
ccgttcttta tttttatctt cgggccactg ttacaataca acattttagt aggatcgatt   480
gttggtggta tttatctagg cttttgtttt aacgccggtg cgccagcagt agaggcattt   540
attgagaaag tcagccgtcg cagtaatttc gaatttggtc gcgcgcggat gtttggctgt   600
gttggctggg cgctgtgtgc ctcgattgtc ggcatcatgt tcaccatcaa taatcagttt   660
gttttctggc tgggctctgg ctgtgcactc atcctcgccg ttttactctt tttcgccaaa   720
acggatgcgc cctcttctgc cacggttgcc aatgcggtag gtgccaacca ttcggcattt   780
agccttaagc tggcactgga actgttcaga cagccaaaac tgtggttttt gtcactgtat   840
```

| | |
|---|---|
| gttattggcg tttcctgcac ctacgatgtt tttgaccaac agtttgctaa tttctttact | 900 |
| tcgttctttg ctaccggtga acagggtacg cgggtatttg gctacgtaac gacaatgggc | 960 |
| gaattactta acgcctcgat tatgttcttt gcgccactga tcattaatcg catcggtggg | 1020 |
| aaaaacgccc tgctgctggc tggcactatt atgtctgtac gtattattgg ctcatcgttc | 1080 |
| gccacctcag cgctggaagt ggttattctg aaaacgctgc atatgtttga agtaccgttc | 1140 |
| ctgctggtgg gctgctttaa atatattacc agccagtttg aagtgcgttt ttcagcgacg | 1200 |
| atttatctgg tctgtttctg cttctttaag caactggcga tgattttat gtctgtactg | 1260 |
| gcgggcaata tgtatgaaag catcggtttc cagggcgctt atctggtgct gggtctggtg | 1320 |
| gcgctgggct tcaccttaat ttccgtgttc acgcttagcg gccccggccc gctttccctg | 1380 |
| ctgcgtcgtc aggtgaatga agtcgcttaa gcaatcaatg tcggatgcgg cgcgagcgcc | 1440 |
| ttatccgacc aacatatcat aacggagtga tcgcattgta aattataaaa attgcctgat | 1500 |
| acgctgcgct tatcaggcct acaagttcag cgatctacat tagccgcatc cggcatgaac | 1560 |
| aaagcgcagg aacaagcgtc gca | 1583 |

<210> SEQ ID NO 14
<211> LENGTH: 2070
<212> TYPE: DNA
<213> ORGANISM: Artificial Sequence
<220> FEATURE:
<223> OTHER INFORMATION: Sequence of the chromosomal region derived from Escherichia coli bearing the (delta)wcaJ::FRT mutation

<400> SEQUENCE: 14

| | |
|---|---|
| gttcggttat atcaatgtca aaacctcac gccgctcaag ctggtgatca actccgggaa | 60 |
| cggcgcagcg ggtccggtgg tggacgccat tgaagcccgc tttaaagccc tcggcgcgcc | 120 |
| cgtggaatta atcaaagtgc acaacacgcc ggacggcaat ttccccaacg gtattcctaa | 180 |
| cccactactg ccggaatgcc gcgacgacac ccgcaatgcg gtcatcaaac acggcgcgga | 240 |
| tatgggcatt gcttttgatg gcgattttga ccgctgtttc ctgtttgacg aaaaagggca | 300 |
| gtttattgag ggctactaca ttgtcggcct gttggcagaa gcattcctcg aaaaaaatcc | 360 |
| cggcgcgaag atcatccacg atccacgtct ctcctggaac accgttgatg tggtgactgc | 420 |
| cgcaggtggc acgccggtaa tgtcgaaaac cggacacgcc tttattaaag aacgtatgcg | 480 |
| caaggaagac gccatctatg gtggcgaaat gagcgcccac cattacttcc gtgatttcgc | 540 |
| ttactgcgac agcggcatga tcccgtggct gctggtcgcc gaactggtgt gcctgaaaga | 600 |
| taaaacgctg ggcgaactgg tacgcgaccg gatggcggcg tttccggcaa gcggtgagat | 660 |
| caacagcaaa ctggcgcaac ccgttgaggc gattaaccgc gtggaacagc attttagccg | 720 |
| tgaggcgctg gcggtggatc gcaccgatgg catcagcatg accttttgccg actggcgctt | 780 |
| taacctgcgc acctccaata ccgaaccggt ggtgcgcctg aatgtggaat cgcgcggtga | 840 |
| tgtgccgctg atggaagcgc gaacgcgaac tctgctgacg ttgctgaacg agtaatgtcg | 900 |
| gatcttccct taccccactg cgggtaaggg gctaataaca ggaacaacga tgattccggg | 960 |
| gatccgtcga cctgcagttc gaagttccta ttctctagaa agtataggaa cttcgaagca | 1020 |
| gctccagcct acagttaaca aagcggcata ttgatatgag cttacgtgaa aaaccatca | 1080 |
| gcggcgcgaa gtggtcggcg attgccacgg tgatcatcat cggcctcggg ctggtgcaga | 1140 |
| tgaccgtgct ggcgcggatt atcgacaacc accagttcgg cctgcttacc gtgtcgctgg | 1200 |
| tgattatcgc gctggcagat acgctttctg acttcggtat cgctaactcg attattcagc | 1260 |

```
gaaaagaaat cagtcacctt gaactcacca cgttgtactg gctgaacgtc gggctgggga    1320
tcgtggtgtg cgtggcggtg tttttgttga gtgatctcat cggcgacgtg ctgaataacc    1380
cggacctggc accgttgatt aaaacattat cgctggcgtt tgtggtaatc ccccacgggc    1440
aacagttccg cgcgttgatg caaaaagagc tggagttcaa caaaatcggc atgatcgaaa    1500
ccagcgcggt gctggcgggc ttcacttgta cggtggttag cgcccatttc tggccgctgg    1560
cgatgaccgc gatcctcggt tatctggtca atagtgcggt gagaacgctg ctgtttggct    1620
actttggccg caaaatttat cgccccggtc tgcatttctc gctggcgtcg gtggcaccga    1680
acttacgctt tggtgcctgg ctgacggcgg acagcatcat caactatctc aataccaacc    1740
tttcaacgct cgtgctggcg cgtattctcg gcgcgggcgt ggcaggggga tacaacctgg    1800
cgtacaacgt ggccgttgtg ccaccgatga agctgaaccc aatcatcacc cgcgtgttgt    1860
ttccggcatt cgccaaaatt caggacgata ccgaaaagct gcgtgttaac ttctacaagc    1920
tgctgtcggt agtggggatt atcaactttc cggcgctgct cgggctaatg gtggtgtcga    1980
ataactttgt accgctggtc tttggtgaga agtggaacag cattattccg gtgctgcaat    2040
tgctgtgtgt ggtgggtctg ctgcgctccg                                     2070
```

<210> SEQ ID NO 15
<211> LENGTH: 5046
<212> TYPE: DNA
<213> ORGANISM: Artificial Sequence
<220> FEATURE:
<223> OTHER INFORMATION: Genomic DNA sequence surrounding the lacZ+
      insertion into the lon region derived from Escherichia coli

<400> SEQUENCE: 15

```
gtggatggaa gaggtggaaa aagtggttat ggaggagtgg gtaattgatg gtgaaaggaa      60
agggttggtg atttatggga aggggaagg ggaagaggga tgtggtgaat aattaaggat     120
tgggatagaa ttagttaagg aaaaaggggg gattttatgt gggtttaat ttttggtgta     180 ttgtggggt tgaatgtggg ggaaagatgg ggatatagtg aggtagatgt taatagatgg     240
ggtgaaggag agtggtgtga tgtgattagg tgggggaaat taaagtaaga gagaggtgta     300
tgattggggg gatgggtgga ggtggagttg gaagttggta ttgtgtagaa agtataggaa     360
gttgagaggg gttttgaagg tgagggtggg ggaaggagtg aggggggaag gggtggtaaa     420 ggaagggaa gaggtagaaa gggagtgggg agaaaggggt gtgaggggg atgaatgtga     480 ggtagtgggg tatgtggaga agggaaaagg gaagggaaa gagaaaggag gtaggttgga     540 gtgggttag atgggatag gtagagtggg gggttttatg gagaggaagg gaagggaat     600 tgggaggtgg ggggggtgt ggtaaggttg ggaaggggtg gaaagtaaag tggatgggtt    660
tgttgggggg aaggatgtga tggggaggg gatgaagatg tgatgaagag agaggatgag    720
gatggtttgg gatgattgaa gaagatggat tggaggaggg ttgtgggggg ggttgggtgg    780
agagggtatt ggggtatgag tgggagaag agagaatggg gtggtgtgat ggggggtgt    840 tggggtgtg agggagggg ggggggttg ttttgtgaa gagggaggtg tgggtgggg     900 tgaatgaagt ggaggaggag ggagggggg tatggtgggt gggaggagg ggggttggtt      960 ggggaggtgt ggtggaggtt gtgagtgaag gggaaggga gtgggtggta ttggggggaag   1020 tgggggggga ggatgtggtg tgatgtgagg ttggtggtgg ggagaaagta tggatgatgg    1080
gtgatggaat ggggggggtg gatagggttg atgggggtag gtggggattg gaggaggaag    1140
ggaaagatgg gatggaggga ggaggtagtg ggatggaagg gggtgttgtg gatgaggatg    1200
```

-continued

```
atgtggagga agaggatgag ggggtggggg gaggggaagt gttggggagg gtgaaggggg    1260
gatgggggag ggggaggatg tggtggtgag ggatgggggat gggtggttgg ggaatatgat    1320
ggtggaaaat ggggggtttt gtggattgat ggagtgtggg ggggtggggtg tgggggaggg   1380
gtatgaggag atagggttgg gtaggggtga tattggtgaa gaggttgggg gggaatgggg    1440
tgaggggttg gtggtggttt agggtatggg gggtggggat tgggagggga tggggttgta    1500
tggggttgtt gaggagttgt tgtaataagg ggatgttgaa gttggtattg ggaagttggt    1560
attgtgtaga aagtatagga agttggaagg aggtggaggg tagataaagg gggggggttat  1620
ttttgagagg agaggaagtg gtaatggtag ggaggggggg tgaggtggaa ttgggggggat  1680
agtgaggggg tggaggagtg gtgggaggga atgggggatat ggaaagggtg gatattgagg  1740
gatgtgggtt gttggggggtg gaggagatgg ggatgggtgg tttggatgag ttggtgttga  1800
gtgtaggggg tgatgttgaa gtggaagtgg ggggggggagt ggtgtggggg ataattgaat  1860
tgggggggtgg gggagggggag agggttttgg gtggggaaga ggtaggggggt atagatgttg  1920
agaatgggag atgggagggg tgaaaagagg gggagtaagg ggggtgggga tagttttgtt    1980
gggggggtaa tgggagggag tttagggggt gtggtaggtg ggggaggtgg gagttgaggg   2040
gaatgggggg gggatgggt gtatggtgg ggagttgaag atgaagggta atggggattt     2100
gaggagtagg atgaatgggg taggttttgg gggtgataaa taaggttttg gggtgatggt  2160
gggagggggtg aggggtggta atgaggaggg gatgaggaag tgtatgtggg gtggagtgga  2220
agaagggtgg ttgggggtgg taatgggggg ggggttgga gggttggagg gaggggttag    2280
ggtgaatggg ggtgggttga gttagggggaa tgtggttatg gagggggtgga ggggtgaagt  2340
gatgggggag gggggtgagg agttgttttt tatggggaat ggagatgtgt gaaagaaagg  2400
gtgagtgggg gttaaattgg gaagggttat taggggaggtg gatggaaaaa tggatttggg  2460
tggtggtgag atgggggatg gggtgggagg ggggggggag ggtgagagtg aggttttggg  2520
ggagagggga gtggtgggag ggggtgatgt ggggggggttg tgaggatggg gtggggttgg  2580
gttggagtag gggtagtgtg agggagagtt ggggggggggt gtggggtgg ggtagttgag   2640
ggagttgaat gaagtgttta ggttgtggag ggagatggag agggagttga ggggttggga   2700
ggggggttagg atggagggggg aggatggagt ggaggaggtg gttatgggta tgagggaaga  2760
ggtattgggt ggtgagttgg atggtttggg gggataaagg gaagtggaaa aagtggtggt  2820
ggtgttttgg ttgggtgagg ggtggatggg gggtgggggtg gggaaagagg agagggttga  2880
tagagaagtg gggatggttg ggggtatggg gaaaatgagg gggggtaaggg gaggaggggt  2940
tggggttttg atgatatttta atgagggagt gatggaggga gtgggagagg aaggggggggt  3000
gtaaaggggg atagtgagga aagggtgggg agtatttagg gaaaggggga agagtgttag   3060
ggatggggtg ggggtattgg gaaaggatga gggggggggt gtgtggaggt agggaaaggg   3120
atttttttgat ggaggatttg gggagagggg gaagggggtg gtgttgatgg agggggggggt  3180
agatggggga aataatatgg gtgggggtgg tgtggggtgg ggggggttga tagtggaggg    3240
gggggggaagg atggagagat ttgatggagg gatagagggg gtggtgatta gggggggtggg 3300
gtgattgatt ggggagggag gagatgatga gagtgggggtg attaggatgg gggtggagga  3360
ttgggggttag ggggttgggtg atgggggggta gggaggggggg atgatgggtg agaggattga  3420
ttgggaggat gggggtgggtt tgaatattgg gttgatggag gagatagagg gggtagggggt 3480
gggagagggt gtaggagagg ggatggttgg gataatggga agagggggagg gggttaaagt  3540
tgttgtggtt gatgaggagg atatggtgga ggatggtgtg gtgatggatg aggtgaggat    3600
```

```
ggagaggatg atggtggtga gggttaaggg gtggaatgag gaaggggttg gggttgagga    3660
ggaggagagg attttgaatg gggaggtggg ggaaagggag atgggagggt tgtggttgaa    3720
tgagggtggg gtgggggtg tggagttgaa ggagggagg atagagattg gggatttggg     3780
gggtggagag tttggggttt tggaggttga gaggtagtgt gaggggatgg ggataaggag    3840
gagggtgatg gataatttga gggggaaag ggggggtggg ggtggggagg tgggtttgag    3900
ggtgggataa agaaagtgtt aggggtaggt agtgagggaa gtggggggag atgtgaagtt    3960
gagggtggag tagaggggg gtgaaatgat gattaaaggg agtgggaaga tggaaatggg    4020
tgatttgtgt agtgggttta tggaggaagg agaggtgagg gaaaatgggg gtgatggggg    4080
agatatggtg atgttggaga taagtggggt gagtggaggg gaggaggatg agggggaggg    4140
ggttttgtgg gggggtaaa aatgggtga ggtgaaattg agaggggaaa ggagtgtggt    4200
gggggtaagg gagggagggg gggttggagg agagatgaaa gggggagtta agggatgaa    4260 aaataattgg ggtgtgggt tggtgtaggg aggtttgatg aagattaaat gtgagggagt    4320 aagaagggt gggattgtgg gtgggaagaa agggggatt gagggtaatg ggataggtga    4380
ggttggtgta gatggggga tggtaagggt ggatgtggga gtttgagggg aggaggagag    4440 tatggggtg aggaagatgg gagggaggga ggtttggggg aggggttgtg gtgggggaaa    4500
ggagggaaag ggggattggg gattgagggt ggggaagtgt tggaagggg gatggtgggg    4560 ggggtgttgg gtattagggg aggtggggaa aggggggatgt ggtggaaggg gattaagttg    4620
ggtaagggga gggttttggg agtgaggagg ttgtaaaagg agggggagtg aatgggtaat    4680
gatggtgata gtaggtttgg tgaggttgtg agtggaaaat agtgaggtgg gggaaaatgg    4740
agtaataaaa agaggggtgg gagggtaatt ggggggttggg agggttttt tgtgtgggta    4800 agttagatgg gggatggggg ttgggggttat taagggggtgt tgtaagggga tgggtggggt    4860
gatataagtg gtggggtggtt gtaggttgaa ggattgaagt gggatataaa ttataaagag    4920
gaagagaaga gtgaataaat gtgaattgat ggagaagatt ggtggagggg gtgatatgtg    4980
taaaggtggg ggtgggggtg ggttagatgg tattattggt tgggtaagtg aatgtgtgaa    5040
agaagg                                                              5046

<210> SEQ ID NO 16
<211> LENGTH: 6199
<212> TYPE: DNA
<213> ORGANISM: Artificial Sequence
<220> FEATURE:
<223> OTHER INFORMATION: plasmid pG204

<400> SEQUENCE: 16
aattctaaaa attgattgaa tgtatgcaaa taaatgcata caccataggt gtggtttaat     60
ttgatgccct ttttcagggc tggaatgtgt aagagcgggg ttatttatgc tgttgttttt    120
ttgttactcg ggaagggctt tacctcttcc gcataaacgc ttccatcagc gtttatagtt    180
aaaaaaatct ttcggaactg gttttgcgct taccccaacc aacagggat ttgctgcttt    240 ccattgagcc tgtttctctg cgcgacgttc gcggcggcgt gtttgtgcat ccatctggat    300
tctcctgtca gttagctttg gtggtgtgtg gcagttgtag tcctgaacga aaaccccccg    360
cgattggcac attggcagct aatccggaat cgcacttacg gccaatgctt cgtttcgtat    420
cacacacccc aaagccttct gctttgaatg ctgcccttct tcaggggctta attttttaaga    480 gcgtcacctt catggtggtc agtgcgtcct gctgatgtgc tcagtatcac cgccagtggt    540
```

```
atttatgtca acaccgccag agataattta tcaccgcaga tggttatctg tatgtttttt    600
atatgaattt attttttgca gggggcatt gtttggtagg tgagagatca attctgcatt    660
aatgaatcgg ccaacgcgcg gggagaggcg gtttgcgtat gggcgctct tccgcttcct    720
cgctcactga ctcgctgcgc tcggtcgttc ggctgcggcg agcggtatca gctcactcaa    780
aggcggtaat acggttatcc acagaatcag gggataacgc aggaaagaac atgtgagcaa    840
aaggccagca aaaggccagg aaccgtaaaa aggccgcgtt gctggcgttt ttccataggc    900
tccgcccccc tgacgagcat cacaaaaatc gacgctcaag tcagaggtgg cgaaacccga    960
caggactata aagataccag gcgtttcccc ctggaagctc cctcgtgcgc tctcctgttc   1020
cgaccctgcc gcttaccgga tacctgtccg cctttctccc ttcgggaagc gtggcgcttt   1080
ctcatagctc acgctgtagg tatctcagtt cggtgtaggt cgttcgctcc aagctgggct   1140
gtgtgcacga accccccgtt cagcccgacc gctgcgcctt atccggtaac tatcgtcttg   1200
agtccaaccc ggtaagacac gacttatcgc cactggcagc agccactggt aacaggatta   1260
gcagagcgag gtatgtaggc ggtgctacag agttcttgaa gtggtggcct aactacggct   1320
acactagaag gacagtattt ggtatctgcg ctctgctgaa gccagttacc ttcggaaaaa   1380
gagttggtag ctcttgatcc ggcaaacaaa ccaccgctgg tagcggtggt ttttttgttt   1440
gcaagcagca gattacgcgc agaaaaaaag gatctcaaga agatcctttg atcttttcta   1500
cggggtctga cgctcagtgg aacgaaaact cacgttaagg gattttggtc atgagattat   1560
caaaaaggat cttcacctag atccttttaa attaaaaatg aagttttaaa tcaatctaaa   1620
gtatatatga gtaaacttgg tctgacagtt accaatgctt aatcagtgag gcacctatct   1680
cagcgatctg tctatttcgt tcatccatag ttgcctgact ccccgtcgtg tagataacta   1740
cgatacggga gggcttacca tctggcccca gtgctgcaat gataccgcga gacccacgct   1800
caccggctcc agatttatca gcaataaacc agccagccgg aagggccgag cgcagaagtg   1860
gtcctgcaac tttatccgcc tccatccagt ctattaattg ttgccgggaa gctagagtaa   1920
gtagttcgcc agttaatagt ttgcgcaacg ttgttgccat tgctacaggc atcgtggtgt   1980
cacgctcgtc gtttggtatg gcttcattca gctccggttc ccaacgatca aggcgagtta   2040
catgatcccc catgttgtgc aaaaaagcgg ttagctcctt cggtcctccg atcgttgtca   2100
gaagtaagtt ggccgcagtg ttatcactca tggttatggc agcactgcat aattctctta   2160
ctgtcatgcc atccgtaaga tgcttttctg tgactggtga gtactcaacc aagtcattct   2220
gagaatagtg tatgcggcga ccgagttgct cttgcccggc gtcaatacgg gataataccg   2280
cgccacatag cagaacttta aaagtgctca tcattggaaa acgttcttcg ggcgaaaac    2340
tctcaaggat cttaccgctg ttgagatcca gttcgatgta acccactcgt gcacccaact   2400
gatcttcagc atcttttact ttcaccagcg tttctgggtg agcaaaaaca ggaaggcaaa   2460
atgccgcaaa aaagggaata agggcgacac ggaaatgttg aatactcata ctcttccttt   2520
ttcaatatta ttgaagcatt tatcagggtt attgtctcat gagcggatac atatttgaat   2580
gtatttagaa aaataaacaa ataggggttc cgcgcacatt tccccgaaaa gtgccacctg   2640
acgtctaaga aaccattatt atcatgacat taacctataa aaataggcgt atcacgaggc   2700
cctttcgtct cgcgcgtttc ggtgatgacg gtgaaaacct ctgacacatg cagctcccgg   2760
agacggtcac agcttgtctg taagcggatg ccgggagcag acaagcccgt cagggcgcgt   2820
cagcgggtgt tggcgggtgt cggggctggc ttaactatgc ggcatcagag cagattgtac   2880
tgagagtgca ccatatatgc ggtgtgaaat accgcacaga tgcgtaagga gaaaataccg   2940
```

```
catcaggcgc ctcctcaacc tgtatattcg taaaccacgc ccaatgggag ctgtctcagg    3000
tttgttcctg attggttacg gcgcgtttcg catcattgtt gagttttcc gccagcccga     3060 cgcgcagttt accggtgcct gggtgcagta catcagcatg gggcaaattc tttccatccc    3120
gatgattgtc gcgggtgtga tcatgatggt ctgggcatat cgtcgcagcc cacagcaaca    3180
cgtttcctga ggaaccatga aacagtattt agaactgatg caaaaagtgc tcgacgaagg    3240
cacacagaaa aacgaccgta ccggaaccgg aacgctttcc attttggtc atcagatgcg     3300 ttttaacctg caagatggat tcccgctggt gacaactaaa cgttgccacc tgcgttccat    3360
catccatgaa ctgctgtggt ttctgcaggg cgacactaac attgcttatc tacacgaaaa    3420
caatgtcacc atctgggacg aatgggccga tgaaacggc gacctcgggc cagtgtatgg     3480
taaacagtgg cgcgcctggc caacgccaga tggtcgtcat attgaccaga tcactacggt    3540
actgaaccag ctgaaaaacg acccggattc gcgccgcatt attgtttcag cgtggaacgt    3600
aggcgaactg gataaaatgg cgctggcacc gtgccatgca ttcttccagt tctatgtggc    3660
agacggcaaa ctctcttgcc agctttatca gcgctcctgt gacgtcttcc tcggcctgcc    3720
gttcaacatt gccagctacg cgttattggt gcatatgatg cgcagcagt gcgatctgga     3780 agtgggtgat tttgtctgga ccggtggcga cacgcatctg tacagcaacc atatggatca    3840
aactcatctg caattaagcc gcgaaccgcg tccgctgccg aagttgatta tcaaacgtaa    3900
acccgaatcc atcttcgact accgtttcga agactttgag attgaaggct acgatccgca    3960
tccgggcatt aaagcgccgg tggctatcta attacgaaac atcctgccag agccgacgcc    4020
agtgtgcgtc ggttttttta ccctccgtta aattcttcga acgccttcc cgaaggcgcc     4080 attcgccatt caggctgcgc aactgttggg aagggcgatc ggtgcgggcc tcttcgctat    4140
tacgccagct ggcgaaaggg ggatgtgctg caaggcgatt aagttgggta acgccagggt    4200
tttcccagtc acgacgttgt aaaacgacgg ccagtgccaa gctttcttta atgaagcagg    4260
gcatcaggac ggtatctttg tggagaaagc agagtaatct tattcagcct gactggtggg    4320
aaaccaccag tcagaatgtg ttagcgcatg ttgacaaaaa taccattagt cacattatcc    4380
gtcagtcgga cgacatggta gataacctgt ttattatgcg ttttgatctt acgtttaata    4440
ttacctttat gcgatgaaac ggtcttggct ttgatattca tttggtcaga gatttgaatg    4500
gttccctgac ctgccatcca cattcgcaac atactcgatt cggttcggct caatgataac    4560
gtcggcatat ttaaaaacga ggttatcgtt gtctcttttt tcagaatatc gccaaggata    4620
tcgtcgagag attccggttt aatcgattta gaactgatca ataaattttt tctgaccaat    4680
agatattcat caaaatgaac attggcaatt gccataaaaa cgataaataa cgtattggga    4740
tgttgattaa tgatgagctt gatacgctga ctgttagaag catcgtggat gaaacagtcc    4800
tcattaataa acaccactga agggcgctgt gaatcacaag ctatggcaag gtcatcaacg    4860
gtttcaatgt cgttgatttc tctttttta accctctac tcaacagata cccgttaaa      4920 cctagtcggg tgtaactaca taaatccata ataatcgttg acatggcata ccctcactca    4980
atgcgtaacg ataattcccc ttacctgaat atttcatcat gactaaacgg aacaacatgg    5040
gtcacctaat gcgccactct cgcgattttt caggcggact tactatcccg taaagtgttg    5100
tataatttgc ctggaattgt cttaaagtaa agtaaatgtt gcgatatgtg agtgagctta    5160
aaacaaatat ttcgctgcag gagtatcctg gaagatgttc gtgagaagct tactgctcac    5220
aagaaaaaag gcacgtcatc tgacgtgcct tttttatttg tactaccctg tacgattact    5280
```

```
gcagctcgag ctaacacgag ctatgtttat ccacgtttat ccagtgattg actatgggga    5340
tataagtatt ttttggagtt atatcgtacc aaggagtagg ataaataaca atctgtgacg    5400
ctgatgtacc taaataagcc ccccaccaac taaaactact attcgctata atatgatggt    5460
tagctaagct cattaaccat aaatcttctt cttgtgataa atcttctgaa taatatatat    5520
tatatttttt actgagtaat gtttcgatat tttctttaca ccaaaaaata tcatcactga    5580
aaataaacac gtcacgtatc attgccaaat cgcgtatttt atttaaagct ttttttgtaat    5640
actctaacga acaaacgcca tgagttaaag tagctgtttt gttttttata taatctcctc    5700
ttcttatatg aatagaaagt gatgattgag attcaagaat ttttgctgca agtaaatttg    5760
cttgttcaga cacattcttt ggaataaaaa attcttttag atctaatata tgtttatgga    5820
aaaagtgctc agattgccaa taccctatat attttttgga tttccatttt tgcgctatat    5880
attcaaaatc ataaccatag gcatgaaatt cattgcaaaa acctaaaaaa agaaagattt    5940
caggatataa tcttgaccca cgaaccaaaa atttataaat attattaatt tttggtgtgt    6000
aatactgtaa atattcctct ggaatttgta gattgtttag cctgtaacca ccatgatcat    6060
catttttcagc ataatgactt atatcaaaat ataatggtgt cccattaatt ttggaaagcg    6120
catacccaaa tgagaactga aaaagttgat ttccaagtcc gccttgtaat cttataatag    6180
acattatatc tccttcttg                                                 6199

<210> SEQ ID NO 17
<211> LENGTH: 6170
<212> TYPE: DNA
<213> ORGANISM: Artificial Sequence
<220> FEATURE:
<223> OTHER INFORMATION: plasmid pG216

<400> SEQUENCE: 17
tctagaattc taaaaattga ttgaatgtat gcaaataaat gcatacacca taggtgtggt     60
ttaatttgat gccctttttc agggctggaa tgtgtaagag cggggttatt tatgctgttg    120
ttttttttgtt actcgggaag ggctttacct cttccgcata aacgcttcca tcagcgttta    180
tagttaaaaa aatctttcgg aactggtttt gcgcttaccc caaccaacag gggatttgct    240
gctttccatt gagcctgttt ctctgcgcga cgttcgcggc ggcgtgtttg tgcatccatc    300
tggattctcc tgtcagttag cttttggtggt gtgtggcagt tgtagtcctg aacgaaaacc    360
ccccgcgatt ggcacattgg cagctaatcc ggaatcgcac ttacggccaa tgcttcgttt    420
cgtatcacac accccaaagc cttctgcttt gaatgctgcc cttcttcagg gcttaatttt    480
taagagcgtc accttcatgg tggtcagtgc gtcctgctga tgtgctcagt atcaccgcca    540
gtggtattta tgtcaacacc gccagagata atttatcacc gcagatggtt atctgtatgt    600
ttttttatatg aatttatttt ttgcaggggg gcattgtttg gtaggtgaga gatcaattct    660
gcattaatga atcggccaac gcgcggggag aggcggtttg cgtattgggc gctcttccgc    720
ttcctcgctc actgactcgc tgcgctcggt cgttcggctg cggcgagcgg tatcagctca    780
ctcaaaggcg gtaatacggt tatccacaga atcagggggat aacgcaggaa agaacatgtg    840
agcaaaaggc cagcaaaagg ccaggaaccg taaaaaggcc gcgttgctgg cgttttttcca    900
taggctccgc cccctgacg agcatcacaa aaatcgacgc tcaagtcaga ggtggcgaaa    960
cccgacagga ctataaagat accaggcgtt tcccctgga agctccctcg tgcgctctcc   1020
tgttccgacc ctgccgctta ccggatacct gtccgccttt ctcccttcgg gaagcgtggc   1080
gctttctcat agctcacgct gtaggtatct cagttcggtg taggtcgttc gctccaagct   1140
```

```
gggctgtgtg cacgaacccc ccgttcagcc cgaccgctgc gccttatccg gtaactatcg    1200
tcttgagtcc aacccggtaa gacacgactt atcgccactg gcagcagcca ctggtaacag    1260
gattagcaga gcgaggtatg taggcggtgc tacagagttc ttgaagtggt ggcctaacta    1320
cggctacact agaaggacag tatttggtat ctgcgctctg ctgaagccag ttaccttcgg    1380
aaaaagagtt ggtagctctt gatccggcaa acaaaccacc gctggtagcg gtggttttt    1440 tgtttgcaag cagcagatta cgcgcagaaa aaaggatct caagaagatc ctttgatctt    1500
ttctacgggg tctgacgctc agtggaacga aaactcacgt taagggattt tggtcatgag    1560
attatcaaaa aggatcttca cctagatcct tttaaattaa aaatgaagtt ttaaatcaat    1620
ctaaagtata tatgagtaaa cttggtctga cagttaccaa tgcttaatca gtgaggcacc    1680
tatctcagcg atctgtctat ttcgttcatc catagttgcc tgactccccg tcgtgtagat    1740
aactacgata cgggagggct taccatctgg ccccagtgct gcaatgatac cgcgagaccc    1800
acgctcaccg gctccagatt tatcagcaat aaaccagcca gccggaaggg ccgagcgcag    1860
aagtggtcct gcaactttat ccgcctccat ccagtctatt aattgttgcc gggaagctag    1920
agtaagtagt tcgccagtta atagtttgcg caacgttgtt gccattgcta caggcatcgt    1980
ggtgtcacgc tcgtcgtttg gtatggcttc attcagctcc ggttcccaac gatcaaggcg    2040
agttacatga tcccccatgt tgtgcaaaaa agcggttagc tccttcggtc ctccgatcgt    2100
tgtcagaagt aagttggccg cagtgttatc actcatggtt atggcagcac tgcataattc    2160
tcttactgtc atgccatccg taagatgctt ttctgtgact ggtgagtact caaccaagtc    2220
attctgagaa tagtgtatgc ggcgaccgag ttgctcttgc ccggcgtcaa tacgggataa    2280
taccgcgcca catagcagaa ctttaaaagt gctcatcatt ggaaaacgtt cttcggggcg    2340
aaaactctca aggatcttac cgctgttgag atccagttcg atgtaaccca ctcgtgcacc    2400
caactgatct tcagcatctt ttactttcac cagcgtttct gggtgagcaa aaacaggaag    2460
gcaaaatgcc gcaaaaaagg gaataagggc gacacggaaa tgttgaatac tcatactctt    2520
cctttttcaa tattattgaa gcatttatca gggttattgt ctcatgagcg gatacatatt    2580
tgaatgtatt tagaaaaata aacaaatagg ggttccgcgc acatttcccc gaaaagtgcc    2640
acctgacgtc taagaaacca ttattatcat gacattaacc tataaaaata ggcgtatcac    2700
gaggcccttt cgtctcgcgc gtttcggtga tgacggtgaa aacctctgac acatgcagct    2760
cccggagacg gtcacagctt gtctgtaagc ggatgccggg agcagacaag cccgtcaggg    2820
cgcgtcagcg ggtgttggcg ggtgtcgggg ctggcttaac tatgcggcat cagagcagat    2880
tgtactgaga gtgcaccata tatgcggtgt gaaataccgc acagatgcgt aaggagaaaa    2940
taccgcatca ggcgcctcct caacctgtat attcgtaaac cacgcccaat gggagctgtc    3000
tcaggtttgt tcctgattgg ttacggcgcg tttcgcatca ttgttgagtt tttccgccag    3060
cccgacgcgc agtttaccgg tgcctgggtg cagtacatca gcatgggca aattctttcc    3120 atcccgatga ttgtcgcggg tgtgatcatg atggtctggg catatcgtcg cagcccacag    3180
caacacgttt cctgaggaac catgaaacag tatttagaac tgatgcaaaa agtgctcgac    3240
gaaggcacac agaaaaacga ccgtaccgga accggaacgc tttccatttt tggtcatcag    3300
atgcgtttta acctgcaaga tggattcccg ctggtgacaa ctaaacgttg ccacctgcgt    3360
tccatcatcc atgaactgct gtggtttctg cagggcgaca ctaacattgc ttatctacac    3420
gaaaacaatg tcaccatctg ggacgaatgg gccgatgaaa acggcgacct cgggccagtg    3480
```

```
tatggtaaac agtggcgcgc ctggccaacg ccagatggtc gtcatattga ccagatcact    3540
acggtactga accagctgaa aaacgacccg gattcgcgcc gcattattgt ttcagcgtgg    3600
aacgtaggcg aactggataa aatggcgctg gcaccgtgcc atgcattctt ccagttctat    3660
gtggcagacg gcaaactctc ttgccagctt tatcagcgct cctgtgacgt cttcctcggc    3720
ctgccgttca acattgccag ctacgcgtta ttggtgcata tgatggcgca gcagtgcgat    3780
ctggaagtgg gtgattttgt ctggaccggt ggcgacacgc atctgtacag caaccatatg    3840
gatcaaactc atctgcaatt aagccgcgaa ccgcgtccgc tgccgaagtt gattatcaaa    3900
cgtaaacccg aatccatctt cgactaccgt ttcgaagact tgagattga  aggctacgat    3960
ccgcatccgg gcattaaagc gccggtggct atctaattac gaaacatcct gccagagccg    4020
acgccagtgt gcgtcggttt ttttacccct cgttaaattc ttcgagacgc cttcccgaag    4080
gcgccattcg ccattcaggc tgcgcaactg ttgggaaggg cgatcggtgc gggcctcttc    4140
gctattacgc cagctggcga aaggggggatg tgctgcaagg cgattaagtt gggtaacgcc    4200
agggttttcc cagtcacgac gttgtaaaac gacggccagt gccaagcttt ctttaatgaa    4260
gcagggcatc aggacggtat ctttgtggag aaagcagagt aatcttattc agcctgactg    4320
gtgggaaacc accagtcaga atgtgttagc gcatgttgac aaaaatacca ttagtcacat    4380
tatccgtcag tcggacgaca tggtagataa cctgtttatt atgcgttttg atcttacgtt    4440
taatattacc tttatgcgat gaaacggtct tggctttgat attcatttgg tcagagattt    4500
gaatggttcc ctgacctgcc atccacattc gcaacatact cgattcggtt cggctcaatg    4560
ataacgtcgg catatttaaa aacgaggtta tcgttgtctc ttttttcaga atatcgccaa    4620
ggatatcgtc gagagattcc ggtttaatcg atttagaact gatcaataaa ttttttctga    4680
ccaatagata ttcatcaaaa tgaacattgg caattgccat aaaaacgata ataacgtat    4740
tgggatgttg attaatgatg agcttgatac gctgactgtt agaagcatcg tggatgaaac    4800
agtcctcatt aataaacacc actgaagggc gctgtaatc  acaagctatg gcaaggtcat    4860
caacggtttc aatgtcgttg atttctcttt ttttaacccc tctactcaac agatacccgg    4920
ttaaacctag tcgggtgtaa ctacataaat ccataataat cgttgacatg gcataccctc    4980
actcaatgcg taacgataat tcccttacc  tgaatatttc atcatgacta aacggaacaa    5040
catgggtcac ctaatgcgcc actctcgcga ttttcaggc  ggacttacta tcccgtaaag    5100
tgttgtataa tttgcctgga attgtcttaa agtaaagtaa atgttgcgat atgtgagtga    5160
gcttaaaaca aatatttcgc tgcaggagta tcctggaaga tgttcgtaga agcttactgc    5220
tcacaagaaa aaaggcacgt catctgacgt gccttttta  tttgtactac cctgtacgat    5280
tactgcagct cgagttagga tttcgtttcg aattgggatt cgattttaac ccagtctttg    5340
cacaggatgt tttcgttacc gtaaatccag tgggacggac caatgataat ttttttccgga   5400
tttttgatca ggtaggctgc ccaccaggag taagtgctgt tagtgatgat accgtgtttg    5460
caagactgca tcagcatcat gtcccagtgg gctgcaccat cacgcgtcgt catgtcaaca    5520
aacgggtaac ccagatccag gttctgtacg aattccagat cctcgcagaa caggaacagt    5580
tccagatttt gaacacgttt tgccatatac gcaatggcgc gcagctggta ggagatgtcc    5640
agctgccagc ccaggcgcat gtaatcgcca cggcggatgt gaacgaacac agagttttc    5700
gcagccagga tctgggacag tttacgagag tactgttccg cgtgttcggt cgggtgaggc    5760
agggtgaaag tttgtttgat cagagggggag atatcttcga aatagcgcgg gtcctgaaag    5820
tagccatgga aatacgcaat gcggctcggt tcaaacagtt ccggcatgta ctcgaataca    5880
```

| | | |
|---|---|---|
| atttctttgc taacgcggcc cagacccata cgacgcagtg caccacgcac cagacgcggc | 5940 | |
| aggttctgca tgtgtgccgc ggcgatctgc tgggcggacg cacactgcag gtcgatcggg | 6000 | |
| aacaggtgca ggcccagttc acggttaccg taatcgaacc aagtggtatc cagcagtacc | 6060 | |
| ggaatgttca ggtgagtctg cagagattta gcgaatgcgt actggaacat ctggttaccc | 6120 | |
| aggccgccgt gcacctgaac gattttgaaa tccattatat ctccttcttg | 6170 | |

<210> SEQ ID NO 18
<211> LENGTH: 6155
<212> TYPE: DNA
<213> ORGANISM: Artificial Sequence
<220> FEATURE:
<223> OTHER INFORMATION: plasmid pG217

<400> SEQUENCE: 18

| | | |
|---|---|---|
| tctagaattc taaaaattga ttgaatgtat gcaaataaat gcatacacca taggtgtggt | 60 | |
| ttaatttgat gcccttttc agggctggaa tgtgtaagag cggggttatt tatgctgttg | 120 | |
| ttttttgtt actcgggaag ggcttacct cttccgcata aacgcttcca tcagcgttta | 180 | |
| tagttaaaaa atctttcgg aactggtttt gcgcttaccc caaccaacag gggatttgct | 240 | |
| gctttccatt gagcctgttt ctctgcgcga cgttcgcggc ggcgtgtttg tgcatccatc | 300 | |
| tggattctcc tgtcagttag cttttggtggt gtgtggcagt tgtagtcctg aacgaaaacc | 360 | |
| ccccgcgatt ggcacattgg cagctaatcc ggaatcgcac ttacggccaa tgcttcgttt | 420 | |
| cgtatcacac accccaaagc cttctgcttt gaatgctgcc cttcttcagg gcttaatttt | 480 | |
| taagagcgtc accttcatgg tggtcagtgc gtcctgctga tgtgctcagt atcaccgcca | 540 | |
| gtggtattta tgtcaacacc gccagagata atttatcacc gcagatggtt atctgtatgt | 600 | |
| tttttatatg aatttatttt ttgcagggg gcattgtttg gtaggtgaga gatcaattct | 660 | |
| gcattaatga atcggccaac gcgcggggag aggcggtttg cgtattgggc gctcttccgc | 720 | |
| ttcctcgctc actgactcgc tgcgctcggt cgttcggctg cggcgagcgg tatcagctca | 780 | |
| ctcaaaggcg gtaatacggt tatccacaga atcaggggat aacgcaggaa agaacatgtg | 840 | |
| agcaaaaggc cagcaaaagg ccaggaaccg taaaaaggcc gcgttgctgg cgttttccca | 900 | |
| taggctccgc cccctgacg agcatcacaa aaatcgacgc tcaagtcaga ggtggcgaaa | 960 | |
| cccgacagga ctataaagat accaggcgtt tccccctgga agctccctcg tgcgctctcc | 1020 | |
| tgttccgacc ctgccgctta ccggatacct gtccgccttt ctcccttcgg aagcgtggc | 1080 | |
| gctttctcat agctcacgct gtaggtatct cagttcggtg taggtcgttc gctccaagct | 1140 | |
| gggctgtgtg cacgaacccc ccgttcagcc cgaccgctgc gccttatccg gtaactatcg | 1200 | |
| tcttgagtcc aacccggtaa gacacgactt atcgccactg gcagcagcca ctggtaacag | 1260 | |
| gattagcaga gcgaggtatg taggcggtgc tacagagttc ttgaagtggt ggcctaacta | 1320 | |
| cggctacact agaaggacag tatttggtat ctgcgctctg ctgaagccag ttaccttcgg | 1380 | |
| aaaaagagtt ggtagctctt gatccggcaa acaaaccacc gctggtagcg tggtttttt | 1440 | |
| tgtttgcaag cagcagatta cgcgcagaaa aaaaggatct caagaagatc ctttgatctt | 1500 | |
| ttctacgggg tctgacgctc agtggaacga aaactcacgt taagggattt tggtcatgag | 1560 | |
| attatcaaaa aggatcttca cctagatcct tttaaattaa aaatgaagtt ttaaatcaat | 1620 | |
| ctaaagtata tatgagtaaa cttggtctga cagttaccaa tgcttaatca gtgaggcacc | 1680 | |
| tatctcagcg atctgtctat ttcgttcatc catagttgcc tgactcccg tcgtgtagat | 1740 | |

```
aactacgata cgggagggct taccatctgg ccccagtgct gcaatgatac cgcgagaccc    1800
acgctcaccg gctccagatt tatcagcaat aaaccagcca gccggaaggg ccgagcgcag    1860
aagtggtcct gcaactttat ccgcctccat ccagtctatt aattgttgcc gggaagctag    1920
agtaagtagt tcgccagtta atagtttgcg caacgttgtt gccattgcta caggcatcgt    1980
ggtgtcacgc tcgtcgtttg gtatggcttc attcagctcc ggttcccaac gatcaaggcg    2040
agttacatga tcccccatgt tgtgcaaaaa agcggttagc tccttcggtc ctccgatcgt    2100
tgtcagaagt aagttggccg cagtgttatc actcatggtt atggcagcac tgcataattc    2160
tcttactgtc atgccatccg taagatgctt ttctgtgact ggtgagtact caaccaagtc    2220
attctgagaa tagtgtatgc ggcgaccgag ttgctcttgc ccggcgtcaa tacgggataa    2280
taccgcgcca catagcagaa ctttaaaagt gctcatcatt ggaaaacgtt cttcggggcg    2340
aaaactctca aggatcttac cgctgttgag atccagttcg atgtaaccca ctcgtgcacc    2400
caactgatct tcagcatctt ttactttcac cagcgtttct gggtgagcaa aaacaggaag    2460
gcaaaatgcc gcaaaaaagg gaataagggc gacacggaaa tgttgaatac tcatactctt    2520
cctttttcaa tattattgaa gcatttatca gggttattgt ctcatgagcg gatacatatt    2580
tgaatgtatt tagaaaaata aacaaatagg ggttccgcgc acatttcccc gaaaagtgcc    2640
acctgacgtc taagaaacca ttattatcat gacattaacc tataaaaata ggcgtatcac    2700
gaggcccttt cgtctcgcgc gtttcggtga tgacggtgaa aacctctgac acatgcagct    2760
cccggagacg gtcacagctt gtctgtaagc ggatgccggg agcagacaag cccgtcaggg    2820
cgcgtcagcg ggtgttggcg ggtgtcgggg ctggcttaac tatgcggcat cagagcagat    2880
tgtactgaga gtgcaccata tatgcggtgt gaaataccgc acagatgcgt aaggagaaaa    2940
taccgcatca ggcgcctcct caacctgtat attcgtaaac cacgcccaat gggagctgtc    3000
tcaggtttgt tcctgattgg ttacggcgcg tttcgcatca ttgttgagtt tttccgccag    3060
cccgacgcgc agtttaccgg tgcctgggtg cagtacatca gcatgggca aattcttttcc   3120
atcccgatga ttgtcgcggg tgtgatcatg atggtctggg catatcgtcg cagcccacag    3180
caacacgttt cctgaggaac catgaaacag tatttagaac tgatgcaaaa agtgctcgac    3240
gaaggcacac agaaaaacga ccgtaccgga accggaacgc tttccatttt tggtcatcag    3300
atgcgtttta acctgcaaga tggattcccg ctggtgacaa ctaaacgttg ccacctgcgt    3360
tccatcatcc atgaactgct gtggtttctg cagggcgaca ctaacattgc ttatctacac    3420
gaaaacaatg tcaccatctg ggacgaatgg gccgatgaaa acggcgacct cgggccagtg    3480
tatggtaaac agtggcgcgc ctggccaacg ccagatggtc gtcatattga ccagatcact    3540
acggtactga accagctgaa aaacgacccg gattcgcgcc gcattattgt ttcagcgtgg    3600
aacgtaggcg aactggataa aatggcgctg gcaccgtgcc atgcattctt ccagttctat    3660
gtggcagacg gcaaactctc ttgccagctt tatcagcgct cctgtgacgt cttcctcggc    3720
ctgccgttca acattgccag ctacgcgtta ttggtgcata tgatggcgca gcagtgcgat    3780
ctggaagtgg gtgattttgt ctggaccggt ggcgacacgc atctgtacag caaccatatg    3840
gatcaaactc atctgcaatt aagccgcgaa ccgcgtccgc tgccgaagtt gattatcaaa    3900
cgtaaacccg aatccatctt cgactaccgt ttcgaagact tgagattga aggctacgat    3960
ccgcatccgg gcattaaagc gccggtggct atctaattac gaaacatcct gccagagccg    4020
acgccagtgt gcgtcggttt ttttaccctc cgttaaattc ttcgagacgc cttcccgaag    4080
gcgccattcg ccattcaggc tgcgcaactg ttgggaaggg cgatcggtgc gggcctcttc    4140
```

```
gctattacgc cagctggcga aaggggatg tgctgcaagg cgattaagtt gggtaacgcc    4200
agggttttcc cagtcacgac gttgtaaaac gacggccagt gccaagcttt ctttaatgaa    4260
gcagggcatc aggacggtat ctttgtggag aaagcagagt aatcttattc agcctgactg    4320
gtgggaaacc accagtcaga atgtgttagc gcatgttgac aaaaatacca ttagtcacat    4380
tatccgtcag tcggacgaca tggtagataa cctgtttatt atgcgttttg atcttacgtt    4440
taatattacc tttatgcgat gaaacggtct tggctttgat attcatttgg tcagagattt    4500
gaatggttcc ctgacctgcc atccacattc gcaacatact cgattcggtt cggctcaatg    4560
ataacgtcgg catatttaaa aacgaggtta tcgttgtctc tttttcaga atatcgccaa     4620 ggatatcgtc gagagattcc ggtttaatcg atttagaact gatcaataaa ttttttctga    4680
ccaatagata ttcatcaaaa tgaacattgg caattgccat aaaaacgata ataacgtat    4740 tgggatgttg attaatgatg agcttgatac gctgactgtt agaagcatcg tggatgaaac    4800
agtcctcatt aataaacacc actgaagggc gctgtgaatc acaagctatg gcaaggtcat    4860
caacggtttc aatgtcgttg atttctcttt ttttaaccc tctactcaac agatacccgg     4920
ttaaacctag tcgggtgtaa ctacataaat ccataataat cgttgacatg gcataccctc    4980
actcaatgcg taacgataat tcccttacc tgaatatttc atcatgacta acggaacaa      5040 catgggtcac ctaatgcgcc actctcgcga ttttcaggc ggacttacta tcccgtaaag     5100
tgttgtataa tttgcctgga attgtcttaa agtaaagtaa atgttgcgat atgtgagtga    5160
gcttaaaaca aatatttcgc tgcaggagta tcctggaaga tgttcgtaga agcttactgc    5220
tcacaagaaa aaaggcacgt catctgacgt gcctttttta tttgtactac cctgtacgat    5280
tactgcagct cgagttagga taccggcact ttgatccaac cagtcgggta gatatccggt    5340
gcttcggagt gctggaacca acggctcggc acaataacag tcttatccat attagggttc    5400
agccaggcac cccaccaaga aaacgtgctg ttacaaatga tgtgatgttt gcaatgagac    5460
atcagcatca tatcctgcca ggagtcttca tcagtgttcc agtcaatata aaccgcattc    5520
tgcagtggca gattttcttt aacccacgcg atatcgtcgg agaagatata gtaagatggg    5580
ctagcaacac gacgggacat ttccgcgata gcattctggt aatacggcag ctggcacacg    5640
gaaccggtag tagcccagtg tttcggctgc agatagtcac cacgacgaat gtgcagggaa    5700
accgcgtttt catctttgtc caggatttcc agcatgttca ggctgcggga atttgctttg    5760
ttcttatcaa aggtgaagga ttcacgcact tcgtctttga tatcagcgaa gaaacgctcg    5820
ctctgataga aacctttaaa gtacagcagc ggccagaaat acttcttctc gaacgcacgc    5880
agagagttcg gcgcctgctt gcgttcgtag attttttaa aaaacaggaa ttcgataact    5940
tttttcagcg gttggttgat gcagaattcg gtgtgcggca ggttgaacac gcggtgcatt    6000
tcgtaaccgt aatggacttt gtaatgcatc atgtcgctca ggtcgatacg gaccttcggg    6060
taatactttt tcatacgcag atagaaagca tagataaaca tctggttgcc cagaccgcca    6120
gtcactttga tcagacgcat tatatctcct tcttg                               6155
```